US012637510B2

(12) United States Patent
Yu et al.

(10) Patent No.: US 12,637,510 B2
(45) Date of Patent: May 26, 2026

(54) ONCOLYTIC VIRUS COMPOSITIONS AND METHODS FOR THE TREATMENT OF CANCER

(71) Applicant: CITY OF HOPE, Duarte, CA (US)

(72) Inventors: Jianhua Yu, Duarte, CA (US); Michael A. Caligiuri, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 860 days.

(21) Appl. No.: 17/797,681

(22) PCT Filed: Feb. 6, 2021

(86) PCT No.: PCT/US2021/016973
§ 371 (c)(1),
(2) Date: Aug. 4, 2022

(87) PCT Pub. No.: WO2021/159035
PCT Pub. Date: Aug. 12, 2021

(65) Prior Publication Data
US 2023/0227549 A1 Jul. 20, 2023

Related U.S. Application Data

(60) Provisional application No. 62/971,768, filed on Feb. 7, 2020.

(51) Int. Cl.
| | |
|---|---|
| *A61K 35/763* | (2015.01) |
| *A61K 31/502* | (2006.01) |
| *A61K 39/00* | (2006.01) |
| *A61P 15/08* | (2006.01) |
| *A61P 35/00* | (2006.01) |
| *A61P 37/04* | (2006.01) |
| *C07K 16/28* | (2006.01) |
| *C12N 15/86* | (2006.01) |

(52) U.S. Cl.
CPC ........ *C07K 16/2803* (2013.01); *A61K 31/502* (2013.01); *A61K 35/763* (2013.01); *A61K 39/001111* (2018.08); *A61K 39/001129* (2018.08); *A61P 15/08* (2018.01); *A61P 35/00* (2018.01); *A61P 37/04* (2018.01); *C12N 15/86* (2013.01); *A61K 2039/505* (2013.01); *C07K 2317/24* (2013.01); *C07K 2317/52* (2013.01); *C07K 2317/73* (2013.01); *C12N 2710/16632* (2013.01); *C12N 2710/16643* (2013.01); *C12N 2710/16662* (2013.01); *C12N 2710/16671* (2013.01)

(58) Field of Classification Search
None
See application file for complete search history.

(56) References Cited

U.S. PATENT DOCUMENTS

| | | | |
|---|---|---|---|
| 7,214,515 B2 | 5/2007 | Chiocca et al. | |
| 9,862,932 B2* | 1/2018 | Shah | C12N 7/00 |
| 10,604,574 B2* | 3/2020 | Evnin | A61P 35/02 |
| 2002/0187163 A1 | 12/2002 | Johnson et al. | |
| 2015/0250837 A1* | 9/2015 | Nolin | A61K 35/761 |
| | | | 435/235.1 |
| 2016/0244740 A1 | 8/2016 | Kaur | |
| 2017/0210811 A1 | 7/2017 | Wong et al. | |
| 2018/0117146 A1 | 5/2018 | Yu et al. | |
| 2019/0048082 A1 | 2/2019 | Evnin | |
| 2019/0169253 A1 | 6/2019 | Jia et al. | |
| 2020/0236916 A1 | 7/2020 | Shultz | |
| 2023/0147832 A1 | 5/2023 | Yu et al. | |

FOREIGN PATENT DOCUMENTS

| | | |
|---|---|---|
| WO | WO-2008/151182 | 12/2008 |
| WO | WO-2019/032866 A1 | 2/2019 |
| WO | WO-2019/129233 A1 | 7/2019 |
| WO | WO-2020/163721 A1 | 8/2020 |
| WO | WO-2021/150936 A1 | 7/2021 |

OTHER PUBLICATIONS

Lee, et al. (2016) "Upregulation of CD47 in Regulatory T Cells in Atopic Dermatitis", Yonsei Medical Journal, 57(6): 1435-45. (Year: 2016).*
Drean, et al. (2016) "PARP inhibitor combination therapy", Critical Reviews in Oncology/Hematology, 108: 73-85. (Year: 2016).*
Lai, et al. (2021) "Differences in human IgG1 and IgG4 S228P monoclonal antibodies viscosity and self-interactions: Experimental assessment and computational predictions of domain interactions", MABS, 13(1): e1991256, 19 pages. (Year: 2021).*
Glorioso, J.C. et al. (2021, e-published Sep. 17, 2020). "Oncolytic HSV Vectors and Anti-Tumor Immunity," *Molecular Biology* 41:381-468.
International Search Report mailed on Apr. 27, 2021 for PCT Application No. PCT/US2021/016973, filed Feb. 6, 2021, 3 pages.
International Search Report mailed on Jun. 4, 2021 for PCT Application No. PCT/US2021/014683, filed Jan. 22, 2021, 5 pages.
Written Opinion mailed on Apr. 27, 2021 for PCT Application No. PCT/US2021/016973, filed Feb. 6, 2021, 7 pages.
Written Opinion mailed on Jun. 4, 2021 for PCT Application No. PCT/US2021/014683, filed Jan. 22, 2021, 5 pages.
Barclay, A.N. et al. (2014, e-published Nov. 6, 2013). "The interaction between signal regulatory protein alpha (SIRPα) and CD47: structure, function, and therapeutic target," *Annual Review Immunology* 32:25-50.
Extended European Search Report mailed on Feb. 27, 2024, for EP Patent Application No. 21750415.8, 11 pages.
Huang, Y. et al. (Mar. 2020, e-published Feb. 7, 2020). "A SIRPα-Fc fusion protein enhances the antitumor effect of oncolytic adenovirus against ovarian cancer," *Mol Oncol* 14(3):657-668.

(Continued)

*Primary Examiner* — Robert M Kelly
(74) *Attorney, Agent, or Firm* — Mintz, Levin, Cohn, Ferris, Glovsky and Popeo, P.C.

(57) ABSTRACT

Provided herein, inter alia, are compositions and methods including recombinant oncolytic viruses expressing CD47 antibody for the treatment of diseases including cancer, immune disorders, and infectious disease.

15 Claims, 70 Drawing Sheets

Specification includes a Sequence Listing.

(56) References Cited

OTHER PUBLICATIONS

Matlung, H.L. et al. (Mar. 4, 2017). "The CD47-SIRPα signaling axis as an innate immune checkpoint in cancer," *Immunological Reviews* 276(1):145-164.

Passaro, C. et al. (Oct. 2, 2018). "Arming an Oncolytic Herpes Simplex Virus Type 1 with a Single-chain Fragment Variable Antibody against PD-1 for Experimental Glioblastoma Therapy," *Clin Cancer Research* 25(1):290-299.

Sivanandam, V. et al. (Apr. 25, 2019). "Oncolytic Viruses and Immune Checkpoint Inhibition: The Best of Both Worlds," *Mol Ther Oncolytics* 13:93-106.

Xu, B. et al. (Oct. 8, 2021). "An oncolytic virus expressing a full-length antibody enhances antitumor innate immune response to glioblastoma," *Nature Communications* 12(1):5908.

Chen, X. et al. (Apr. 1, 2016). "A combinational therapy of EGFR-CAR Nk cells and oncolytic herpes simplex virus 1 for breast cancer brain metastases," *Oncotarget* 7(19):27764-27777.

* cited by examiner

ONCOLYTIC VIRUS COMPOSITIONS AND METHODS FOR THE TREATMENT OF CANCER

CROSS-REFERENCE TO RELATED APPLICATIONS

This application is a National Stage Entry of PCT Application No. PCT/US2021/016973, filed Feb. 6, 2021, which claims priority to U.S. Provisional Application No. 62/971,768, filed Feb. 7, 2020, which are hereby incorporated by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. R01 NS106170 and POT CA163205 awarded by the National Institutes of Health. The government has certain rights in the invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 048440-748001WO-SEQUENCE_LISTING_ST25.TXT, created on Feb. 5, 2021, 11,491 bytes, machine format IBM-PC, MS Windows operating system, is hereby incorporated by reference.

BACKGROUND

Oncolytic viral (OV) therapy has been recognized as a promising approach for cancer treatment. It differs from traditional gene therapy where a viral vector serves for delivery of a specific gene. OV therapy utilizes the virus itself as an immune stimulatory agent that can also selectively replicate in tumor cells resulting in their lysis without harming normal tissues. The concept of OV therapy has existed for decades. OV therapy is effective at treating preclinical models of brain tumors with a genetically engineered herpes simplex virus type I (HSV-1) containing a mutation in the thymidine kinase (TK) gene. This encouraged researchers to further modify the viral genome to design an oncolytic HSV-1 (oHSV). Over the past two decades, it has been established that oHSV can boost systemic immunity and therefore the anti-tumor immune response.

Glioblastoma (GBM) is the most common and aggressive primary malignant brain tumor. GBM patients who undergo the standard of care, including surgical resection, chemotherapy and radiotherapy, have a median survival of only approximately 15 months. Due to the early infiltrative nature of the disease, a complete surgical resection of GBM is largely unachievable. The intrinsic resistance of GBM to the chemo- and radiotherapy also contributes to the poor clinical outcomes. Given these attributes, new therapeutic agents are urgently needed for to improve the median survival. (See, for example, Ref. 1). Provided herein are solutions to these and other problems in the art.

Ovarian cancer is the most lethal gynecological malignancies (see, for example, Refs. 44-47). Although a lot of efforts have been made for improving the treatment of ovarian cancer by more aggressive surgical approaches and the introduction of more effective chemotherapy, the 5-year overall survival for the advanced ovarian cancer is approximately 30%. Increasing evidence, from preclinical and clinical data, indicates that immunotherapy approaches that harness and enhance antitumor effector cells, such as immune checkpoint blockade therapy and tumor specific monoclonal antibody therapy, have led to clinical benefits for ovarian cancer (see, for example, Ref. 48).

CD47 was first identified as a tumor antigen on human ovarian cancer in the 1980s (see, for example, Refs. 49-50). CD47 overexpression is found to be associated with poor prognosis in ovarian cancer (see, for example, Refs. 51-52). CD47 provides a "do not eat" signal by binding to its receptor, signal regulatory protein alpha (SIRPα) on macrophages and suppresses the phagocytosis (see, for example, Refs. 53-54). Targeting CD47 therapy has been proven as an effective treatment for ovarian cancer, with several clinical trials (see, for example, Refs. 51, 55, 56).

However, the traditional delivery methods of antibody drugs such as intravenous (i.v.), subcutaneous (s.c.), or intramuscular (i.m.) administration result in limited tumor tissue distribution of the antibodies, but leave most of the administrated antibodies remaining in the peripheral circulatory system that leads to side effects (see, for example, Refs. 57-58).

BRIEF SUMMARY OF THE INVENTION

In an aspect, provided herein is a recombinant oncolytic virus including an expression cassette encoding an anti-CD47 antibody. In an aspect, provided herein is a recombinant oncolytic virus including a nucleic acid encoding an anti-CD47 antibody.

In an aspect, provided herein is a pharmaceutical composition including a recombinant oncolytic virus as described herein, and a pharmaceutically acceptable carrier. In an aspect, the pharmaceutical composition further includes an anti-cancer agent.

In an aspect, provided herein is a combination therapy including a pharmaceutical composition that includes a recombinant oncolytic herpes simplex virus as described herein and an anticancer agent. In an aspect, the anti-cancer agent is a checkpoint inhibitor.

In an aspect, provided herein is a method for killing tumor cells in a subject including administering to a subject an effective amount of the recombinant oncolytic virus according to any embodiment as described herein. In an aspect, the method further includes administering to a subject an anti-cancer agent.

In an aspect, provided herein is a method of treating cancer to a subject in need including administering to the subject an effective amount of a pharmaceutical composition including a recombinant oncolytic virus as described above, and a pharmaceutically acceptable carrier as described herein or the recombinant oncolytic virus according to any embodiment as described herein. In an aspect, the method further includes administering to a subject an anti-cancer agent.

BRIEF DESCRIPTION OF THE DRAWINGS

FIG. 1A shows a schematic map of oncolytic viruses used in this study. Top: genetic map of wild type HSV-1. Second: genetic map of control oHSV, OV-Q1, with deletion of two copies of γ34.5, dysfunction of ICP6, and insertion of the GFP gene. Third: genetic map of OV-Hu5F9-G1 showing the inserted coding gene of IgG1 version of anti-CD47 (αCD47-G1) that is constructed on human IgG1 scaffold. The light chain and heavy chain coding genes of αCD47-G1 are linked by a T2A sequences and are driven by the viral pIE4/5 promoter. Fourth: The genetic map of OV-αCD47-G4 demonstrating the inserted coding gene of the IgG4 version of anti-CD47 (αCD47-G4) that is constructed on the scaffold of human IgG4 instead of IgG1. FIG. 1B shows immunoblotting performed with concentrated supernatants of engineered CHO cells and oHSV-infected U251T2 cells. Lentiviral-infected CHO cells (CHO-αCD47-G1 and CHO-αCD47-G4) were used to produce pure αCD47-G1 and αCD47-G4. 10 ml supernatants were collected from cultured CHO-EV (empty vector), CHO-αCD47-G1 and CHO-αCD47-G4 cells, as well as OV-Q1-infected, OV-αCD47-G1-infected and OV-αCD47-G4-infected U251T2 cells at 24 hours after infection. FIG. 1C shows that human CD47 binding affinity of αCD47-G1 and αCD47-G4 were tested by flow cytometry assay. Stained cells were tested on flow cytometry, αCD47-G1 and αCD47-G4 both showed dose-dependent increase on APC signal. FIG. 1D shows that the human CD47 neutralizing activity of αCD47-G1 and αCD47-G4 were also tested by flow cytometry assay. Stained cells were tested by flow cytometry. αCD47-G1 and αCD47-G4 both showed a dose-dependent decrease of BV786 signal. FIG. 1E shows that αCD47-G1 and αCD47-G4 yields of OV-αCD47-G1- and OV-αCD47-G4-infected GBM cells were tested by ELISA assay.

FIG. 2A shows that U251T2 and Gli36ΔEGFR cells were infected with OV-Q1, OV-αCD47-G1 or OV-αCD47-G4 at the indicated MOIs. Cell survival was analyzed at 5 days after infection by CCK8 assay. The dose response curves were established for each virus to calculate the viral Lethal Dose 50 (LD50, pfu/mL). FIG. 2B shows that U251T2 and Gli36ΔEGFR cells were infected with OV-Q1, OV-αCD47-G1 or OV-αCD47-G4 at a MOI of 3. The supernatants were harvested at indicated time points and checked for viral reproduction using a plaque assay in Vero cells. FIG. 2C shows that OV-αCD47-G1 and OV-αCD47-G4-infected U251T2 GBM cells (FIG. 2C) produce similar amounts of oHSV when compared to the same GBM cells infected with the parental oHSV OV-Q1. FIG. 2D shows that OV-αCD47-G1 and OV-αCD47-G4-infected Gli36 GBM cells (FIG. 2D) produce similar amounts of oHSV when compared to the same GBM cells infected with the parental oHSV OV-Q1. Therefore, engineering oHSV to infect GBM with Hu5F9-G1 or Hu5F9-G4 did not affect their oncolysis or viral production.

FIGS. 3A-3D show examination of the effect of αCD47-G1 and αCD47-G4 purified from CHO cells on phagocytosis of GBM cells by bone-marrow-derived-macrophages (BMDM). GBM43 (FIG. 3A and FIG. 3B) and BT422 (FIG. 3C and FIG. 3D) cells were labeled with CFSE and co-cultured with BMDM at the ratio of 1:2 in the presence of control, αCD47-G1 or αCD47-G4 at the dose of 5 μg/ml. Percentage of BMDM uptake of labeled tumor cells (CD11b+ and CFSE+) were measured by flow cytometry assay to evaluate the phagocytosis rates. FIGS. 3E-3F show conditional media of OV-αCD47-G1- and OV-OV-αCD47-G4-infected GBM cells induce phagocytosis of GBM cells by BMDM. GBM43 and BT422 cells were labeled with CFSE and co-cultured with BMDM at the ratio of 1:2 in the presence of supernatants from OV-Q1, OV-αCD47-G1- or OV-αCD47-G4 infected U251T2 cells that were collected at 24 hours after infection. Percentage of BMDM uptake of labeled tumor cells (CD11b+ and CFSE+) were measured by flow cytometry assay to evaluate the phagocytosis rates. FIG. 3G shows results from phagocytosis assay performed with Fc receptor blocking. FIG. 3H shows cytokine gene transcription assay results.

FIGS. 4A-4B show cytotoxicity of human primary NK cells against αCD47-G1- and αCD47-G4-treated GBM43 (FIG. 4A) and BT422 (FIG. 4B) cells at the effector:target ratios of 40:1, 20:1 and 10:1. FIG. 4C shows cytotoxicity of human primary NK cells against GBM43 cells that were treated with conditional medium from OV-Q1-, OV-αCD47-G1- or OV-αCD47-G4-infected U251T2 cells. FIG. 4D shows that αCD47-G1 but not αCD47-G4 induces expression of the NK cell activation marker CD69 when co-cultured with GBM43 cells that were pretreated with αCD47-G1 or αCD47-G4. FIG. 4E is a graphical representation of the data in FIG. 4D.

FIG. 5A shows experimental timeline for in vivo studies. An orthotopic model of human GBM was established by i.c. injection of 1×10$^5$ GBM43-FFL human GBM cells into athymic nude mice. Seven days later, mice were intratumorally injected with a vehicle control or 2×10$^5$ PFU of OV-Q1, OV-αCD47-G1, or OV-αCD47-G4. Mice were weighed every other day and luciferase-based images were taken 15 days post tumor implantation to evaluate tumor progression. FIG. 5B shows time-lapse luciferase imaging of GBM43-FLL GMB mice with indicated treatments. FIG. 5C shows survival of GBM43 tumor-bearing mice treated with OV-Q1, OV-αCD47-G1, OV-αCD47-G4 or vehicle control. P<0.01 for the primary hypothesis of OV-αCD47-G1 vs. OV-αCD47-G4. In secondary hypothesis testing, P<0.01 for OV-αCD47-G1 vs. OV-Q1 and P<0.001 for OV-αCD47-G1 vs. control. Survival was estimated by the Kaplan-Meier method and compared by log rank test (n=9 animals). *Two mice in the OV-Q1 control group died accidently after i.p. injection of luciferin on days 16 and 27 without obvious GBM symptoms. FIG. 5D shows individual body weights recorded in mice treated on the experimental study. FIG. 5E shows the luciferase intensity of the experimental mice shown in FIG. 5B measured at 35 days post tumor implantation. Data presented are for individual mice (n=7 for OV-Q1 and 9 for other groups). Error bars represent standard deviations of all individual mice.

FIG. 6A shows experimental timeline for in vivo studies. Xenograft GBM mouse models were established by intracranially injecting 1×10$^5$ GBM43-FLL cells to athymic nude mice. Fourteen days later, mice were intratumorally injected with 2×10$^5$ PFU of OV-Q1, OV-αCD47-G1 or vehicle. The group of OV-Q1-plus-Hu5F9-G1 received i.p. administrated αCD47-G1 twice on day 15 and day 17 at the dose of 150 μg/mouse. The mice were monitored and the survival data were recorded. FIG. 6B shows survival of GBM43 tumor-bearing mice treated with OV-Q1, OV-Q1 plus αCD47-G1, OV-αCD47-G1, or vehicle control as indicated in FIG. 6A. FIG. 6C shows experimental timeline for in vivo studies. Xenograft GBM mouse models were established by intracranially injecting 1×10$^5$ GBM43 cells to athymic nude mice. Twenty-one days later, mice were intratumorally injected with $2\times10^5$ PFU of OV-Q1, OV-αCD47-G1 or vehicle. The group of OV-Q1-plus-αCD47-G1 received i.p. administrated αCD47-G1 twice on day 22 and day 24 at the dose of 150 μg/mouse. The mice were euthanized on day 23 and day 25 to harvest tissue. FIG. 6D shows that the plasma concentration of αCD47-G1 in different groups were measured by ELISA assay.

FIG. 7A show IgG1 and IgG4 versions of anti-CD47 (αCD47) both exhibit dose-dependent binding affinity to CD47 positive cells. FIG. 7B shows that IgG1 and IgG4 versions of anti-CD47 (αCD47) both block the binding sites of CD47 in a dose-dependent manner.

FIG. 8A shows cytotoxicity of human primary NK cells against Gli36ΔEGFR human GBM cells pretreated with different doses of αCD47-G1 or αCD47-G4 for 20 min. The NK cells were added to the pre-treated GBM cells without washing at the effector:target ratios of 40:1, 20:1 and 10:1 in a $^{51}$Cr release assay. FIG. 8B shows cytotoxicity of primary human NK cells against αCD47-G1- and αCD47-G4-pretreated three human GBM lines: GBM30, U251T2 and LN229. A linear mixed model was used to account for the underlying variance and covariance structure (n=4 donors). FIG. 8C shows αCD47-G1 but not αCD47-G4 induced the expression of the NK cell activation marker CD69. GBM30 or U251T2 human GBM cells that were pretreated with αCD47-G1 or αCD47-G4 at the concentration of 1 μg/ml and then co-cultured with primary human NK cells at a ratio of 1:1 for 4 hours. No wash of GBM cells was applied before NK cells were added. CD69 expression on NK cells was measured by flow cytometry to quantify the level of NK cell activation. FIG. 8D shows a statistic summary of the data provided in FIG. 8C. The bars left to right in top panel are NK+GBM30, NK+GBM30+αCD47-G1, NK+GBM30+αCD47-G4. The bars left to right in bottom panel are NK+U251T2, NK+U251T2+αCD47-G1, NK+U251T2+αCD47-G4. One-way ANOVA with Bonferroni's multiple comparisons test (n=4 donors). Experiments in FIG. 8C and FIG. 8D were repeated with primary NK cells isolated from 4 different donors with similar results. All experiments were performed with four donors in triplicate. Error bars represent standard deviations of means of four donors.

Figure 13A:
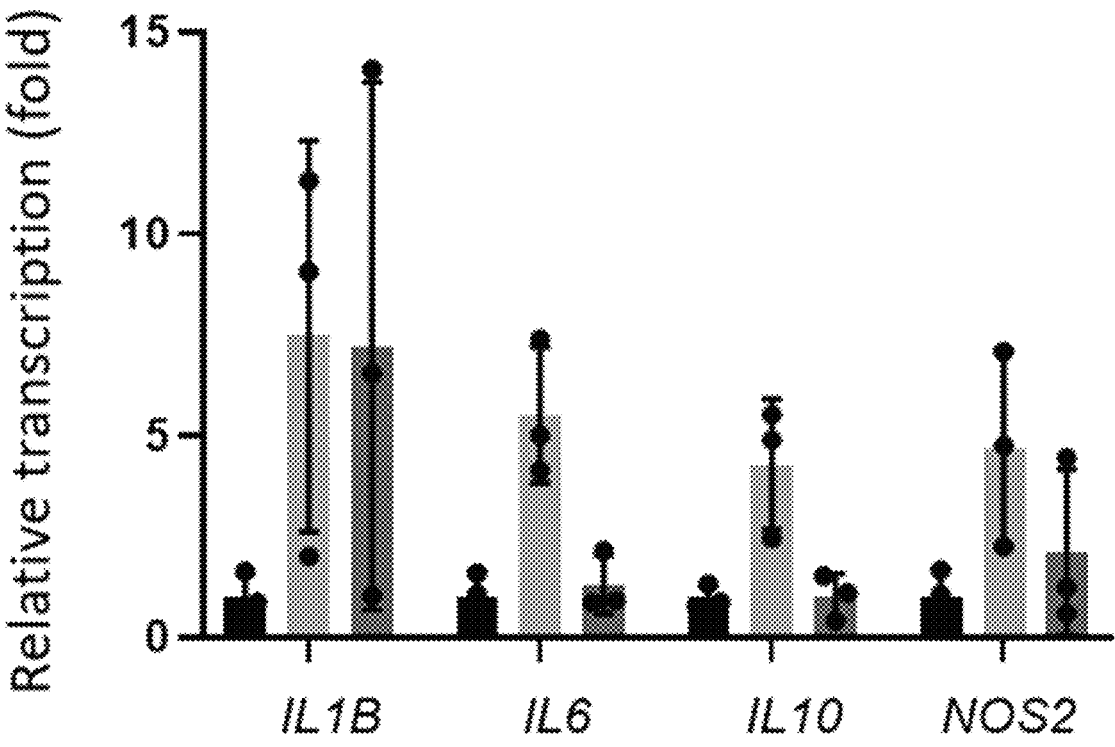
FIGS. 13A-13B show the effect of coculturing primary human macrophages with GBM43 cells at a ratio of 1:1 with or without αCD47-G1 or αCD47-G4 (bars left to right for each indicated transcript is without antibody, with αCD47-
Figure 13B:
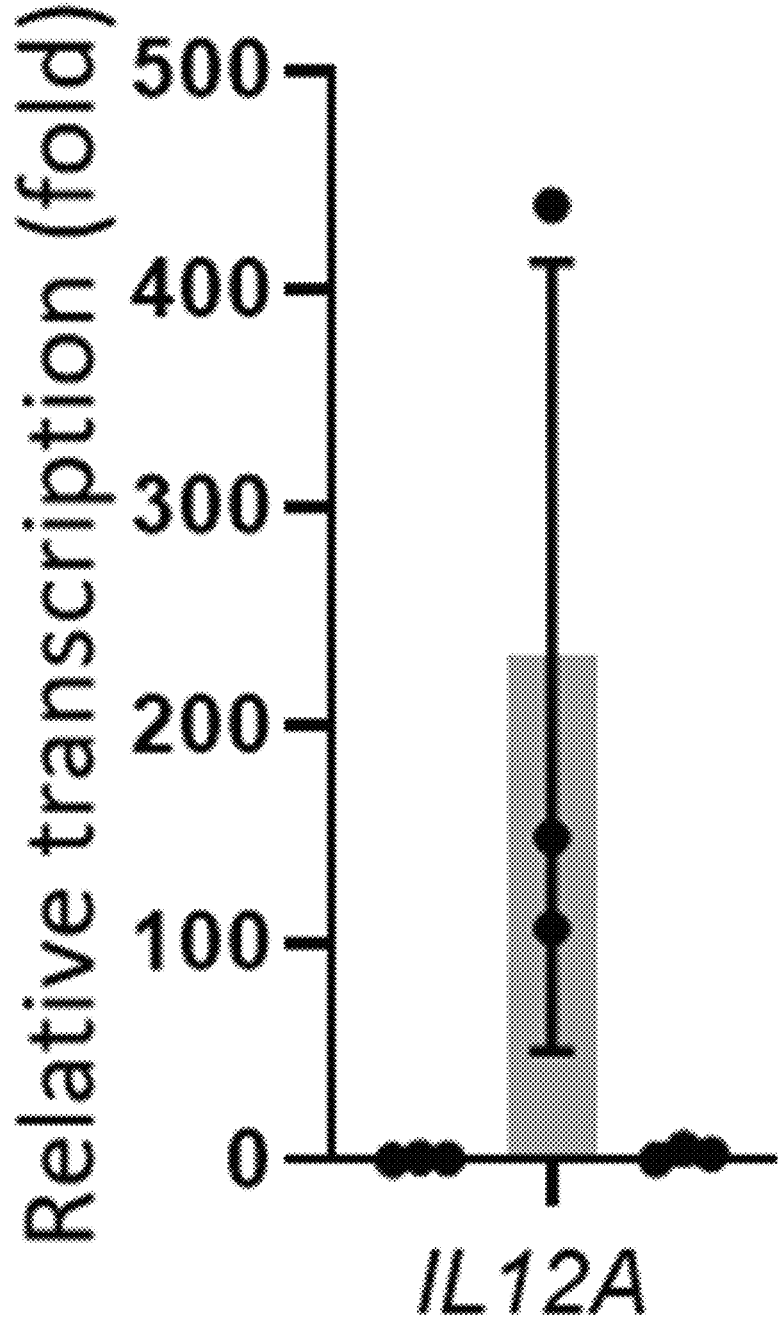

G1, or with αCD47-G4, correspondingly) for 6 hours on transcription of IL1B, IL6, IL10, NOS2 (FIG. 13A) and IL12A (FIG. 13B).

Figure 14:
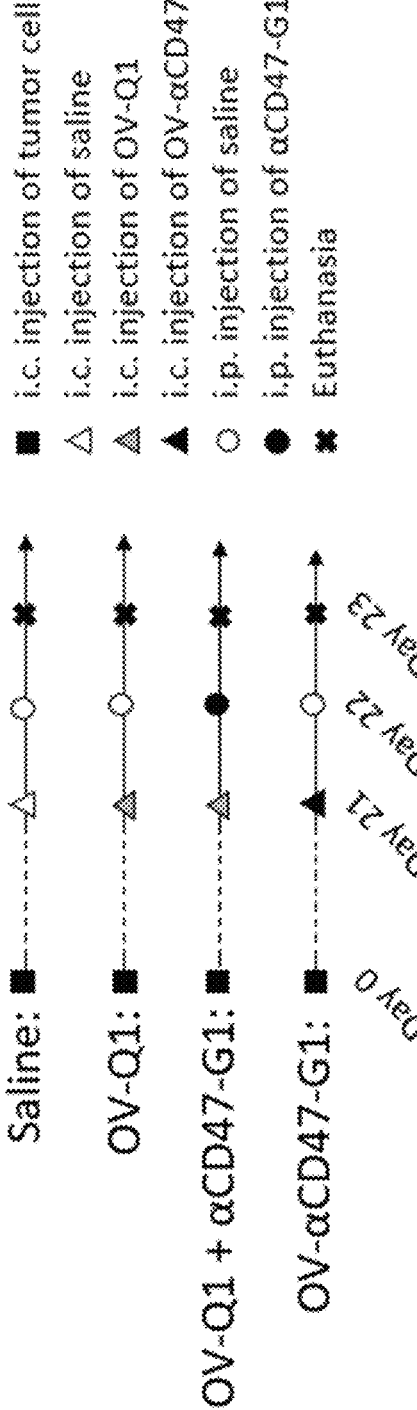

FIG. 14 shows an experimental timeline for in vivo studies using an orthotopic model of human GBM. Group 1, saline; Group 2, OV-Q1; Group 3, a combination of OV-Q1 plus i.p. administration of αCD47-G1; and Group 4, OV-αCD47-G1. After tumor implantation, Groups 2, 3 and 4 received intracranial injection of oHSV (OV-Q1 or OV-αCD47-G1) at a dose of $2\times10^5$ PFU per mouse on day 21. Group 1 received saline as control. On day 22, Group 3 received i.p. injection of purified αCD47-G1 at the dose of 150 μg per mouse. Groups 1, 2, and 4 received i.p. injection of saline as control. All mice were euthanized on day 23 for blood and brain harvesting.

Figure 15A:
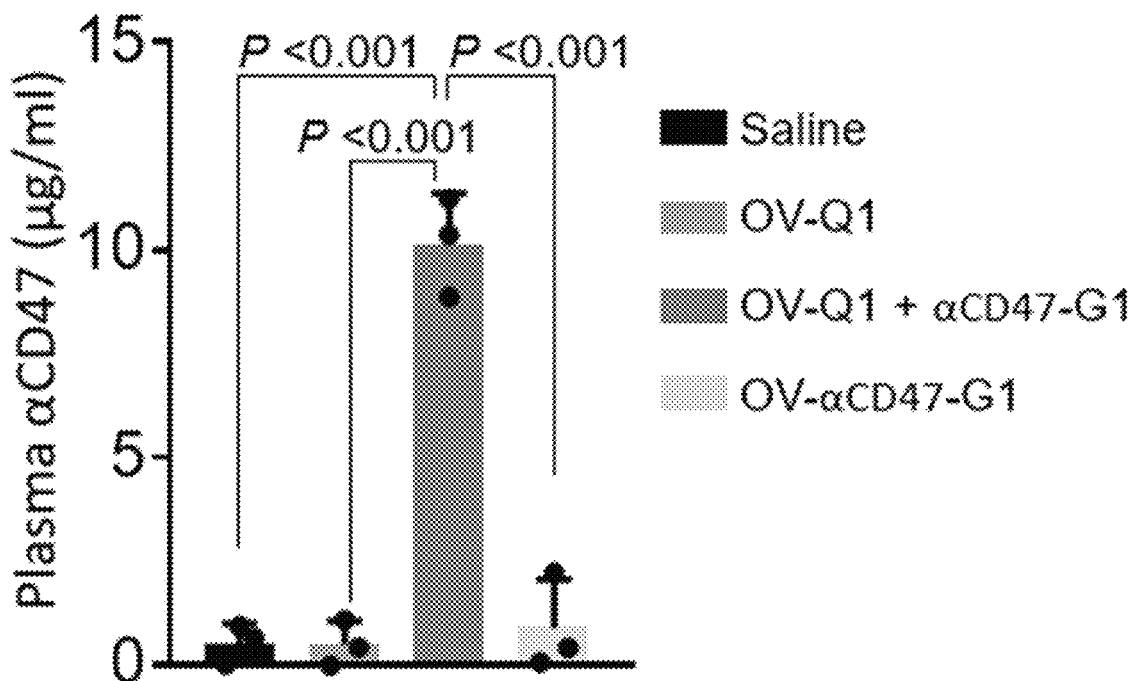
Figure 15B:
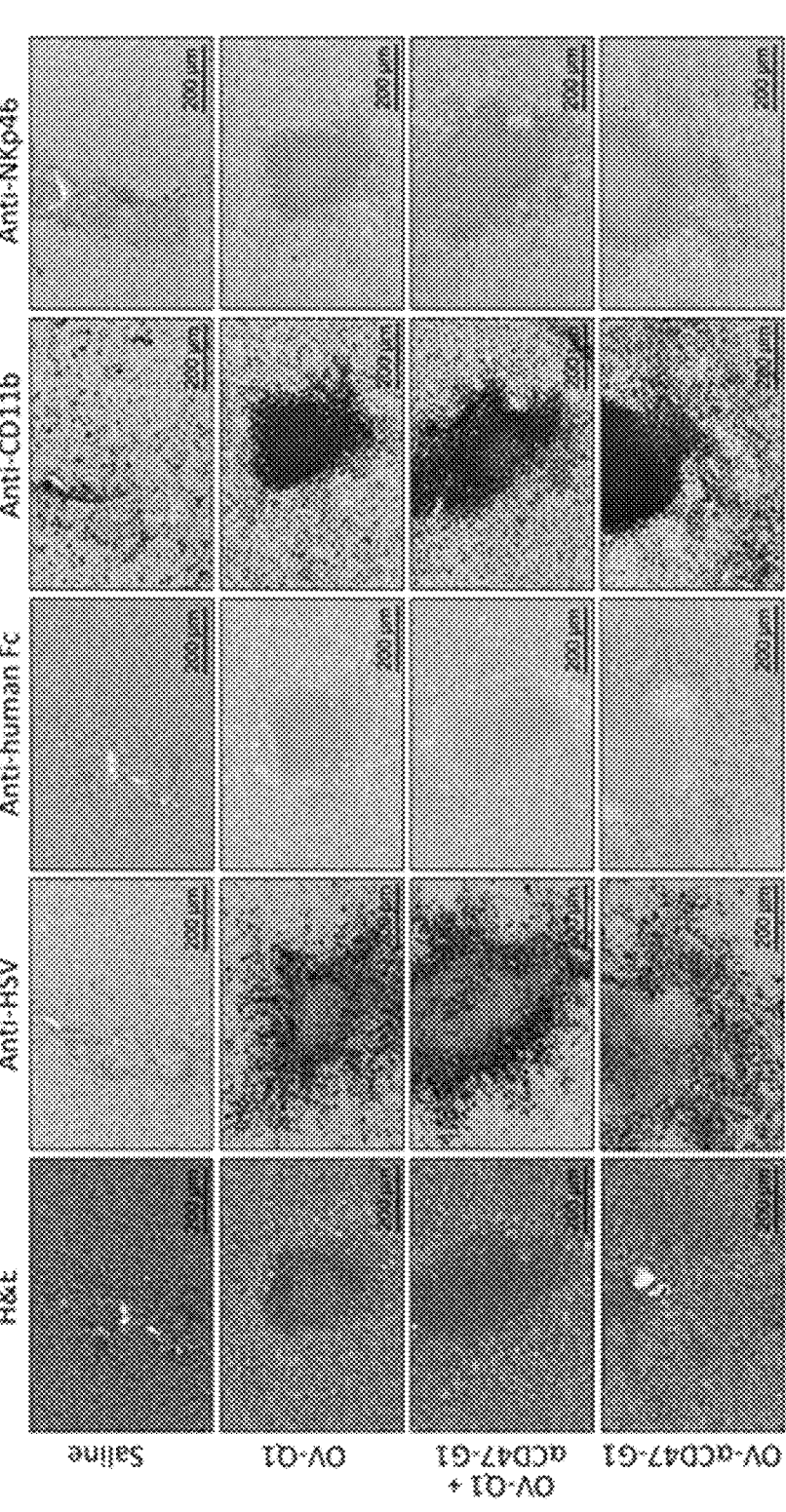
Figure 15C:
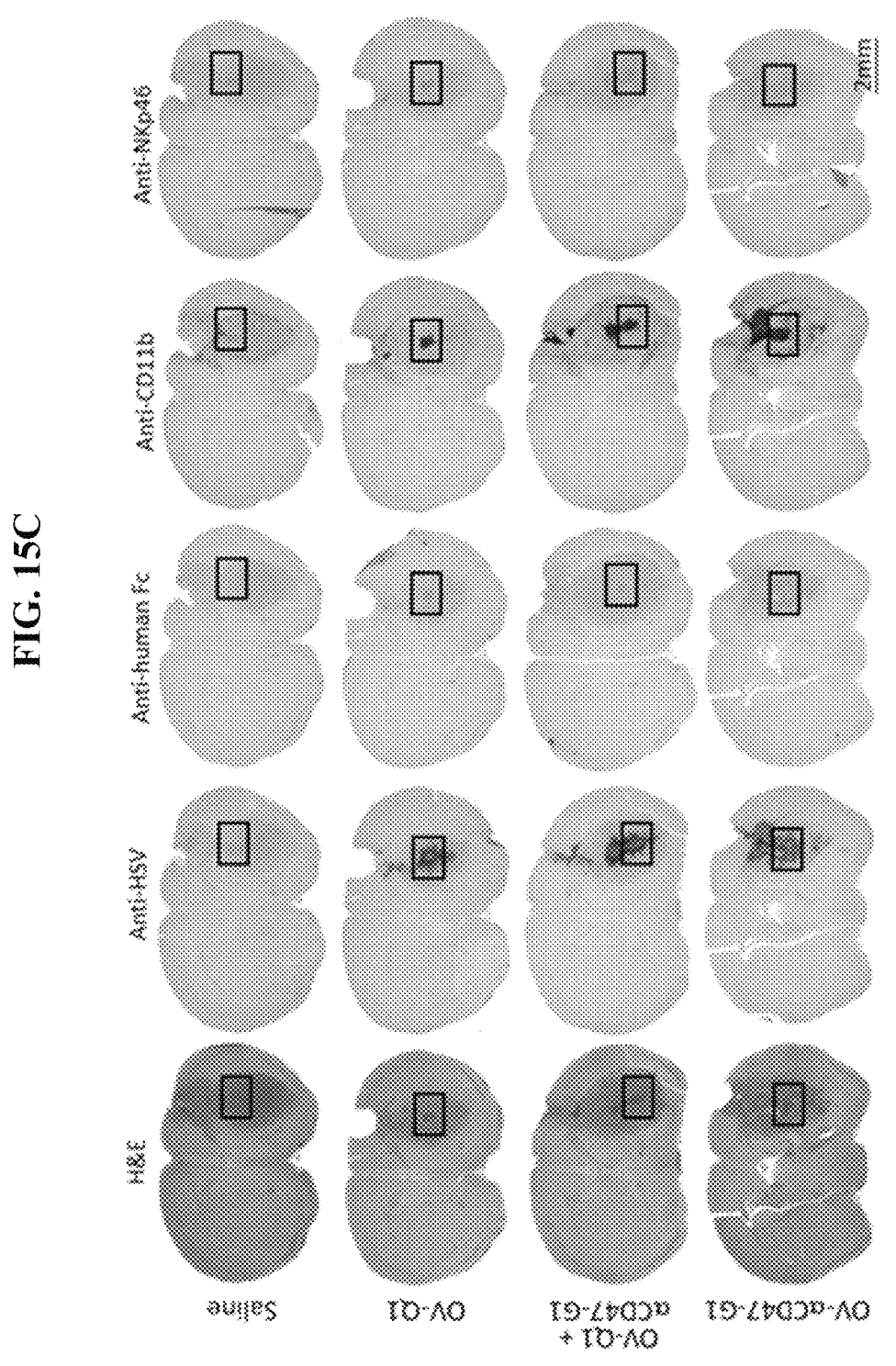

FIGS. 15A-15C shows OV-αCD47-G1 is effective for locoregional delivery of the anti-CD47 antibody, while systemic administration of αCD47-G1 is not effective. FIG. 15A shows the concentration of αCD47-G1 in plasma was measured by ELISA in mice from different treatments. The columns left to right are saline, OV-Q1, OV-Q1 plus αCD47-G1, and OV-αCD47-G1. FIG. 15B and FIG. 15C shows slides from the brain tissues isolated from experimental mice were subjected to H&E and immunohistochemical staining, the latter with anti-HSV, anti-human Fc, which identifies IgG, anti-CD11b or anti-NKp46 antibodies. Images with high and low magnifications are shown in FIG. 15B and FIG. 15C, respectively. The boxed images in FIG. 15B are shown in higher power in FIG. 15C. Data presented are represented of one (FIG. 15B and FIG. 15C) or three (FIG. 15A) mice of at least three mice in total with similar data. Error bars (FIG. 15A) represent standard deviations of means of three mice.

Figure 16:
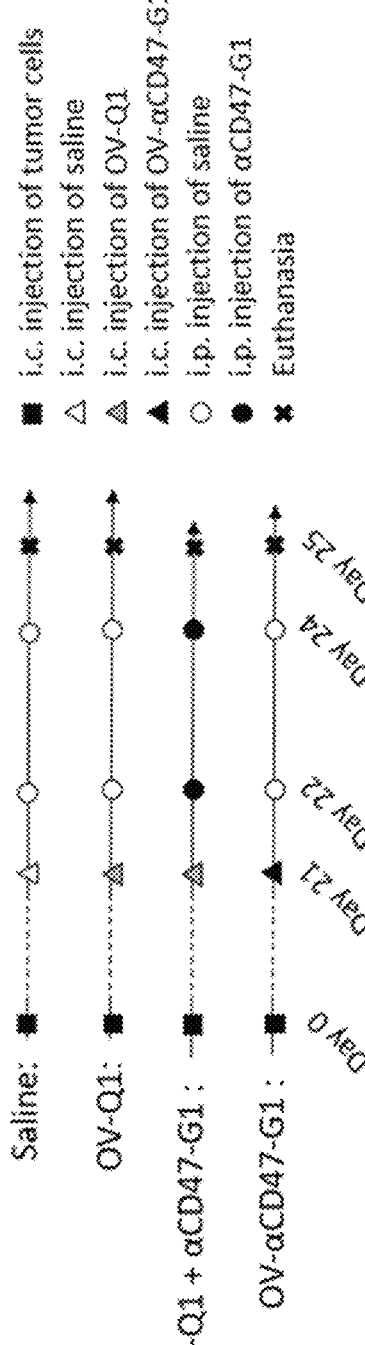

FIG. 16 shows an experimental timeline for in vivo studies using an orthotopic model of human GBM. There were four treatment groups: Group 1, saline; Group 2, OV-Q1; Group 3, a combination of OV-Q1 plus i.p. administration of αCD47-G1; and Group 4, OV-αCD47-G1. On day 0, the mice were implanted with $1\times10^5$ GBM43 cells i.c. After tumor implantation, Groups 2, 3 and 4 received intratumoral injection of oHSV (OV-Q1 or OV-αCD47-G1) at a dose of $2\times10^5$ PFU per mouse on day 21. Group 1 received saline as control. On days 22 and 24, Group 3 received i.p. injection of purified αCD47-G1 at the dose of 150 μg per mouse per day. Groups 1, 2, and 4 received i.p. injections of saline as control. All mice were euthanized on day 25 for blood and brain harvesting.

Figure 17A:
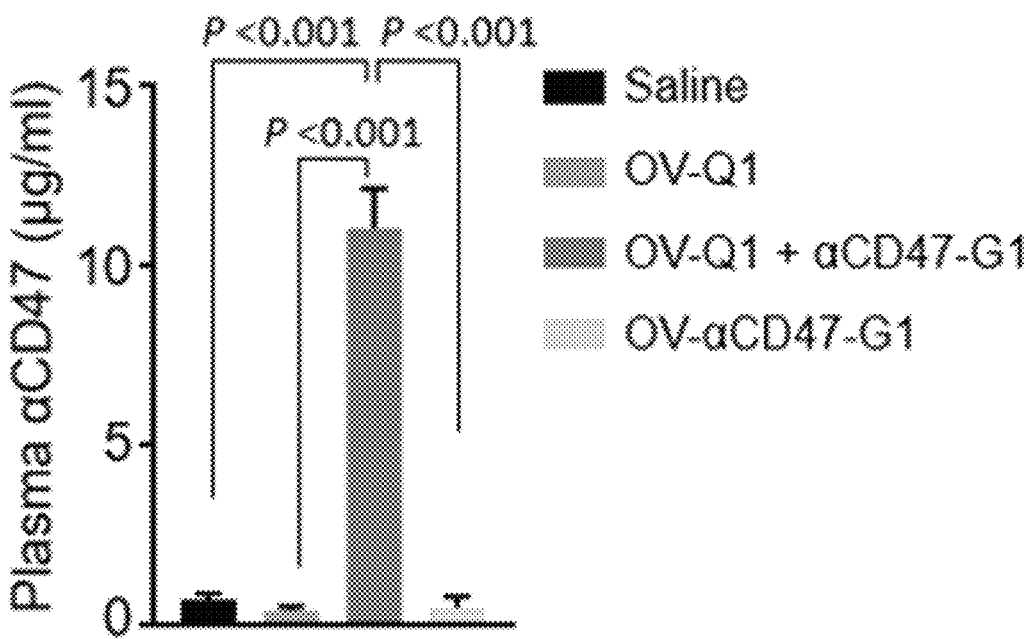
Figure 17B:
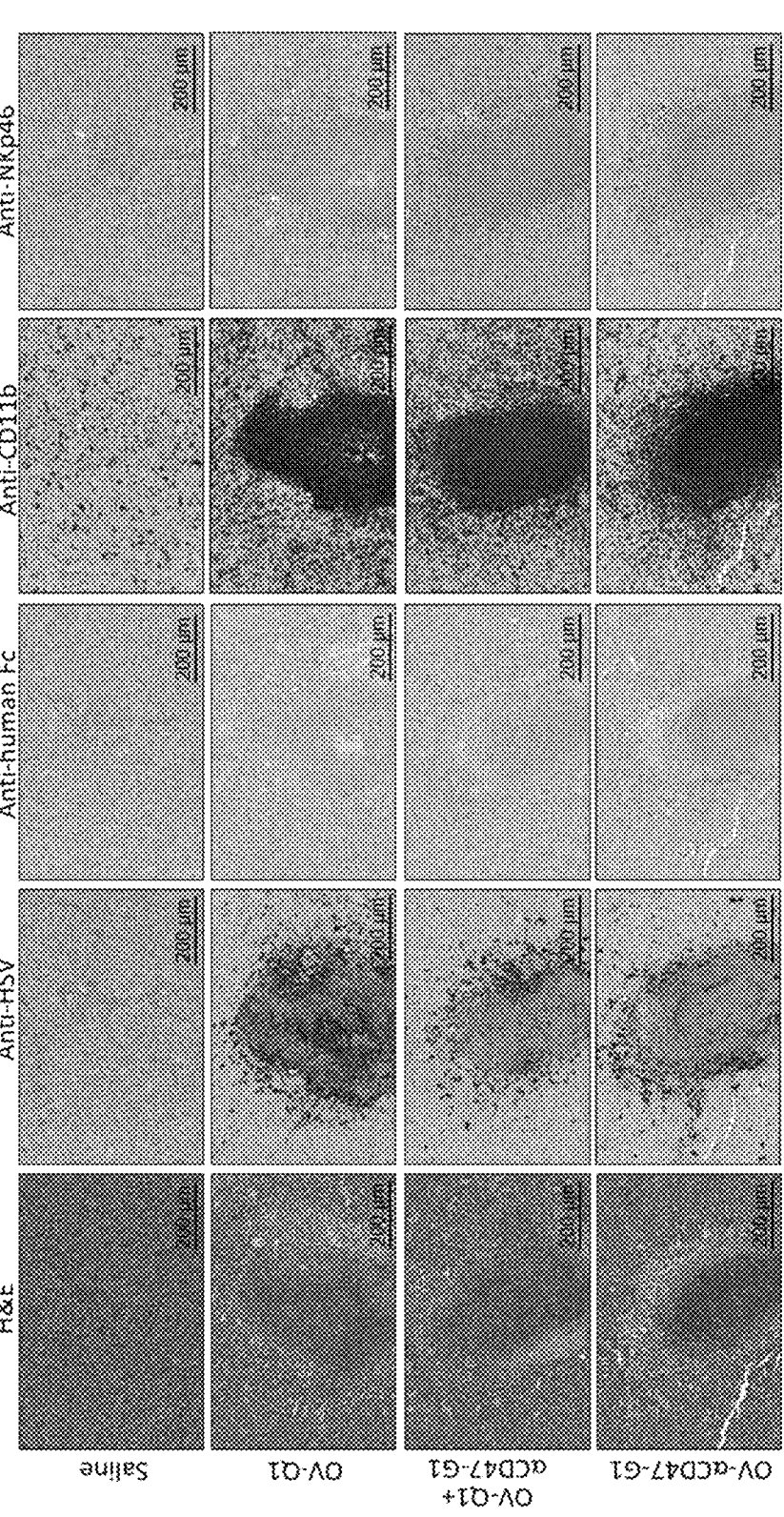
Figure 17C:
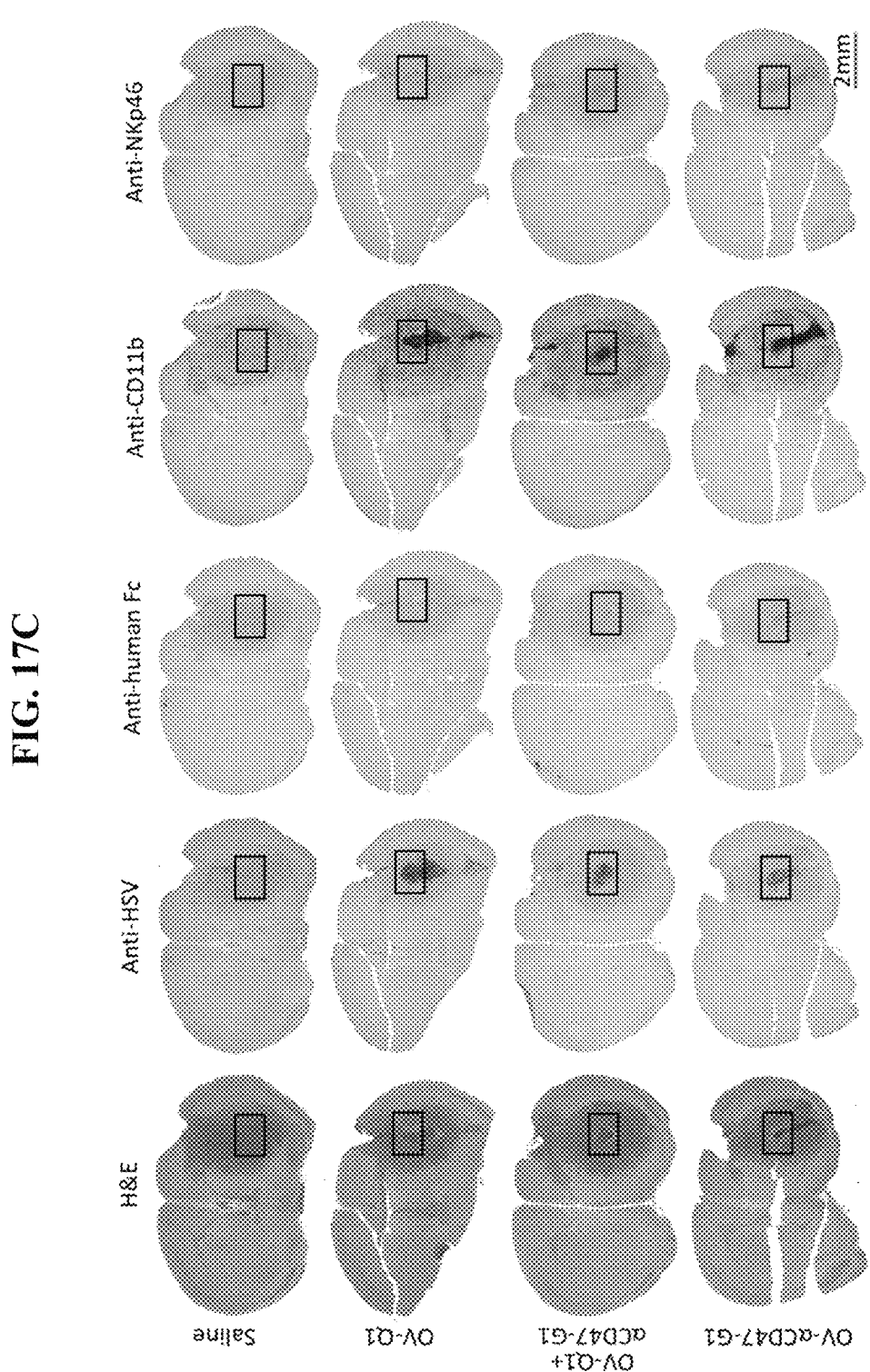

FIGS. 17A-17C shows that OV-αCD47-G1 infection continuously delivers anti-CD47 antibody to the tumor microenvironment, while systemic infusion of αCD47-G1 does not. The concentration of αCD47-G1 in plasma was measured by ELISA in mice from different treatments (FIG. 17A). The columns left to right are saline, OV-Q1, OV-Q1 plus αCD47-G1, and OV-αCD47-G1. One-way ANOVA with P values corrected for multiple comparisons by Bonferroni method multiple comparisons test (n=3 mice). (FIGS. 17B and 17C) Slides from the brains isolated from experimental mice were subjected to H&E staining and immunohistochemical staining, the latter with anti-HSV, anti-human Fc, which identifies IgG, anti-CD11b or anti-NKp46 antibodies. High and low magnifications of brain H&E and IHC with anti-HSV, anti-human Fc, anti-CD11b and anti-Nkp46 staining at the tumor implantation site are shown in C and D, respectively. The images in FIG. 17B are exactly represent high magnification of the boxed area in FIG. 17C. Data presented are represented of one (FIGS. 17B and 17C) or three (B) mice of at least three mice in total with similar data. Error bars (FIG. 17A) represent standard deviations of means of three mice.

Figure 18A:
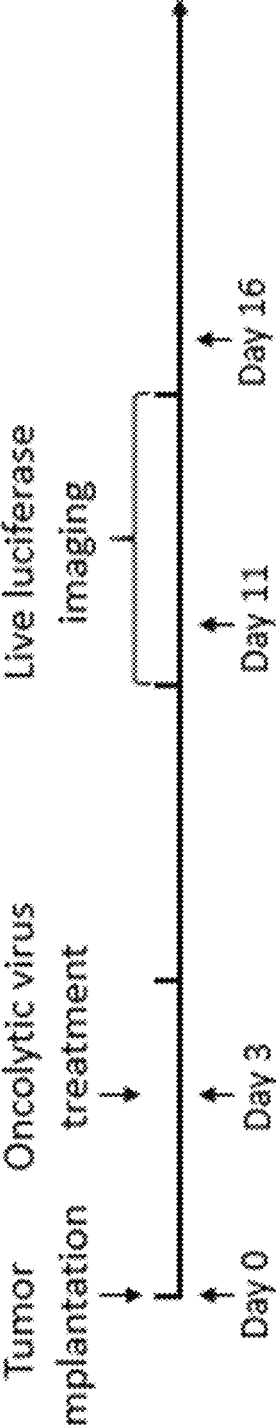
Figure 18B:
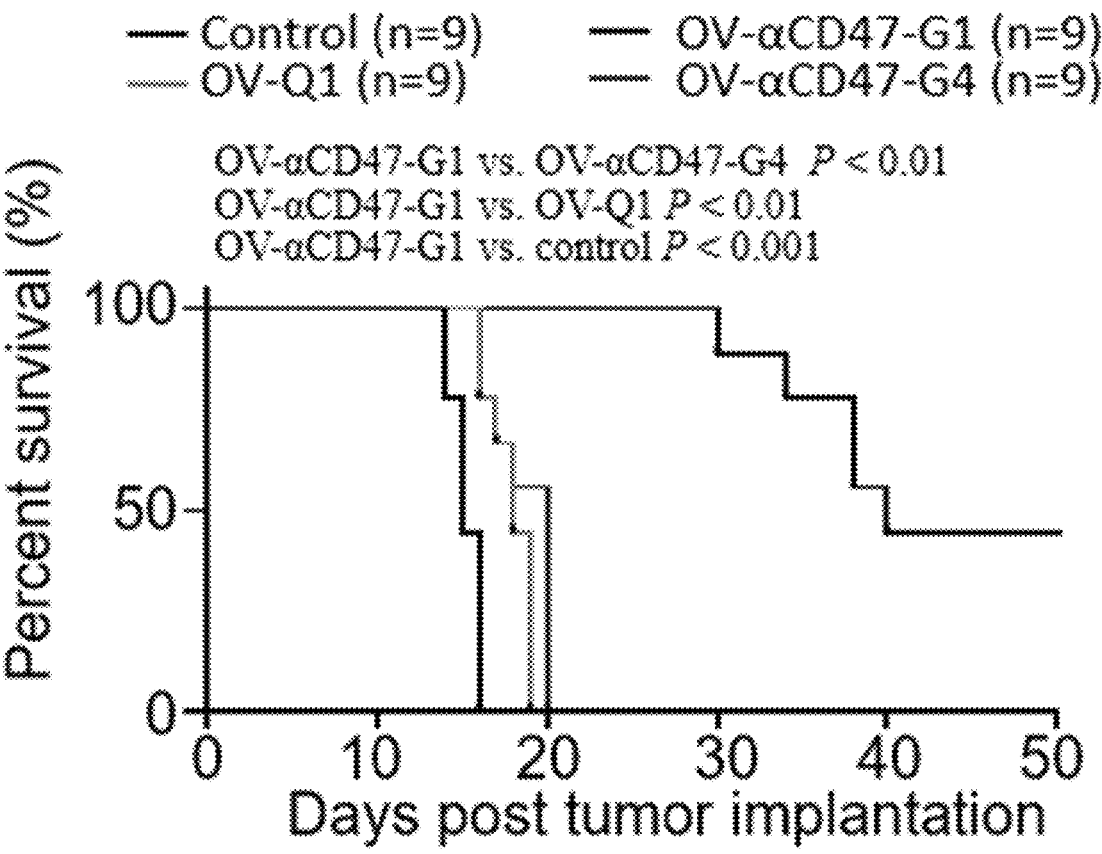
Figure 18C:
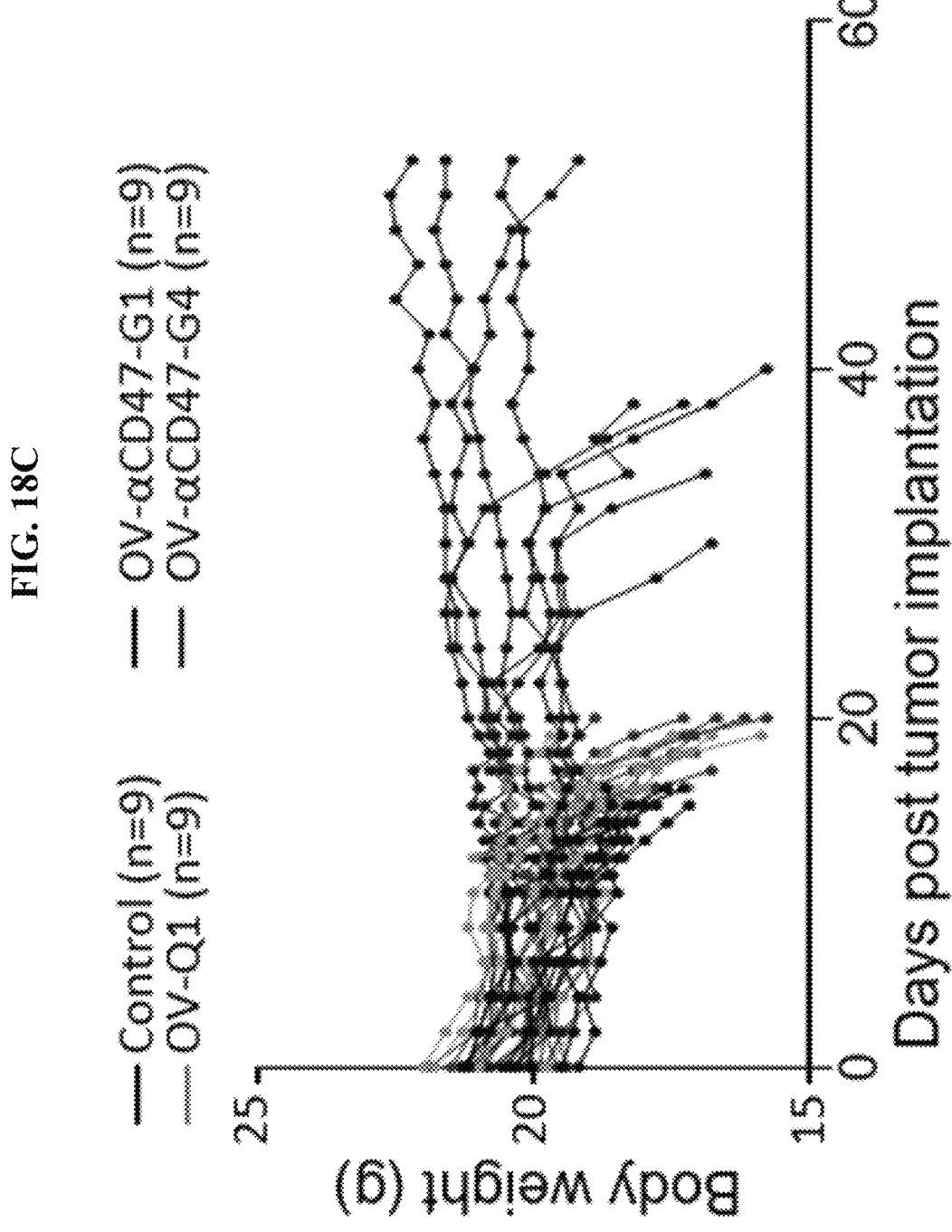
Figure 18D:
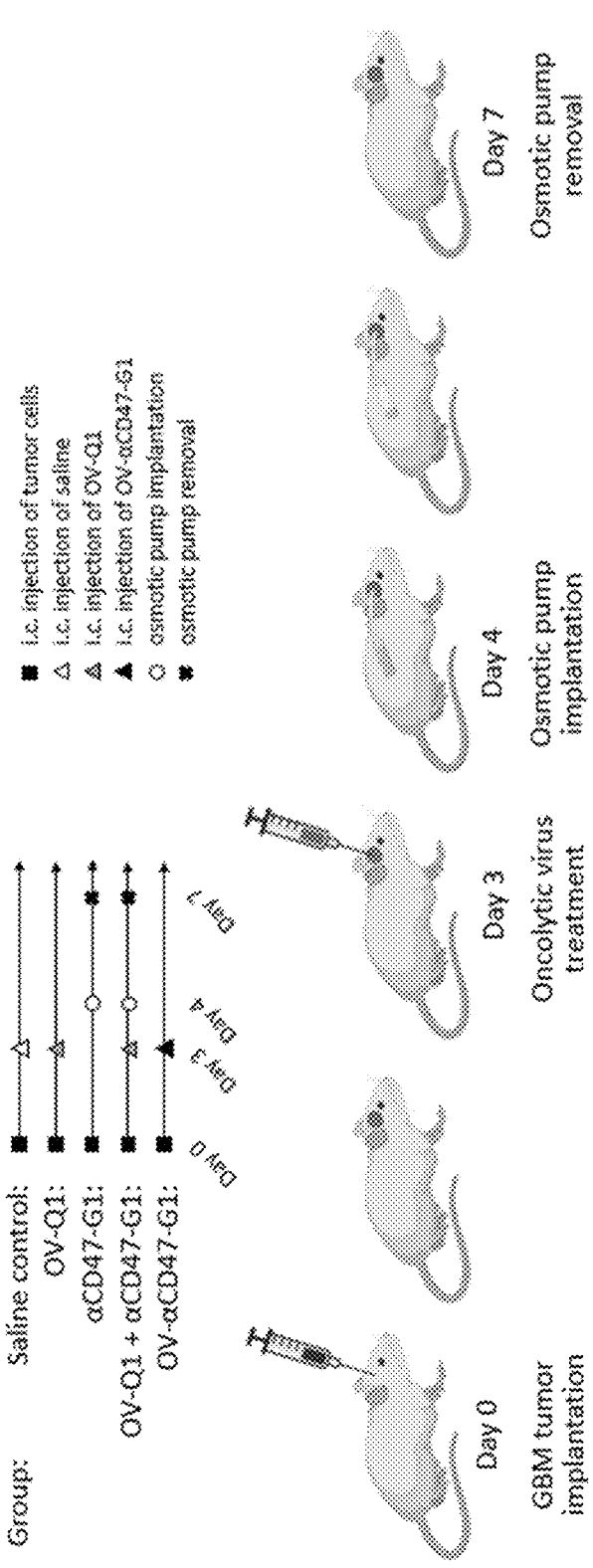
Figure 18E:
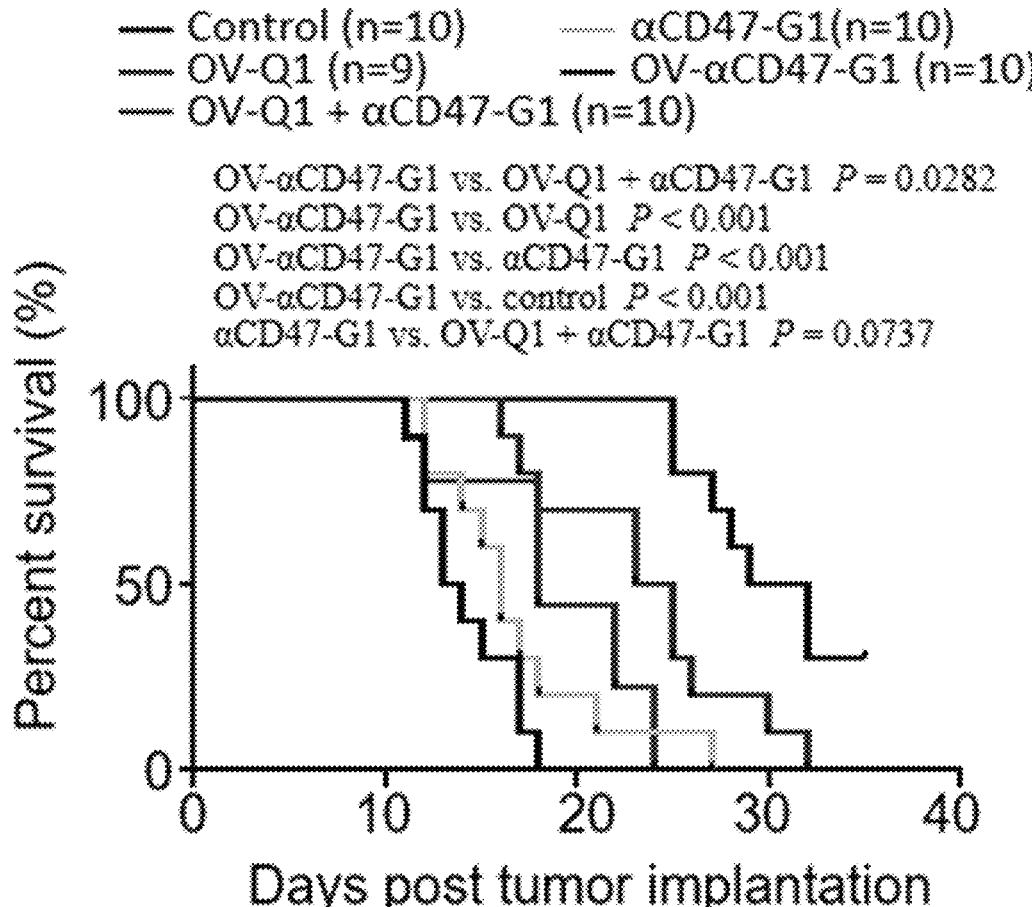

FIGS. 18A-18E show a comparison of the effectiveness of OV-αCD47-G1 versus OV-αCD47-G4 as well as combined locoregional deliveries of OV-Q1 and αCD47-G1 in an immunocompetent mouse GBM model. FIG. 18A shows an experimental timeline for in vivo studies. An immunocompetent mouse GBM model was established by i.c. injection of $1\times10^5$ CT2A-hCD47 mouse GBM cells (expressing human CD47) into C57BL/6 mice. Three days later, mice were intratumorally injected with a vehicle control or $2\times10^5$ PFU of OV-Q1, OV-αCD47-G1 or OV-αCD47-G4. Mice were weighed every other day, and luciferase-based images were taken from 11 days post tumor implantation to evaluate tumor progression. FIG. 18 B Survival of CT2A-hCD47 tumor-bearing mice as described in (A). P<0.01 for OV-αCD47-G1 vs. OV-αCD47-G4. P<0.01 for OV-αCD47-G1 vs. OV-Q1; and P<0.001 for OV-αCD47-G1 vs. control. Survival was estimated by the Kaplan-Meier method and compared by log rank test (n=9 animals). FIG. 18C shows individual body weights recorded in mice treated on the experimental study. FIG. 18D shows an experimental timeline for the survival study. An immunocompetent mouse GBM model was established by i.c. injection of $1\times10^5$ CT2A-hCD47 mouse GBM cells (expressing human CD47) into C57BL/6 mice. Three days later, mice were intratumorally injected with vehicle control or $2\times10^1$ PFU of OV-Q1, or OV-αCD47-G1. Osmotic pumps were implanted on day 4 to the mice for continuous administration of αCD47-G1 until day 7. Mice were monitored twice a day to evaluate for tumor development. FIG. 18E shows survival of CT2A-hCD47 tumor-bearing mice treated with OV-Q1, αCD47-G1, OV-Q1 plus αCD47-G1, OV-αCD47-G1, or vehicle control. Survival was estimated by the Kaplan-Meier method and compared by log rank test (n=9 or 10 animals per group).

Figure 19:
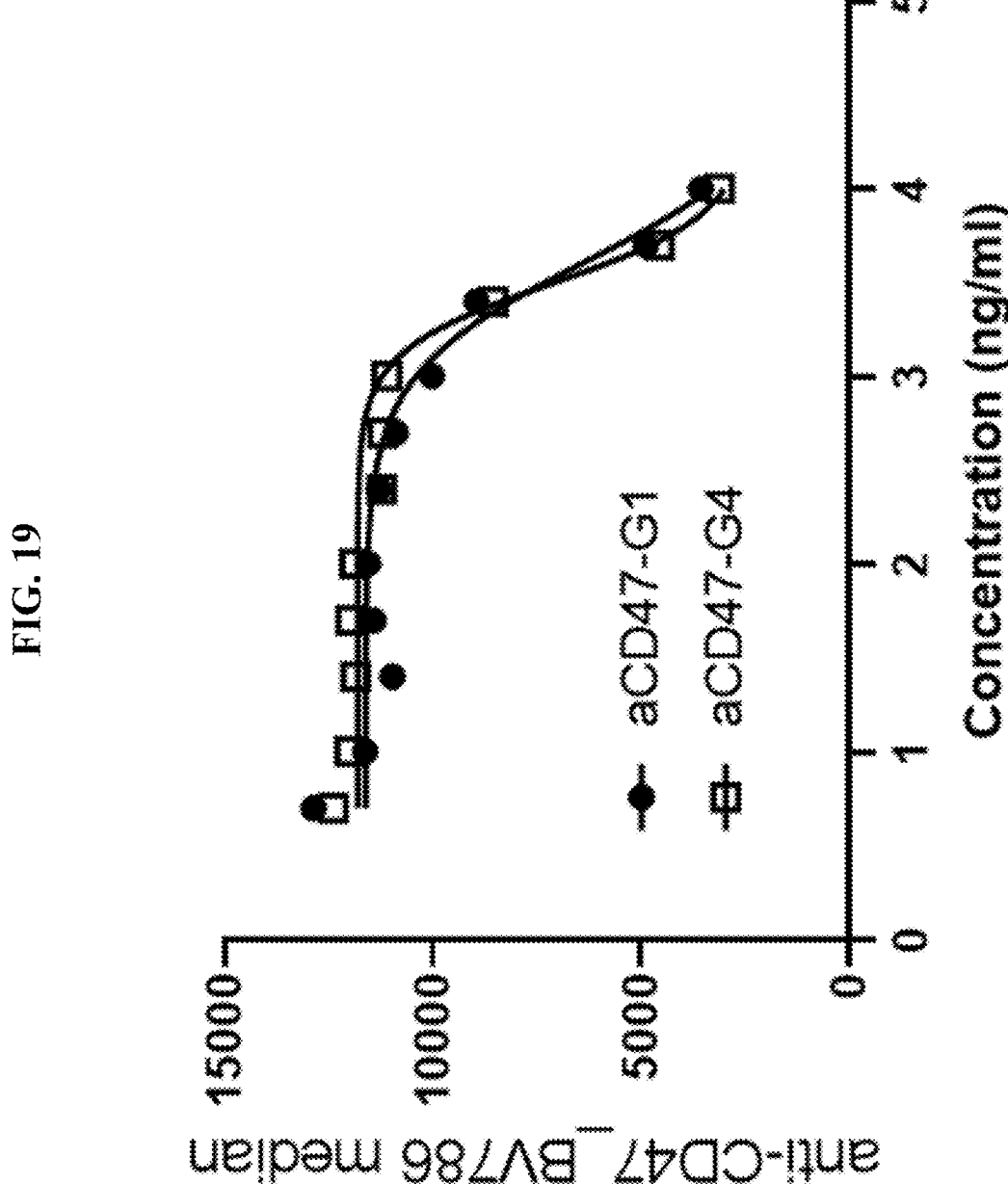

FIG. 19 shows characterization of OV-Q1, OV-αCD47-G1 and OV-αCD47-G4. A2780 cells were incubated with different concentrations of unlabeled αCD47-G1 or αCD47-G4 mAb followed by incubation with a conjugated anti-human CD47 and assessed by flow cytometry.

Figure 20:
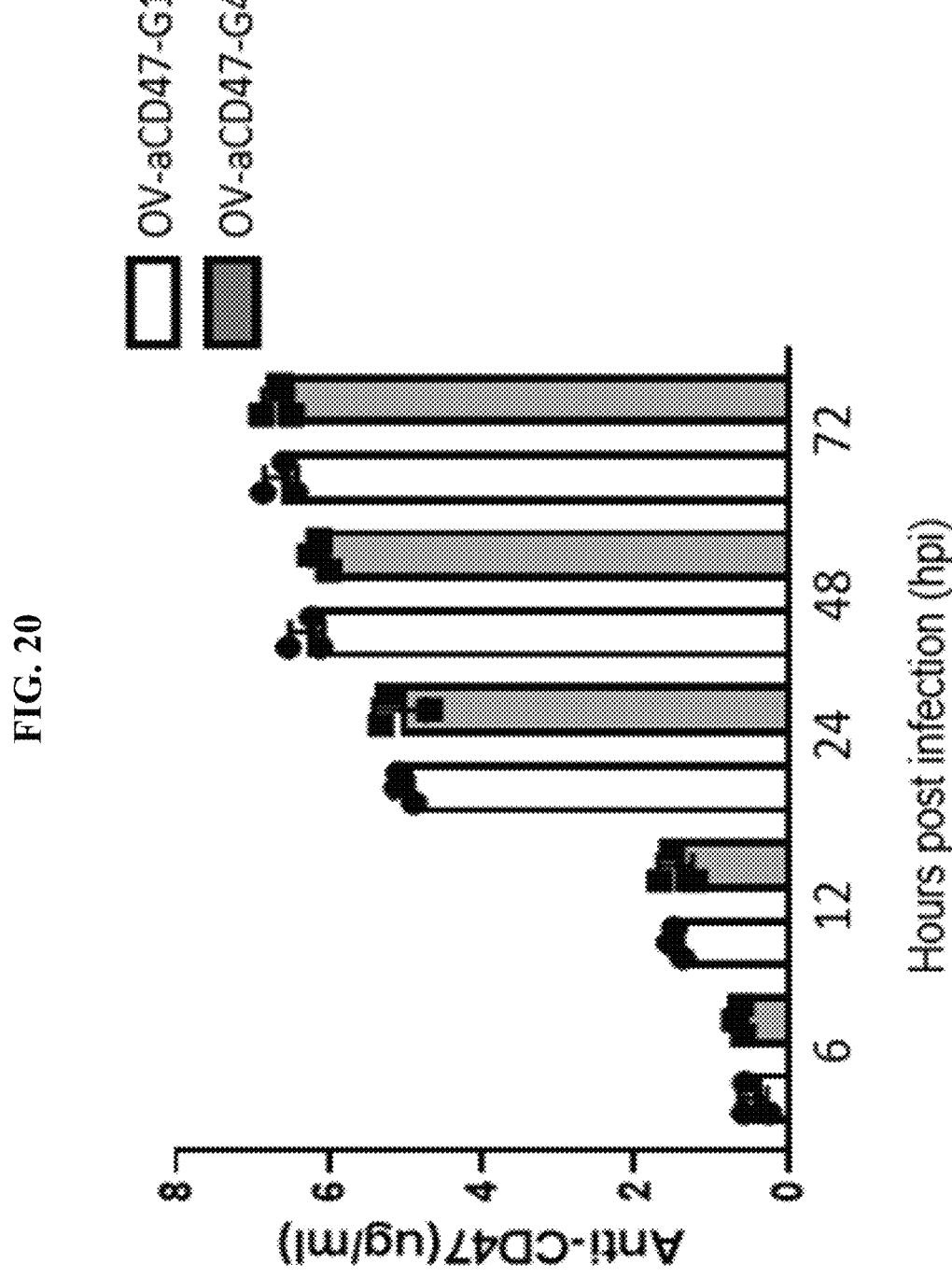

FIG. 20 shows αCD47-G1 and αCD47-G4 yields from supernatants of OV-αCD47-G1- and OV-αCD47-G4-infected A2780 cells as determined by ELISA assay.

Figure 21A:
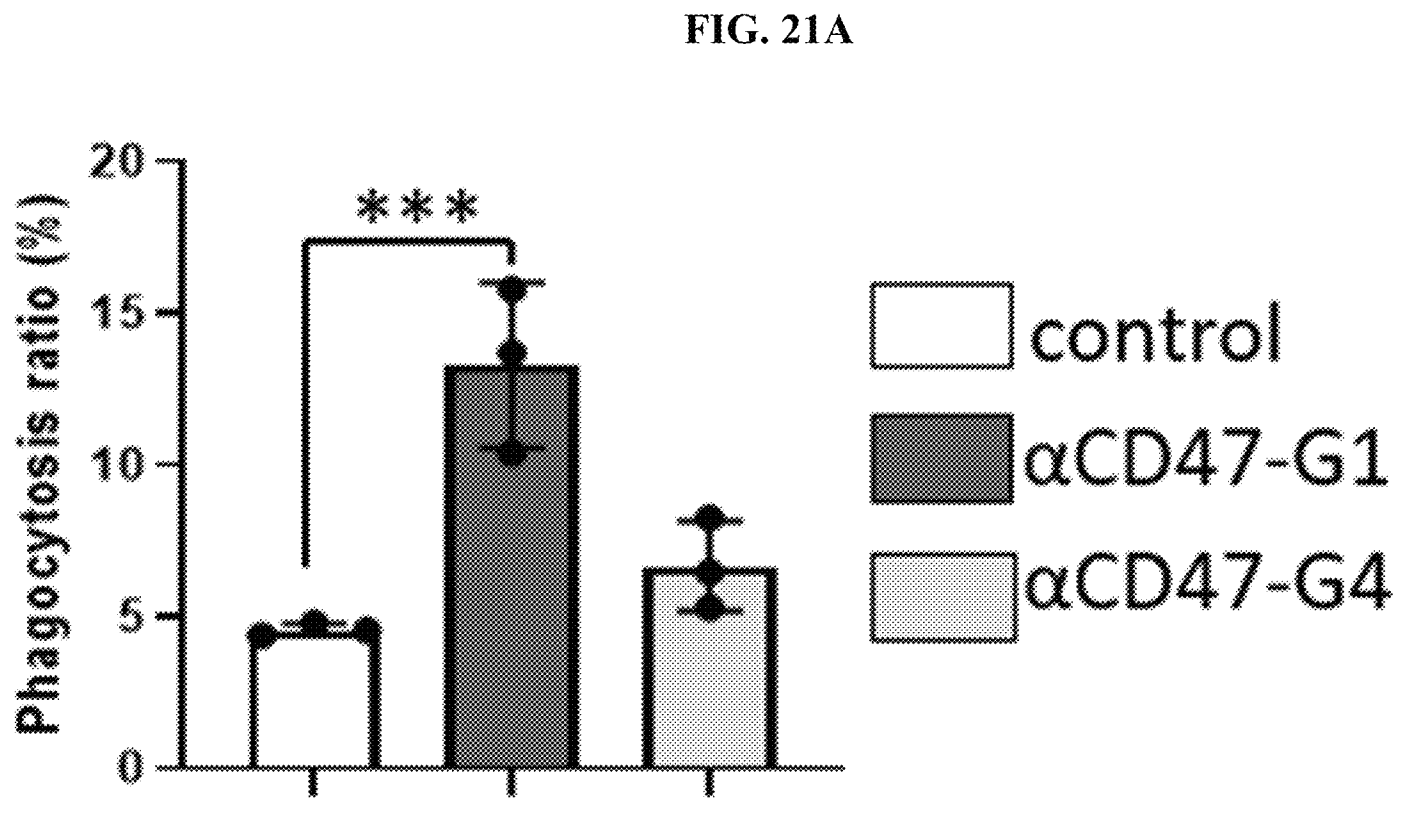
Figure 21B:
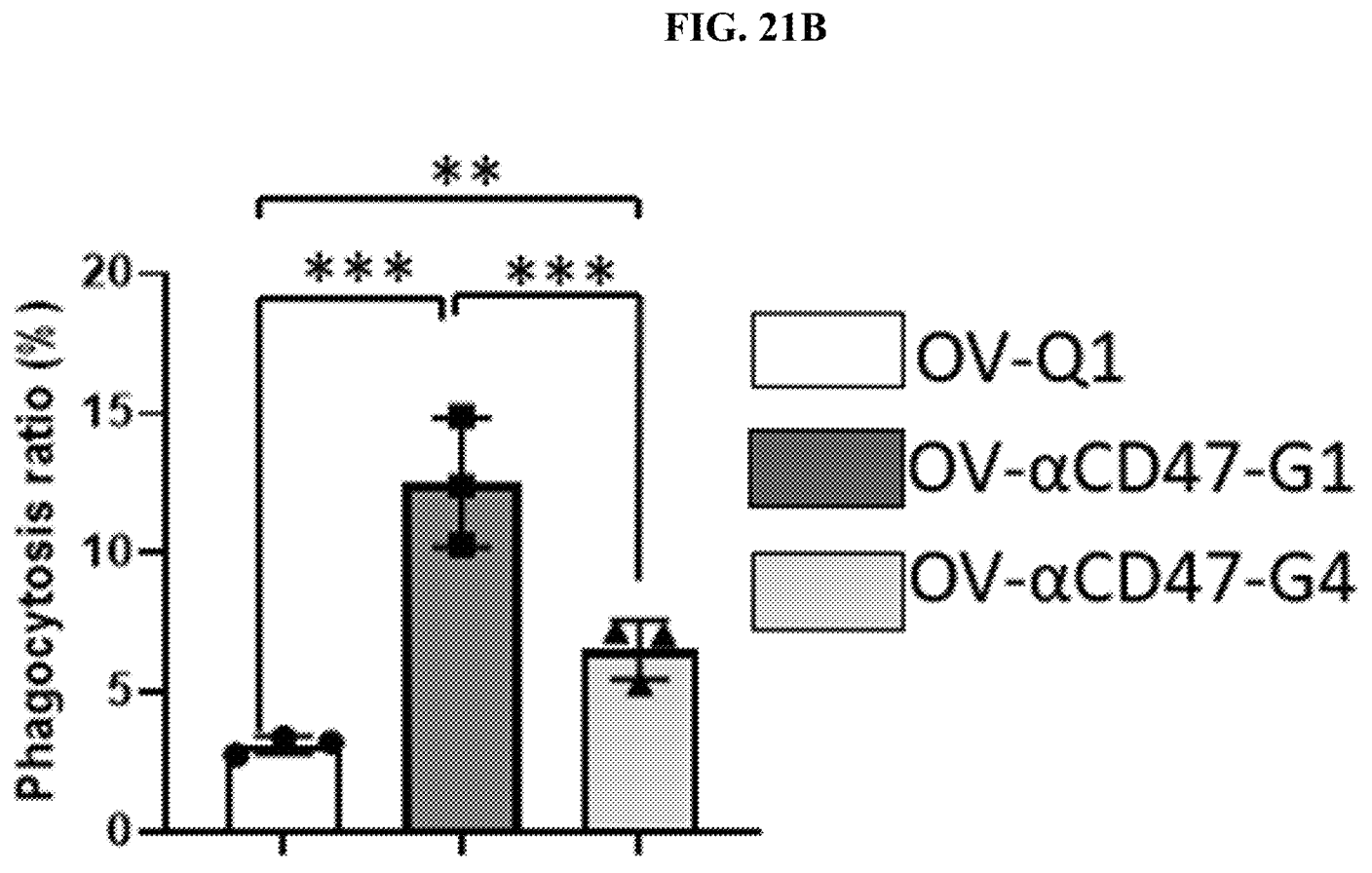
Figure 21C:
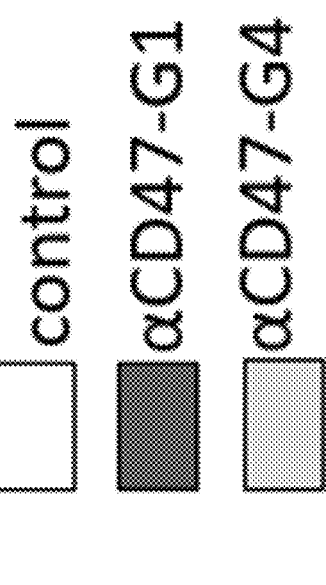
Figure 21D:
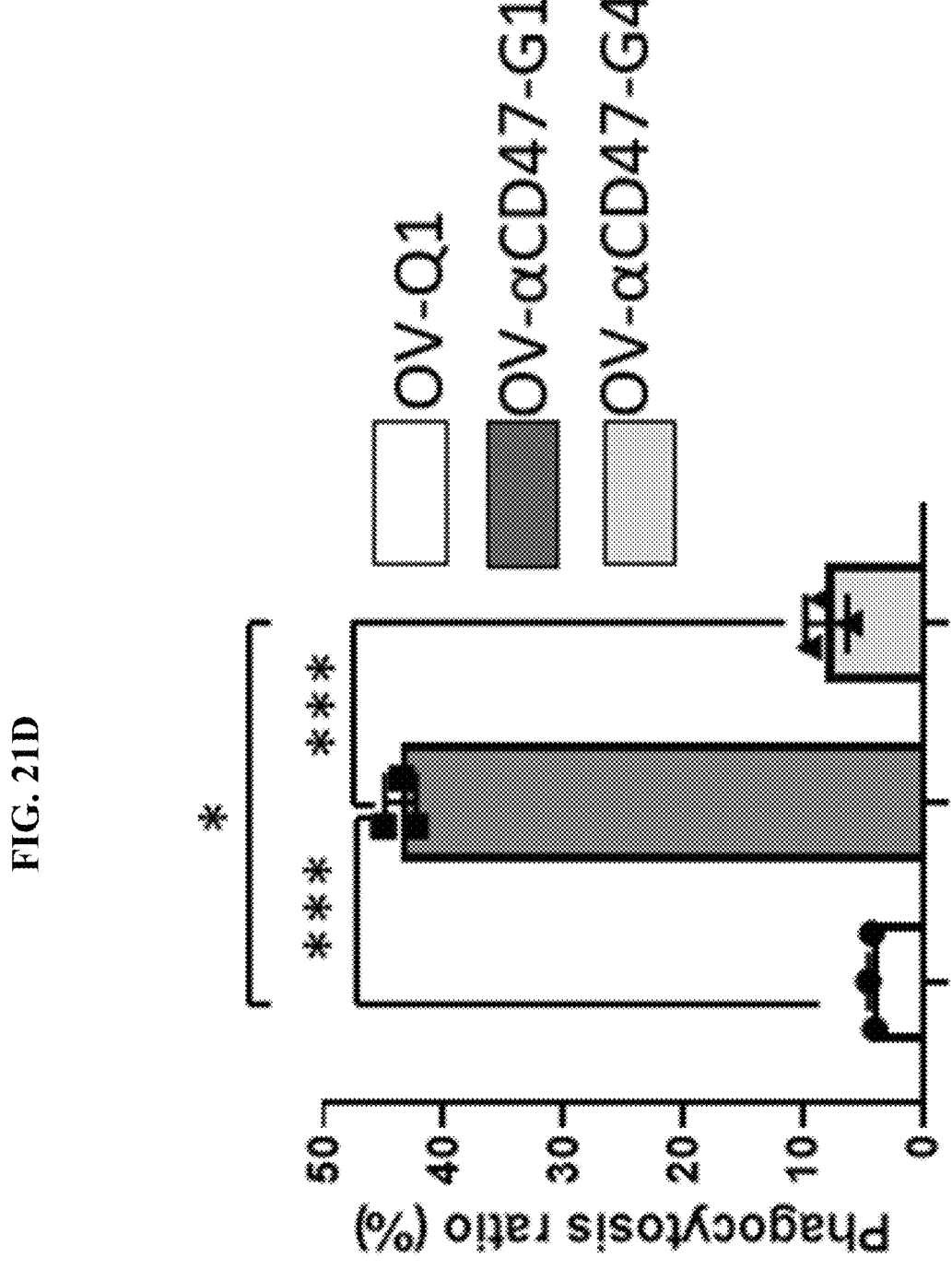

FIGS. 21A-21D shows αCD47-G1 and αCD47-G4 induce phagocytosis of A2780 ovarian cells. FIG. 21A shows the effect of 5 µg/ml of αCD47-G1 and αCD47-G4 purified from CHO cells on phagocytosis of A2780 cells by primary human macrophages. FIG. 21B shows conditional media from OV-αCD47-G1- and OV-αCD47-G4-infected A2780 cells induce phagocytosis against A2780 cells by primary human macrophages. Phagocytosis was assayed by flow cytometry. FIG. 21C shows the effect of 5 µg/ml of αCD47-G1 and αCD47-G4 purified from CHO cells on phagocytosis of A2780 cells by BMDMs. Percentage of BMDM phagocytosis of A2780 cells (CD11b+CFSE+) was assayed by flow cytometry. FIG. 21D shows conditional media from OV-αCD47-G1- and OV-αCD47-G4-infected A2780 cells induce phagocytosis against A2780 cells by BMDMs. Phagocytosis was assayed by flow cytometry.

Figure 22A:
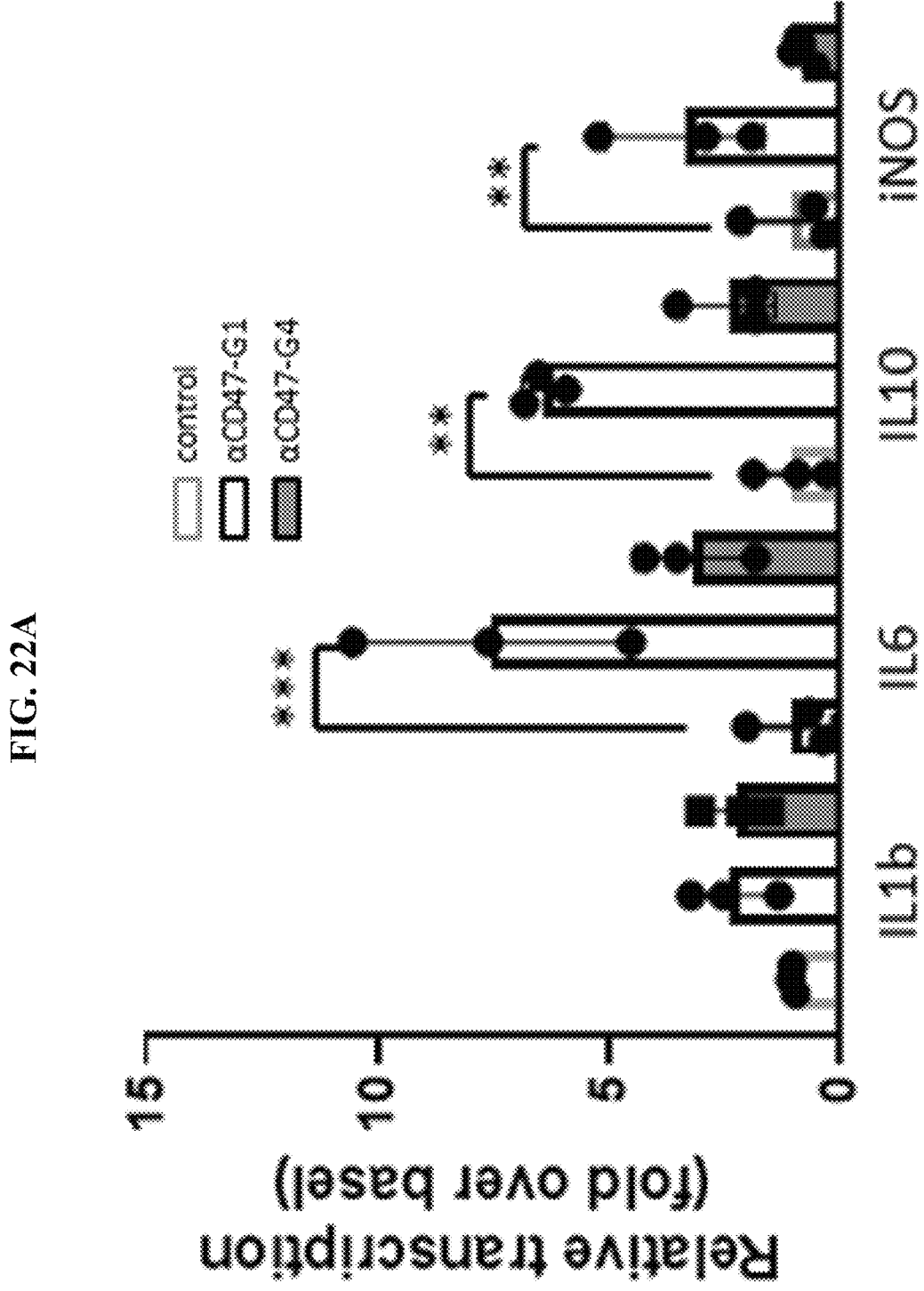
Figure 22B:
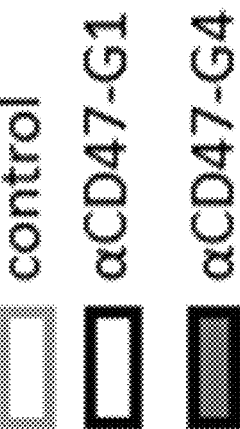
Figure 22B:
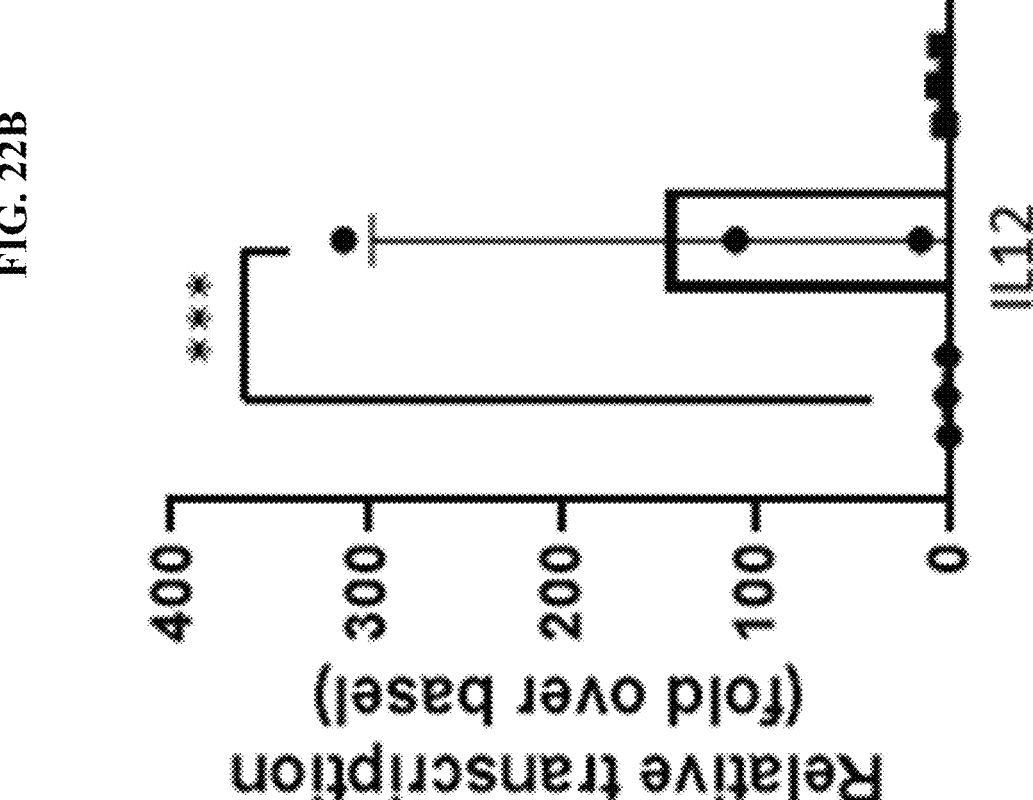

FIGS. 22A-22B show transcription assays. Primary human macrophages were cocultured with A2780 cells at a ratio of 1:1 with or without αCD47-G1 or αCD47-G4 for 6 hours after which gene transcripts were quantified. FIG. 22A shows expression levels of IL1b, IL6, IL10, and INOS. FIG. 22B shows expression levels of IL12. All experiments were performed at least with three human donors or mice. Error bars represent standard deviations of triplicates.

Figure 23A:
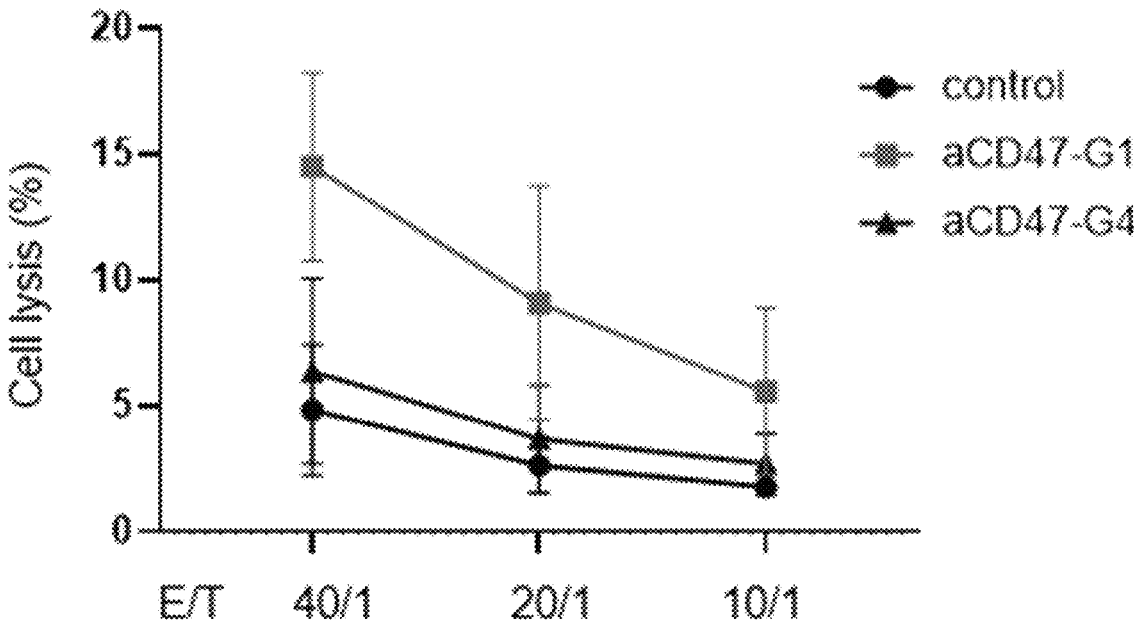
Figure 23B:
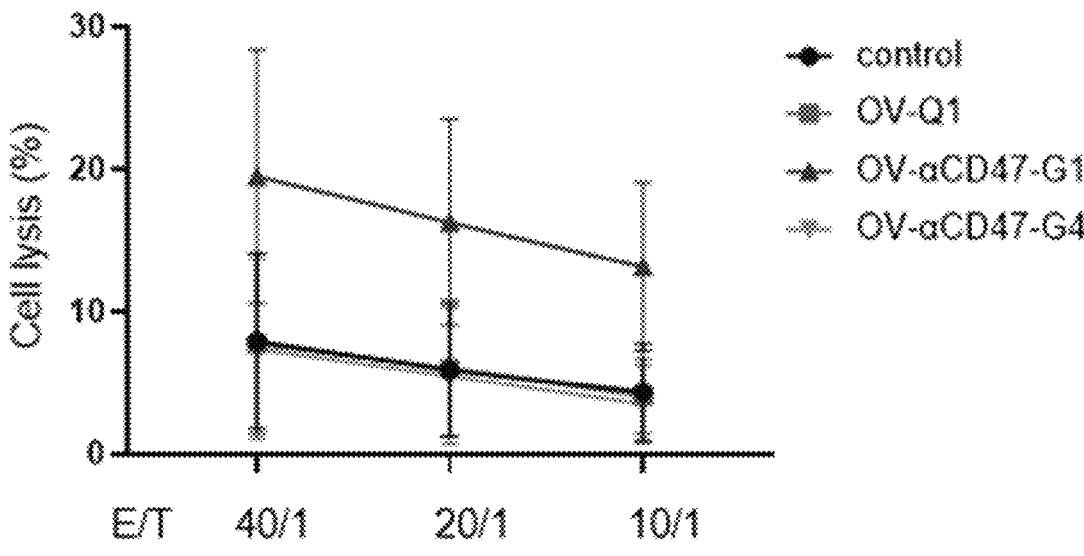
Figure 23C:
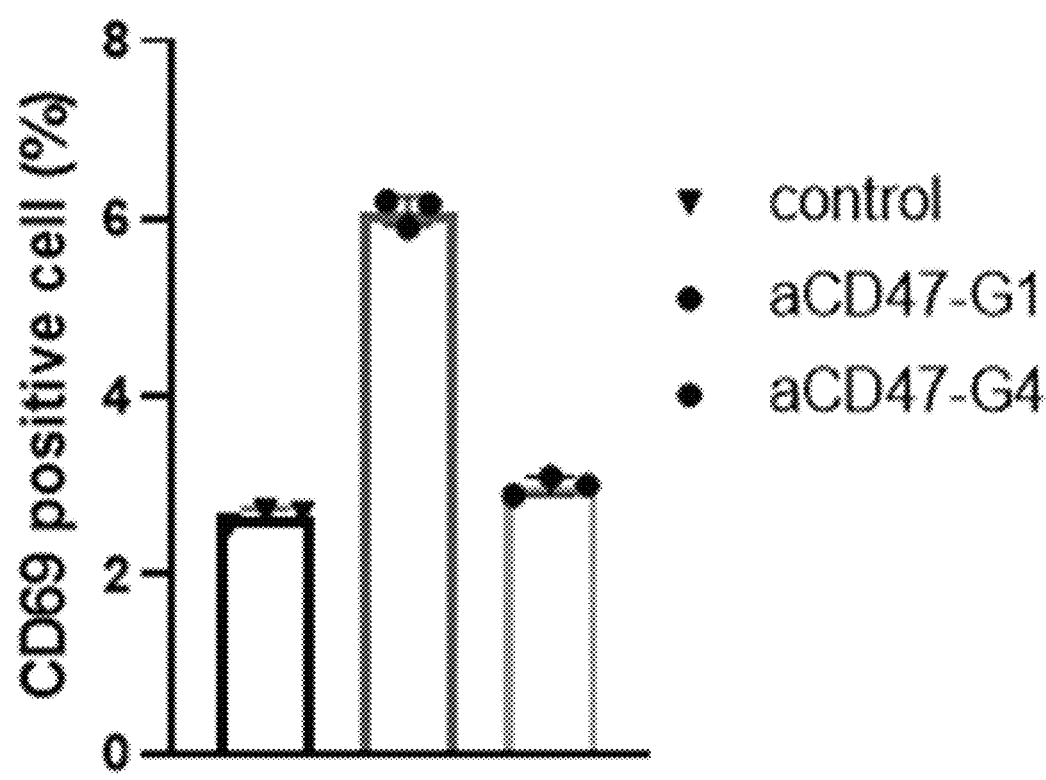
Figure 23D:
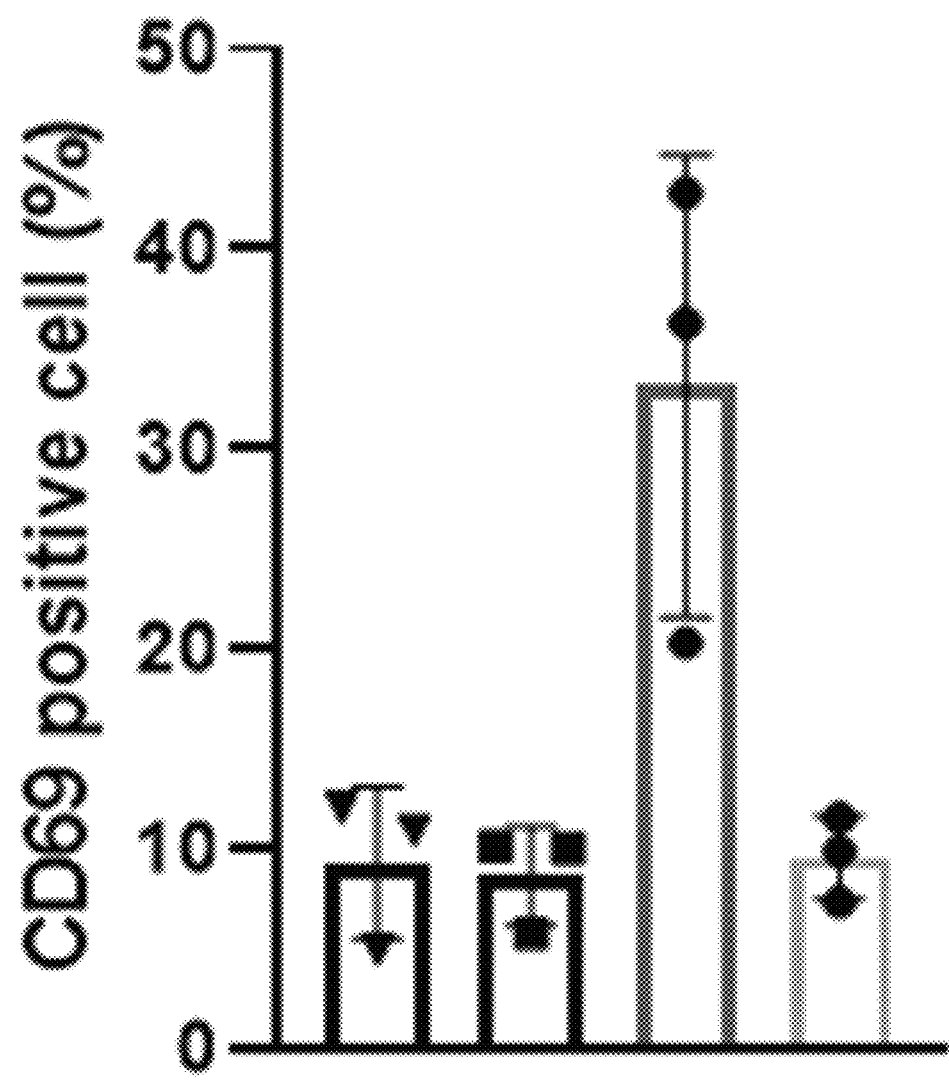
Figure 23E:
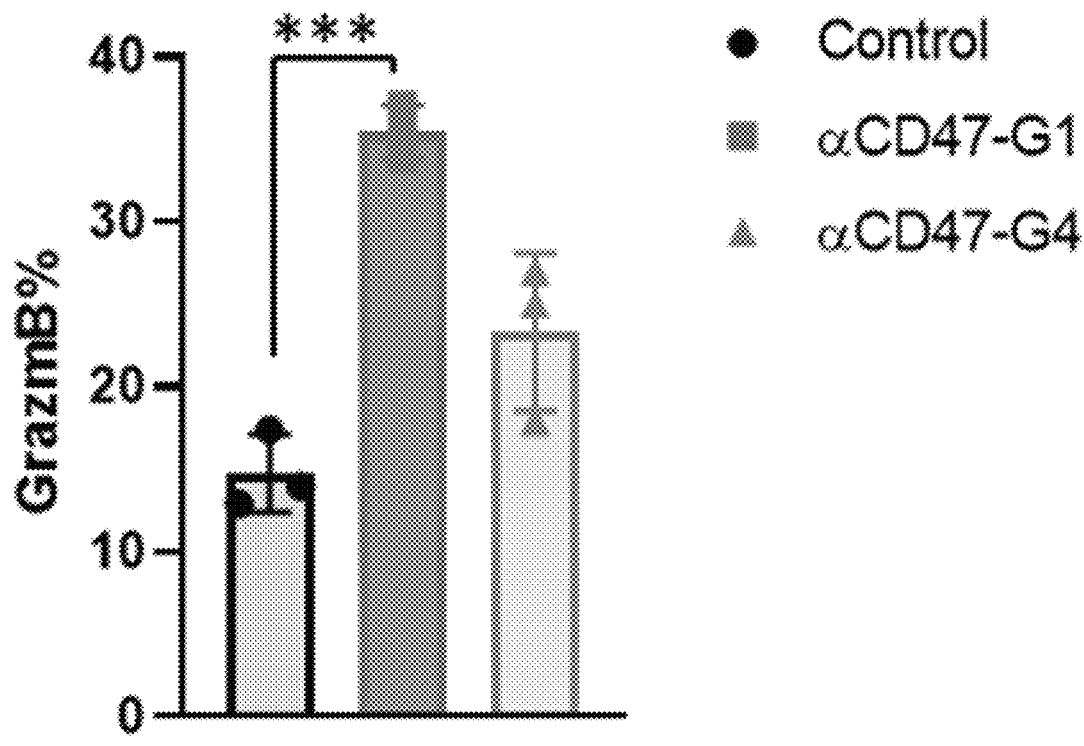

FIGS. 23A-23E show that αCD47-G1 but not αCD47-G4 induces cytotoxicity of human NK cells against ovarian cells. FIG. 23 A shows cytotoxicity of human primary NK cells against αCD47-G1- and αCD47-G4-treated A2780 human ovarian cells. FIG. 23B shows cytotoxicity of human primary NK cells against A2780 cells that were treated with conditional media from OV-Q1-, OV-αCD47-G1- or OV-αCD47-G4-infected A2780 cells. FIG. 23 C shows CD69 expression of NK cells when co-cultured with A2780 cells that were pretreated with αCD47-G1 or αCD47-G4 detected by flow cytometry (columns left to right are control, αCD47-G1, and αCD47-G4). FIG. 23 D shows CD69 expression of NK cells when co-cultured with A2780 cells with conditional media from uninfected, OV-Q1-, OV-αCD47-G1- or OV-αCD47-G4-infected A2780 cells detected by flow cytometry (columns left to right are uninfected, OV-Q1-infected, OV-αCD47-G1-infected, and OV-αCD47-G4-infected). FIG. 23E shows Granzyme b production by NK cells when co-cultured with A2780 cells that were pretreated with αCD47-G1 or αCD47-G4 detected by flow cytometry. All experiments were performed with three donors in triplicate. Error bars represent standard deviations of means of three donors.

Figure 24:
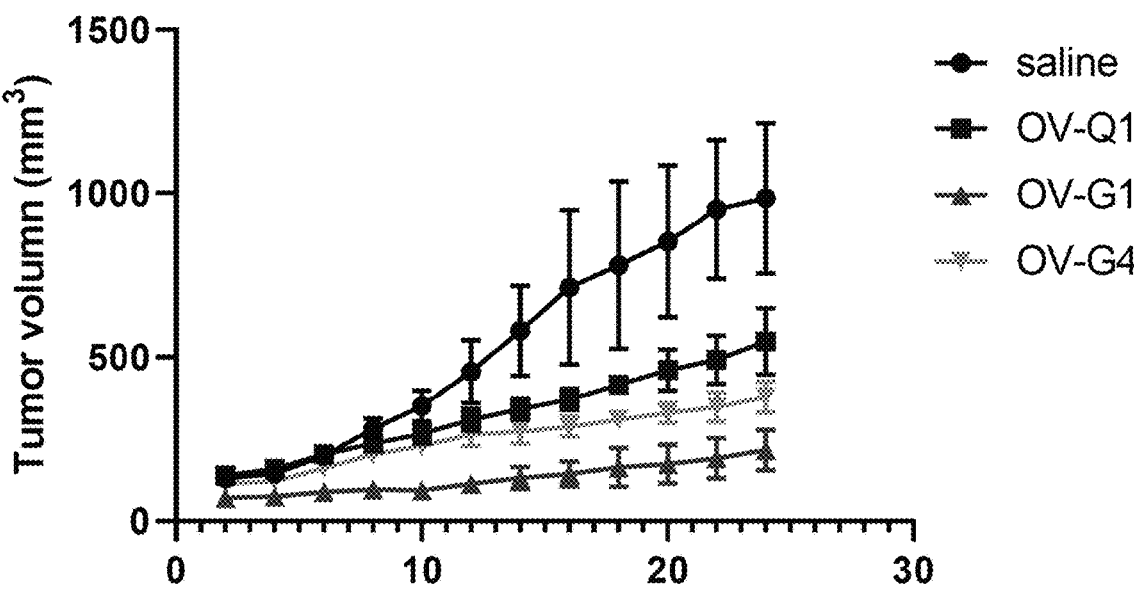

FIG. 24 shows OV-αCD47-G1 improves the therapeutic efficacy against ovarian tumor. An orthotopic model of human ovarian tumor was established by s.c. injection of $5\times10^6$ A2780 cells. One day later, mice were intratumorally injected with a vehicle control or $1\times10^5$ PFU of OV-Q1, OV-αCD47-G1, or OV-αCD47-G4. FIG. 24 shows tumor volume of ovarian tumor growth in mice with indicated treatments. X-axis shows days post-implantation.

Figure 25:
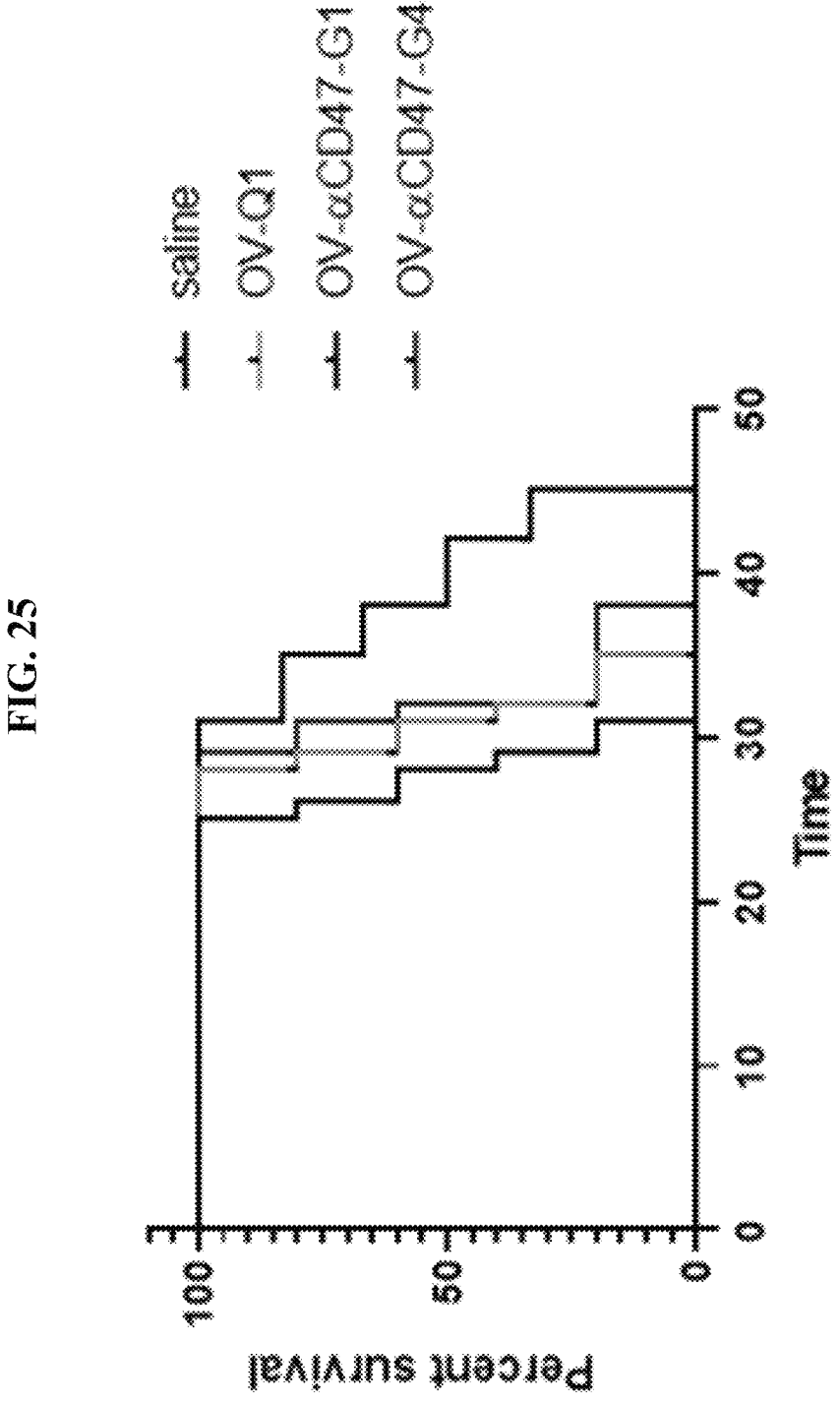

FIG. 25 shows OV-αCD47-G1 enhances the therapeutic efficacy (percent survival) in an immunocompetent ovarian cancer mouse model. X-axis shows days post tumor implantation.

Figure 26:
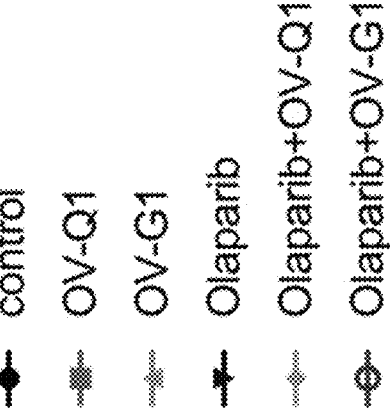
Figure 26:
Figure 26:
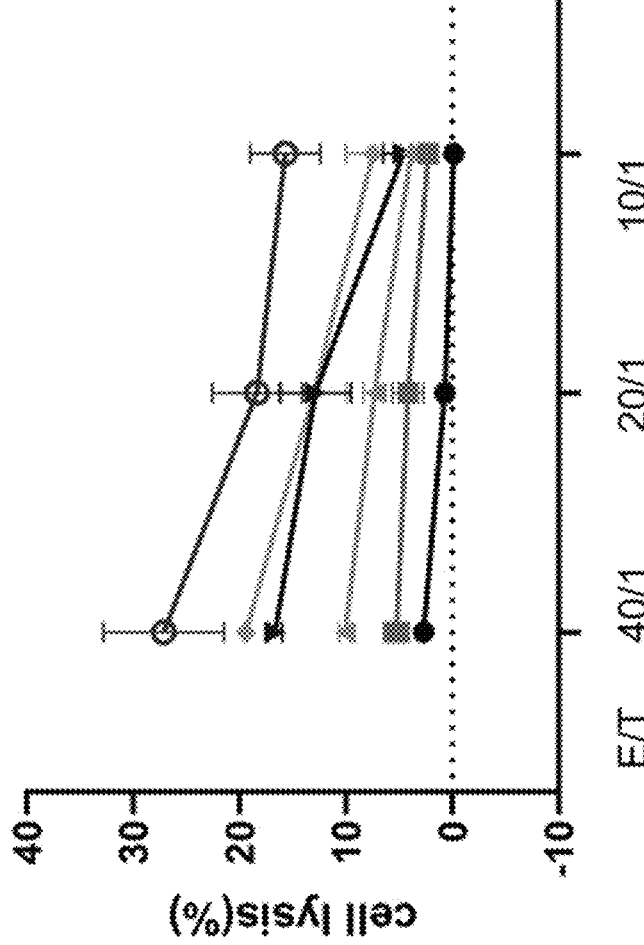

FIG. 26 shows an enhanced effect in vitro and in vivo for the combination of OV-αCD47-G1 with olaparib.

DETAILED DESCRIPTION

Provided herein are, inter alia, recombinant oncolytic viruses expressing an anti-CD47 antibody and methods for the treatment of cancer, immune disorders, and infectious disease.

I. Definitions

Before the present invention is further described, it is to be understood that this invention is not strictly limited to particular embodiments described, and as such may of course vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It should further be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly the terms "comprising", "including" and "having" can be used interchangeably.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

The terms "virus" or "virus particle" are used according to its plain ordinary meaning within virology and refers to a virion including the viral genome (e.g. DNA, RNA, single strand, double strand), viral capsid and associated proteins, and in the case of enveloped viruses (e.g. herpesvirus), an envelope including lipids and optionally components of host cell membranes, and/or viral proteins.

The term "replicate" is used in accordance with its plain ordinary meaning and refers to the ability of a cell or virus to produce progeny. A person of ordinary skill in the art will immediately understand that the term replicate when used in connection with DNA, refers to the biological process of producing two identical replicas of DNA from one original DNA molecule. In the context of a virus, the term "replicate" includes the ability of a virus to replicate (duplicate the viral genome and packaging said genome into viral particles) in a host cell and subsequently release progeny viruses from the host cell, which results in the lysis of the host cell. A "replication-competent" virus as provided herein refers to a virus (herpes virus) that is capable of replicating in a cell (e.g., a cancer cell).

As used herein, the term "oncolytic virus" is used in accordance with its plain ordinary meaning and refers to a virus that preferentially infects and kills cancer cells. As the infected cancer cells are destroyed by oncolysis (directly lysing cells), they release new infectious virus particles or virions to help destroy the remaining tumor. Oncolytic viruses are thought not only to cause direct destruction of the tumor cells, but also to stimulate host anti-tumor immune system responses. Oncolytic viruses include adenovirus, reovirus, measles, herpes simplex, Newcastle disease virus, vaccinia, and the senecavirus.

As used herein, the term "recombinant virus" is a virus produced by recombining pieces of nucleic acid (e.g. DNA) using recombinant nucleic acid technology. A "recombinant oncolytic virus" is an concolytic virus produced by recombining pieces of nucleic acid (e.g. DNA) using recombinant nucleic acid technology.

As used herein, the term "herpes simplex virus" or "HSV" refers to members of the Herpesviridae family. Herpes simplex virus 1 and 2 (HSV-1 and HSV-2), also known by their taxonomical names Human alphaherpesvirus 1 and Human alphaherpesvirus 2, are two members of the human Herpesviridae family, a set of viruses that produce viral infections in the majority of humans.

As used herein, the term "γ34.5 gene" or "gamma-34.5 gene" is used in accordance with its plain ordinary meaning and refers to a herpes simplex virus neurovirulence gene.

As used herein, the term "ICP6" or "ICP6 gene" is used in accordance with its plain ordinary meaning and refers to a gene that encodes a viral ribonucleotide reductase (vRR).

As used herein, the term "cancer" is used in accordance with its plain ordinary meaning and refers to all types of cancer, neoplasm or malignant tumors found in mammals (e.g. humans), including leukemias, lymphomas, carcinomas and sarcomas. Examples of cancers that may be treated with a compound, composition, or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is glioblastoma, ovarian cancer, pancreatic cancer, myeloma, leukemia, or lymphoma.

The term "leukemia" is used in accordance with its plain ordinary meaning and refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Examples of leukemias that may be treated with a compound or method provided herein include, for example, acute non-lymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, mia, stem cell leukemia, subleukemic leukemia, or undifferentiated cell leukemia. In embodiments, the cancer is acute myeloid leukemia.

The term "chronic inflammatory cancer" is used in accordance with its plain ordinary meaning and refers broadly to as used herein, relates to its usual an customary meaning of a cancer related to a chronic inflammatory condition. Chronic inflammatory conditions related to cancers include, but are not limited to, those provided in the table below.

TABLE 1

| Chronic inflammatory conditions associated with neoplasms | | |
| --- | --- | --- |
| Pathologic condition | Associated neoplasm(s) | Aetiologic agent |
| Asbestosis, silicosis | Mesothelioma, lung carcinoma | Asbestos fibres, silica particles |
| Bronchitis | Lung carcinoma | Silica, asbestos, smoking (nitrosamines, peroxides) |
| Cystitis, bladder inflammation | Bladder carcinoma | Chronic indwelling, urinary catheters |
| Gingivitis, lichen planus | Oral squamous cell carcinoma | |
| Inflammatory bowel disease, Crohn's disease, chronic ulcerative colitis | Colorectal carcinoma | |
| Lichen sclerosus | Vulvar squamous cell carcinoma | |
| Chronic pancreatitis, hereditary pancreatitis | Pancreatic carcinoma | Alcholism, mutation in trypsinogen gene on Ch. 7 |
| Reflux oesophagitis, Barrett's oesophagus | Oesophageal carcinoma | Gastric acids |
| Sialadenitis | Salivary gland carcinoma | |
| Sjögren syndrome, Hashimoto's thyroiditis | MALT lymphoma | |
| Skin inflammation | Melanoma | Ultraviolet light |
| Cancers associated with infectious agents | | |
| Opisthorchis, Cholangitis | Cholangiosarcoma, colon carcnoma | Liver flukes (Opisthorchis viverrini), bile acids |
| Chronic cholecystitis | Gall bladder cancer | Bacteria, gall bladder stones |
| Gastritis/ulcers | Gastric adenocarcinoma, MALT | Helicobacter pylori |
| Hepatitis | Hepatocellular carcinoma | Hepatitis B and/or C virus |
| Mononucleosis | B-cell non-Hodgkin's lymphoma, Burkitts lymphoma | Epstein-Barr Virus |
| AIDS | Non-Hodgkin's lymphoma, squamous cell carcinomas, Kaposi's sarcoma | Human immunodeficiency virus, human herpesvirus type 8 |
| Osteomyelitis | Skin carcinoma in draining sinuses | Bacterial infection |
| Pelvic inflammatory disease, chronic cervicitis | Ovarian carcinoma, cervical/anal carcinoma | Gonnorrhoea, chlamydia, human papillomavirus |
| Chronic cystitis | Bladder, liver, rectal carcinoma, follicular lymphoma of the spleen | Schistosomiasis | blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leuke- An "overactive immune system" is used in accordance with its plain ordinary meaning and refers to an immune system that reacts to allergen in the environment that are normally harmless. Conditions related to an overactive immune system include asthma, eczema, and allergic rhinitis.

An "autoimmune disease" as used herein refers to a disease or disorder that arises from altered immune reactions by the immune system of a subject, e.g., against substances tissues and/or cells normally present in the body of the subject. Autoimmune diseases include, but are not limited to, arthritis, rheumatoid arthritis, psoriatic arthritis, juvenile idiopathic arthritis, scleroderma, systemic scleroderma, multiple sclerosis, systemic lupus erythematosus (SLE), myasthenia gravis, Juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, and allergic asthma.

The term "infection" or "infectious disease" is used in accordance with its plain ordinary meaning and refers to a disease or condition that can be caused by organisms such as a bacterium, virus, fungi or any other pathogenic microbial agents. In embodiments, the infectious disease is caused by a pathogenic bacteria. Pathogenic bacteria are bacteria which cause diseases (e.g., in humans). In embodiments, the infectious disease is a bacteria associated disease (e.g., tuberculosis, which is caused by *Mycobacterium tuberculosis*). Non-limiting bacteria associated diseases include pneumonia, which may be caused by bacteria such as *Streptococcus* and *Pseudomonas*; or foodborne illnesses, which can be caused by bacteria such as *Shigella, Campylobacter*, and *Salmonella*. Bacteria associated diseases also includes tetanus, typhoid fever, diphtheria, syphilis, and leprosy. In embodiments, the disease is Bacterial vaginosis (i.e. bacteria that change the vaginal microbiota caused by an overgrowth of bacteria that crowd out the Lactobacilli species that maintain healthy vaginal microbial populations) (e.g., yeast infection, or *Trichomonas vaginalis*); Bacterial meningitis (i.e. a bacterial inflammation of the meninges); Bacterial pneumonia (i.e. a bacterial infection of the lungs); Urinary tract infection; Bacterial gastroenteritis; or Bacterial skin infections (e.g. impetigo, or cellulitis). In embodiments, the infectious disease is human immunodeficiency virus (HIV), COVID-19, West Nile fever, Zika, malaria, Japanese encephalitis, tularemia, Chagas, sandfly fever, plague, rickettsiosis, influenza, cervicovaginal infections, and decubitus ulcers.

The term "patient" or "subject in need thereof" is used in accordance with its plain ordinary meaning and refers to a living organism suffering from or prone to a disease or condition that can be treated by administration of a composition, compound, or method as provided herein. Non-limiting examples include humans, other mammals, bovines, rats, mice, dogs, monkeys, goat, sheep, cows, deer, and other non-mammalian animals. In some embodiments, a patient is human. In embodiments, the subject has, had, or is suspected of having cancer.

As used herein, the terms "control" or "control experiment" are used in accordance with its plain ordinary meaning and refer to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As used herein, the terms "treating" or "treatment" are used in accordance with its plain ordinary meaning and refer to to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating includes preventing. In embodiments, treating does not include preventing.

As used herein, the term "prevent" is used in accordance with its plain ordinary meaning and refers to a decrease in the occurrence of disease symptoms in a patient. The prevention may be complete (no detectable symptoms) or partial, such that fewer symptoms are observed than would likely occur absent treatment.

By "therapeutically effective dose or amount" is intended an amount of cells, agents, or compounds described herein that brings about a positive therapeutic response in a subject in need of, such as an amount that restores function and/or results in the elimination and/or reduction of tumor and/or cancer cells. The exact amount (of cells or agents) required will vary from subject to subject, depending on the species, age, and general condition of the subject, the severity of the condition being treated, mode of administration, and the like. An appropriate "effective" amount in any individual case may be determined by one of ordinary skill in the art using routine experimentation, based upon the information provided herein. A "combined therapeutically effective dose or amount dose" refers a combination of therapies that together brings about a positive therapeutic response in a subject in need of, such as an amount that restores function and/or results in the elimination and/or reduction of tumor and/or cancer cells.

As used herein, the term "immune response" is used in accordance with its plain ordinary meaning and refers to a response by an organism that protects against disease. The response can be mounted by the innate immune system or by the adaptive immune system, as well known in the art.

As used herein, the term "cytotoxicity" is used in accordance with its plain ordinary meaning and refers to quality of being toxic to cells.

As used herein, the terms "antibody-dependent cellular cytotoxicity", "ADCC", and "antibody-dependent cell-mediated cytotoxicity" are used in accordance with their plain ordinary meanings and refer to an immune mechanism through which Fc receptor-bearing effector cells can recognize and kill antibody-coated target cells expressing tumor- or pathogen-derived antigens on their surface.

As used herein, the terms "antibody-dependent cellular phagocytosis" and "ADCP" are used in accordance with their plain ordinary meanings and refer to the mechanism by which antibody-opsonized target cells activate the Fc receptors on the surface of macrophages to induce phagocytosis, resulting the ingestion and degradation of the target cell. The macrophage Fc receptors refer to all classes of Fcγ receptors.

As used herein, the terms "adaptive immune response", "acquired immune system", and "specific immune system" are used in accordance with their plain ordinary meanings and refer to a subsystem of the overall immune system that is composed of specialized, systemic cells and processes that eliminate designated targets. The targets are designated by identification via immunological memory. Immunological memory is created when the immune system had previously encountered the immune assault, and retained a record of it.

As used herein, the terms "natural killer cells" and "NK cells" are used in accordance with their plain ordinary meaning and refer to a type of cytotoxic lymphocyte involved in the innate immune system. The role NK cells play is typically analogous to that of cytotoxic T cells in the vertebrate adaptive immune response. NK cells may provide rapid responses to virus-infected cells, acting at around 3 days after infection, and respond to tumor formation. Typically, immune cells detect major histocompatibility complex (MHC) presented on infected cell surfaces, triggering cytokine release, causing lysis or apoptosis. NK cells typically have the ability to recognize stressed cells in the absence of antibodies and MHC, allowing for a much faster immune reaction.

As used herein, the term "T cells" or "T lymphocytes" are used in accordance with their plain ordinary meaning and refer to a type of lymphocyte (a subtype of white blood cell) involved in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

As used herein, the terms "tumor microenvironment", "TME", and "cancer microenvironment" are used in accordance with its plain ordinary meaning and refer to the non-neoplastic cellular environment of a tumor, including blood vessels, immune cells, fibroblasts, cytokines, chemokines, non-cancerous cells present in the tumor, and proteins produced.

As defined herein, the terms "activation", "activate", "activating", "activator" and the like are used in accordance with its plain ordinary meaning and refer to an interaction that positively affects (e.g. increasing) the activity or function of a protein or cell relative to the activity or function of the protein or cell in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein that is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein As used herein, the terms "agonist," "activator," "upregulator," etc. are used in accordance with its plain ordinary meaning and refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As used herein, the terms "inhibition", "inhibit", "inhibiting" and the like are used in accordance with its plain ordinary meaning and refer to an interaction that negatively affecting (e.g. decreasing) the activity or function of the protein or cell relative to the activity or function of the protein or cell in the absence of the inhibitor. In embodiments, inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or downregulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein or cell from an indirect interaction (e.g. an inhibitor binds to a protein that activates the target protein, thereby preventing target protein activation or cell activations).

As used herein, the terms "inhibitor," "repressor" or "antagonist" or "downregulator" are used in accordance with its plain ordinary meaning and refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "expression" is used in accordance with its plain ordinary meaning and refers to any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

As used herein, the term "expression cassette" refers to a distinct component of vector DNA consisting of a gene and regulatory sequence to be expressed by a transfected cell. In each successful transformation, the expression cassette directs the cell's machinery to make RNA and protein(s). Some expression cassettes are designed for modular cloning of protein-encoding sequences so that the same cassette can easily be altered to make different proteins. An expression cassette is composed of one or more genes and the sequences controlling their expression. An expression cassette comprises three components: a promoter sequence, an open reading frame, and a 3' untranslated region that, in eukaryotes, usually contains a polyadenylation site. Different expression cassettes can be transfected into different organisms including bacteria, yeast, plants, and mammalian cells as long as the correct regulatory sequences are used.

As used herein, the term "cytokine" is used in accordance with its plain ordinary meaning and refers to a broad category of small proteins (~5-20 kDa) that are important in cell signaling. Cytokines are peptides, and cannot cross the lipid bilayer of cells to enter the cytoplasm. Cytokines are involved in autocrine signaling, paracrine signaling and endocrine signaling as immunomodulating agents. Cytokines include chemokines, interferons, interleukins, lymphokines, and tumor necrosis factors. Cytokines are produced by a broad range of cells, including immune cells like macrophages, B lymphocytes, T lymphocytes and mast cells, as well as endothelial cells, fibroblasts, and various stromal cells; a given cytokine may be produced by more than one type of cell.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins.

This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

As used herein, the terms "immunoglobulin domain" or "Ig-domain" are used in accordance with their plain and ordinary meanings and refer to any of the recombinant or naturally-occurring forms of the Ig-domain or variants or homologs thereof that maintain the Ig-domain fold or three-dimensional structure. The Ig-domain belongs to a family of protein folds that consist of a 2-layer sandwich of 7-9 antiparallel beta-strands arranged in two beta-sheets with a Greek-key topology. The folding pattern typically consists of (N-terminal beta-hairpin-in sheet 1)-(beta-hairpin-in sheet 2)-(beta-strand in sheet 1)-(C-terminal beta-hairpin in sheet 2) linkages. Immunoglobulin domains are the primary components of antibodies, and a large set of extracellular surface receptors, including receptor tyrosine kinases.

An example of an immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "$V_H$" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), $V_L$ (light chain variable region), $V_H$ (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries.

As used herein, the term "chimeric antibody" is used in accordance with its plain ordinary meaning and refers to an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

As used herein, the terms "Immunoglobulin G" or "IgG" are used in accordance with their plain and ordinary meanings and refer to any of the recombinant or naturally-occurring forms of the IgG antibody protein or variants or homologs thereof that maintain IgG activity (e.g. within at least 50%, 80%, 90%, 95%, 96%, 97%, 98%, 99% or 100% activity compared to IgG). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IgG Z/polypeptide. IgG antibodies are composed of four separate chains (two identical light chains and two identical heavy chains) that form a homodimer (via inter-heavy chain disulfide) of heterodimers (one light chain and one heavy chain interchain disulfide) in a canonical Y-shaped quaternary structure. The light chain includes a variable immunoglobulin domain (VL) and a constant immunoglobulin domain ($C_L$). The heavy chain includes one variable immunoglobulin domain ($V_H$) and three constant immunoglobulin domains ($C_H1$, $C_H2$, $C_H3$). The variable domains form the antigen-recognition surface of an IgG antibody. There are four subclasses of IgG, IgG1, IgG2, IgG3, and IgG4.

As used herein, the terms "CD47" and "Cluster of Differentiation 47" and integrin associated protein" or "IAP" refer to a transmembrane protein that in humans is encoded by the CD47 gene. CD47 belongs to the immunoglobulin superfamily and partners with membrane integrins and also binds the ligands thrombospondin-1 (TSP-1) and signal-regulatory protein alpha (SIRPα). CD-47 acts as a don't eat me signal to macrophages of the immune system which has made it a potential therapeutic target in some cancers, and more recently, for the treatment of pulmonary fibrosis. CD47 is involved in a range of cellular processes, including apoptosis, proliferation, adhesion, and migration. Furthermore, it plays a key role in immune and angiogenic responses. CD47 is ubiquitously expressed in human cells and has been found to be overexpressed in many different tumor cells. Expression in equine cutaneous tumors has been reported as well.

As used herein, the terms "anti-CD47 antibody" or "αCD47" refers to a protein capable of binding CD47 protein. Examples includes Hu5F9 (also known as 5F9). An anti-CD47 monoclonal antibody with an IgG1 isotype is referred to as αCD47-G1 (or Hu5F9-G1 or 5 F9-G1). An anti-CD47 monoclonal antibody with an IgG4 isotype is referred to as αCD47-G4 (or Hu5F9-G4 or 5fp-G4).

As used herein, the term "Signal regulatory protein α" or "SIRPα" refers to a regulatory membrane glycoprotein from SIRP family. SIRPα acts as inhibitory receptor and interacts with a broadly expressed transmembrane protein CD47 also called the "don't eat me" signal. This interaction negatively controls effector function of innate immune cells such as host cell phagocytosis.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

As used herein, the term "immunotherapy" and "immunotherapeutic agent" are used in accordance with their plain ordinary meaning and refer to the treatment of disease by activating or suppressing the immune system. Immunotherapies designed to elicit or amplify an immune response are classified as activation immunotherapies, while immunotherapies that reduce or suppress are classified as suppression immunotherapies. Such immunotherapeutic agents include antibodies and cell therapy.

As used herein, the term "checkpoint inhibitor" is used in accordance with its plain ordinary meaning and refers to a drug, often made of antibodies, that unleashes an immune system attack on cancer cells. An important part of the immune system is its ability to tell between normal cells in the body and those it sees as "foreign." This lets the immune system attack the foreign cells while leaving the normal cells alone. To do this, it uses "checkpoints" which are molecules on certain immune cells that need to be activated (or inactivated) to start an immune response. Cancer cells sometimes find ways to use these checkpoints to avoid being attacked by the immune system. Drugs that target these checkpoints are known as checkpoint inhibitors.

As used herein, the term "PD-1" is used in accordance with its plain ordinary meaning and refers to a checkpoint protein on immune cells called T cells. It acts as a type of "off switch" that helps keep the T cells from attacking other cells in the body. It does this when it attaches to PD-L1, a protein on some normal (and cancer) cells. When PD-1 binds to PD-L1, the signal notifies the T cell to leave the other cell alone. Some cancer cells have large amounts of PD-L1, which helps them evade immune attack.

As used herein, the term "PD-L1" or "programmed death-ligand 1 (PD-L1)" refers to a 40 kDa type 1 transmembrane protein that plays a role in suppressing the adaptive arm of immune system during particular events such as pregnancy, tissue allografts, autoimmune disease and other disease states. It appears that upregulation of PD-L1 may allow cancers to evade the host immune system.

As used herein, the term "CLTA-4", "CTLA4" and "cytotoxic T-lymphocyte-associated protein 4)", also known as CD152 (cluster of differentiation 152), refer to a protein receptor that functions as an immune checkpoint and down-regulates immune responses.

As used herein, the term "anticancer agent" and "anticancer therapy" are used in accordance with their plain ordinary meaning and refer to a molecule or composition (e.g. compound, peptide, protein, nucleic acid, drug, antagonist, inhibitor, modulator) or regimen used to treat cancer through destruction or inhibition of cancer cells or tissues. Anticancer therapy includes chemotherapy, radiation therapy, surgery, targeted therapy, immunotherapy, and cell therapy. Anticancer agents and/or anticancer therapy may be selective for certain cancers or certain tissues. In some embodiments, an anti-cancer therapy is an immunotherapy. In embodiments, anticancer agent or therapy may include a checkpoint inhibitor. In embodiments, the anti-cancer agent or therapy is a cell therapy.

In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone AN-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Carib-aeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), PARP inhibitors (olaparib, rucaparib, niraparib, talazoparib, veliparib, pamiparib, CEP 9722, E7016, and 3-aminobenzamide), sorafenib, imatinib, sunitinib, dasatinib, pembrolizumab nivolumab, atezolizumab, avelumab, durvalumab or the like.

As used herein, the term "administering" means oral administration, administration as a suppository, topical contact, intravenous, systemic, intracavitary, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent. As used herein, "systemic administration" refers to a route of administration into the circulatory system so that the entire body of a subject is affected. Systemic administration includes enteral and parenteral administration. As used herein, the term "intracavitary administration" refers to a route of administration within any natural, non-pathologic cavity.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

As used herein, the term "co-administer" refers to a composition described herein that is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "synergistic amount" as used herein refers to the sum of a first amount (e.g., an amount of a compound provided herein) and a second amount (e.g., a therapeutic agent) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

II. Compositions

In an aspect, provided herein is a recombinant oncolytic virus including an expression cassette encoding an anti- CD47 antibody. In an aspect, provided herein is a recombinant oncolytic virus including a nucleic acid encoding an anti-CD47 antibody.

An oncolytic virus is defined by its ability to selectivity replicate and kill dividing cells as compared to non-dividing cells. It may be a native virus that is naturally oncolytic or may be engineered by modifying one or more viral genes so as to increase tumor selectivity and/or preferential replication in dividing cells, such as those involved in DNA replication, nucleic acid metabolism, host tropism, surface attachment, virulence, lysis and spread (see for example Kim et al., 2001, Nat. Med. 7: 781; Wong et al., 2010, Viruses 2: 78-106). One may also envisage placing one or more viral gene(s) under the control of event or tissue-specific regulatory elements (e.g. promoter).

Exemplary oncolytic viruses include without limitation reovirus, Seneca Valley virus (SVV), vesicular stomatitis virus (VSV), Newcastle disease virus (NDV), herpes simplex virus (HSV), morbillivirus virus, retrovirus, influenza virus, Sin bis virus, poxvirus, adenovirus, or the like.

In an aspect, the oncolytic virus is a herpes virus. The Herpesviridae are a large family of DNA viruses that all share a common structure and are composed of relatively large double-stranded, linear DNA genomes encoding 100-200 genes encapsided within an icosahedral capsid which is enveloped in a lipid bilayer membrane. The oncolytic herpes virus can be derived from different types of HSV. In aspects, the oncolytic herpes virus is HSV1. In aspects, the oncolytic herpes virus is HSV2. The herpes virus may be genetically modified so as to restrict viral replication in tumors or reduce its cytotoxicity in non-dividing cells. For example, any viral gene involved in nucleic acid metabolism may be inactivated, such as thymidine kinase (Martuza et al., 1991, Science 252: 854-6), ribonucleotide reductase (RR) (Boviatsis et al., Gene Ther. 1: 323-31; Mineta et al., 1994, Cancer Res. 54: 3363-66), or uracil-N-glycosylase (Pyles et al., 1994, J. Virol. 68: 4963-72). Another aspect involves viral mutants with defects in the function of genes encoding virulence factors such as the ICP34.5 gene (Chambers et al., 1995, Proc. Natl. Acad. Sci. USA 92: 1411-5). Representative examples of oncolytic herpes virus include NV1020 (e.g. Geevarghese et al., 2010, Hum. Gene Ther. 21(9): 1119-28) and T-VEC (Andtbacka et al., 2013, J. Clin. Oncol. 31, abstract number LBA9008).

In an aspect, the oncolytic virus is a reovirus. A representative example includes Reolysin (under development by Oncolytics Biotech; NCT01166542).

In an aspect, the oncolytic virus is a Seneca Valley virus. A representative example includes NTX-010 (Rudin et al., 2011, Clin. Cancer. Res. 17(4): 888-95).

In an aspect, the oncolytic virus is a vesicular stomatitis virus (VSV). Representative examples are described (e.g. Stojdl et al., 2000, Nat. Med. 6(7): 821-5; Stojdl et al., 2003, Cancer Cell 4(4): 263-75).

In an aspect, the oncolytic virus is a Newcastle disease virus. Representative examples include without limitation the 73-T PV701 and HDV-HUJ strains as well as those described (e.g. Phuangsab et al., 2001, Cancer Lett. 172(1): 27-36; Lorence et al., 2007, Curr. Cancer Drug Targets 7(2): 157-67; Freeman et al., 2006, Mol. Ther. 13(1): 221-8).

In an aspect, the oncolytic virus is a morbillivirus which can be obtained from the paramyxoviridae family. In an aspect, the oncolytic virus is a measles virus. Representative examples of oncolytic measles viruses include without limitation MV-Edm (McDonald et al., 2006; Breast Cancer Treat. 99(2): 177-84) and HMWMAA (Kaufmann et al., 2013, J. Invest. Dermatol. 133(4): 1034-42)

In an aspect, the oncolytic virus is an adenovirus. Methods are available in the art to engineer oncolytic adenoviruses. Various aspects include the replacement of viral promoters with tumor-selective promoters or modifications of the E1 adenoviral gene product(s) to inactivate its/their binding function with p53 or retinoblastoma (Rb) protein that are altered in tumor cells. In the natural context, the adenovirus E1B55 kDa gene cooperates with another adenoviral product to inactivate p53 (p53 is frequently dysregulated in cancer cells), thus preventing apoptosis. Representative examples of oncolytic adenovirus include ONYX-015 (e.g. Khuri et al., 2000, Nat. Med 6(8): 879-85) and H101 also named Oncorine (Xia et al., 2004, Ai Zheng 23(12): 1666-70).

In an aspect, the oncolytic virus is a poxvirus. As used herein the term "poxvirus" refers to a virus belonging to the Poxviridae family. The poxvirus can be of the Chordopoxviridae subfamily and can be of the Orthopoxvirus genus. Sequences of the genome of various poxviruses, for example, the vaccinia virus, cowpox virus, Canarypox virus, Ectromelia virus, Myxoma virus genomes are available in the art and specialized databases such as Genbank (accession number NC_006998, NC_003663, NC_005309, NC_004105, NC_001132 respectively). The oncolytic poxvirus can be an oncolytic vaccinia virus. Vaccinia viruses are members of the poxvirus family characterized by a 200 kb double-stranded DNA genome that encodes numerous viral enzymes and factors that enable the virus to replicate independently from the host cell machinery. The majority of vaccinia virus particles is intracellular (IMV for intracellular mature virion) with a single lipid envelop and remains in the cytosol of infected cells until lysis. The other infectious form is a double enveloped particle (EEV for extracellular enveloped virion) that buds out from the infected cell without lysing it.

The anti-CD47 antibody can be a humanized antibody. The phrase "humanized antibodies" refers to monoclonal antibodies and antigen binding fragments thereof, including the nucleic acids encoding an antibody disclosed herein, that have binding and functional properties according to the disclosure similar to those disclosed herein, and that have framework and constant regions that are substantially human or fully human surrounding CDRs derived from a non-human antibody. "Framework region" or "framework sequence" refers to any one of framework regions 1 to 4. Humanized antibodies and antigen binding fragments encompassed by the present disclosure include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human Substantially human frameworks are those that have at least 80% sequence identity to a known human germline framework sequence. Preferably, the substantially human frameworks have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, to a framework sequence disclosed herein, or to a known human germline framework sequence.

CDRs encompassed by the present disclosure include not only those specifically disclosed herein, but also CDR sequences having sequence identities of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a CDR sequence disclosed herein. Alternatively, CDRs encompassed by the present disclosure include not only those specifically disclosed herein, but also CDR sequences having 1, 2, 3, 4, 5, or 6 amino acid changes at corresponding positions compared to CDR sequences disclosed herein. Such sequence identical, or amino acid modified, CDRs preferably bind to the antigen recognized by the intact antibody.

As used herein, the phrase "sequence identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, (Altschul, S. F. et al., J. Mol. Biol. 215: 403-410 (1990) and Altschul et al. Nucl. Acids Res. 25: 3389-3402 (1997)).

One example of an algorithm that is suitable for determining percent sequence identity and sequence similarity is the BLAST algorithm, which is described in (Altschul, S., et al., NCBI NLM NIH Bethesda, Md. 20894; & Altschul, S., et al., J. Mol. Biol. 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P (N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

Fully human frameworks are those that are identical to a known human germline framework sequence. Human framework germline sequences can be obtained from ImMunoGeneTics (IMGT) via their website or from The Immunoglobulin FactsBook by Marie-Paule Lefranc and Gerard Lefranc, Academic Press, 2001, ISBN 012441351. For example, germline light chain frameworks can be selected from the group consisting of: A11, A17, A18, A19, A20, A27, A30, LI, L1I, L12, L2, L5, L15, L6, L8, 012, 02, and 08, and germline heavy chain framework regions can be selected from the group consisting of: VH2-5, VH2-26, VH2-70, VH3-20, VH3-72, VHI-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-51.

Humanized antibodies in addition to those disclosed herein exhibiting similar functional properties according to the present disclosure can be generated using several different methods. In one approach, the parent antibody compound CDRs are grafted into a human framework that has a high sequence identity with the parent antibody compound framework. The sequence identity of the new framework will generally be at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identical to the sequence of the corresponding framework in the parent antibody compound. In the case of frameworks having fewer than 100 amino acid residues, one, two, three, four, five, six, seven, eight, nine, or ten amino acid residues can be changed. This grafting may result in a reduction in binding affinity compared to that of the parent antibody. If this is the case, the framework can be back-mutated to the parent framework at certain positions based on specific criteria disclosed by Queen et al. (1991) Proc. Natl. Acad. Sci. USA 88:2869. Additional references describing methods useful in humanizing mouse antibodies include U.S. Pat. Nos. 4,816,397; 5,225,539; and 5,693,761; computer programs ABMOD and ENCAD as described in Levitt (1983) J. Mol. Biol. 168:595-620; and the method of Winter and co-workers (Jones et al. (1986) Nature 321:522-525; Riechmann et al. (1988) Nature 332:323-327; and Verhoeyen et al. (1988) Science 239:1534-1536.

The identification of residues to consider for back-mutation can be carried out as follows: When an amino acid falls under the following category, the framework amino acid of the human germ-line sequence that is being used (the "acceptor framework") is replaced by a framework amino acid from a framework of the parent antibody compound (the "donor framework"): (a) the amino acid in the human framework region of the acceptor framework is unusual for human frameworks at that position, whereas the corresponding amino acid in the donor immunoglobulin is typical for human frameworks at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human framework region of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating human engineered antibodies exhibiting similar functional properties to the antibody compounds disclosed herein involves randomly mutating amino acids within the grafted CDRs without changing the framework, and screening the resultant molecules for binding affinity and other functional properties that are as good as or better than those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific framework regions in addition to introducing amino acid changes in the CDRs. This methodology is described in Wu et al. (1999) J. Mol. Biol. 294:151-162.

A person skilled in the art can use common techniques, e.g., site-directed mutagenesis, to substitute amino acids within the presently disclosed CDR and framework sequences and thereby generate further variable region amino acid sequences derived from the present sequences. Up to all naturally occurring amino acids can be introduced at a specific substitution site, including conservative amino acid substitutions as are well known to those of ordinary skill in the art. The methods disclosed herein can then be used to screen these additional variable region amino acid sequences to identify sequences having the indicated in vitro and/or in vivo functions. In this way, further sequences suitable for preparing human engineered antibodies and antigen-binding portions thereof in accordance with the present disclosure can be identified. In some embodiments, amino acid substitution within the frameworks can include one, two, three, four, five, six, seven, eight, nine, or ten positions within any one or more of the 4 light chain and/or heavy chain framework regions disclosed herein. In some embodiments, amino acid substitution within the CDRs is restricted to one, two, three, four, or five positions within any one or more of the 3 light chain and/or heavy chain CDRs. Combinations of the various changes within these framework regions and CDRs described above are also possible.

In embodiments, the recombinant oncolytic virus includes a nucleic acid sequence encoding an anti-CD47 antibody. The antibody encoded by the oncolytic virus of the invention can be of any origin, e.g. human, humanized, animal (e.g. rodent or camelid antibody) or chimeric. It may be of any isotype (e.g. IgG1, IgG2, IgG3, IgG4). In addition, it may be glycosylated, partially glycosylated or non-glycosylated (e.g. by mutating one or more residue(s) within the site(s) of glycosylation). The term antibody also includes bispecific or multispecific antibodies so long as they exhibit the binding specificity described herein.

The nucleic acid sequence encoding an anti-CD47 antibody can include a nucleic acid encoding a light chain signal peptide. In aspects, the nucleic acid sequence encoding a light chain signal peptide is SEQ ID NO.:2. The nucleic acid sequence encoding an anti-CD47 antibody can include a nucleic acid encoding a light chain variable region. In aspects, the nucleic acid sequence encoding a light chain variable region is SEQ ID NO.:3. The nucleic acid sequence encoding an anti-CD47 antibody can include a nucleic acid encoding a light chain constant region. In aspects, the nucleic acid sequence encoding a light chain constant region is SEQ ID NO.:4.

The nucleic acid sequence encoding an anti-CD47 antibody can encode an anti-CD47 (αCD47) IgG antibody utilizing the techniques of CDR grafting described above to provide a scaffold of an IgG (an antibody that incorporates portions of heavy chains of an IgG). In embodiments, the IgG is selected from IgG1, IgG2, IgG3, and IgG4. The nucleic acid sequence encoding an anti-CD47 IgG antibody (e.g. IgG1 or IgG4) can include a nucleic acid encoding a heavy chain signal peptide. In aspects, the nucleic acid sequence encoding a heavy chain signal peptide is SEQ ID NO.:5. The nucleic acid sequence encoding an anti-CD47 IgG antibody can include a nucleic acid encoding a heavy chain variable region. In aspects, the nucleic acid sequence encoding a heavy chain variable region is SEQ ID NO.:6.

The nucleic acid sequence encoding an anti-CD47 antibody can encode an anti-CD47 (αCD47) IgG1 antibody. The nucleic acid sequence encoding an anti-CD47 IgG1 antibody can include a nucleic acid encoding IgG1 heavy chain constant region $CH_1$. In aspects, the nucleic acid sequence encoding a IgG1 heavy chain constant region $CH_1$ is SEQ ID NO.:7. The nucleic acid sequence encoding an anti-CD47 IgG1 antibody can include a nucleic acid encoding IgG1 heavy chain hinge. In aspects, the nucleic acid sequence encoding a IgG1 heavy chain hinge is SEQ ID NO.:8. The nucleic acid sequence encoding an anti-CD47 IgG1 antibody can include a nucleic acid encoding IgG1 heavy chain constant region $CH_2$. In aspects, the nucleic acid sequence encoding a IgG1 heavy chain constant region $CH_2$ is SEQ ID NO.:9. The nucleic acid sequence encoding an anti-CD47 IgG1 antibody can include a nucleic acid encoding IgG1 heavy chain constant region $CH_3$. In aspects, the nucleic acid sequence encoding a IgG1 heavy chain constant region $CH_3$ is SEQ ID NO.:10.

In embodiments, the recombinant oncolytic virus includes a nucleic acid sequence encoding an αCD47 IgG2 antibody. In embodiments, the recombinant oncolytic virus includes a nucleic acid sequence encoding an αCD47 IgG3 antibody.

In embodiments, the recombinant oncolytic virus includes a nucleic acid sequence encoding an αCD47 IgG4 antibody. The nucleic acid sequence encoding an anti-CD47 IgG4 antibody can include a nucleic acid encoding IgG4 heavy chain constant region $CH_2$. In aspects, the nucleic acid sequence encoding an IgG4 heavy chain constant region $CH_2$ is SEQ ID NO.:11. The nucleic acid sequence encoding an anti-CD47 IgG4 antibody can include a nucleic acid encoding IgG4 heavy chain constant region $CH_3$. In aspects,

33 the nucleic acid sequence encoding a IgG1 heavy chain constant region CH$_3$ is SEQ ID NO.:12.

In embodiments, the oncolytic virus includes a nucleic acid sequence encoding an αCD47 ScFv.

The terminal 1 kb of the long repeat region (RL) of the HSV-1 and HSV-2 genomes contain a gene (11-13), that confers neurovirulence. Deletion or mutation of this gene results in variants that grow as well as wild type virus on dividing cells of many established cell lines, but show impaired replication on non-dividing cells. The oncolytic virus provided herein can lack a functional γ34.5 gene. In embodiments, the recombinant oncolytic virus does not include nucleic acid encoding a γ34.5 gene. In embodiments, the oncolytic herpes simplex virus does not include nucleic acid encoding a γ34.5 gene. In embodiments, the oncolytic herpes simplex 1 virus does not include nucleic acid encoding a γ34.5 gene. In embodiments, the oncolytic herpes simplex 2 virus does not include nucleic acid encoding a γ34.5 gene. In embodiments, the oncolytic herpes simplex virus does not include nucleic acid encoding a functional γ34.5 gene. In embodiments, the oncolytic herpes simplex 1 virus does not include nucleic acid encoding a functional γ34.5 gene. In embodiments, the oncolytic herpes simplex 2 virus does not include nucleic acid encoding a functional γ34.5 gene.

The ICP6 gene is a gene encoding the large subunit of ribonucleotide reductase (RR). RR is an enzyme necessary for virus DNA synthesis. Inactivation of this gene prevents virus replication in non-dividing cells. Only in cells which divide actively and have increased RR activity, the deficiency of the RR activity due to deletion of the ICP6 gene is compensated, enabling virus replication. The oncolytic virus provided herein can lack a functional IP6 gene. In embodiments, the recombinant oncolytic virus does not include nucleic acid encoding a functional ICP6 gene. In embodiments, the oncolytic herpes simplex virus does not include nucleic acid encoding a functional ICP6 gene. In embodiments, the oncolytic herpes simplex 1 virus does not include nucleic acid encoding a functional ICP6 gene. In embodiments, the oncolytic herpes simplex 2 virus does not include nucleic acid encoding a functional ICP6 gene.

The nucleic acid encoding an anti-CD47 antibody operably linked to elements for transcription and translation. The term "operably linked" means that the nucleotide sequence of interest is linked to regulatory sequence(s) in a manner that allows for expression of the nucleotide sequence. The regulatory sequence may include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like. In some examples, a vector has one or more transcription and/or translation control elements.

Non-limiting examples of suitable eukaryotic promoters (i.e., promoters functional in a eukaryotic cell) include those from cytomegalovirus (CMV) immediate early, H1, herpes simplex virus (HSV) thymidine kinase, early and late SV40, long terminal repeats (LTRs) from retrovirus, human elongation factor-1 promoter (EF1), a hybrid construct having the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I. The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

In embodiments, the recombinant oncolytic virus includes nucleic acid encoding an anti-CD47 antibody under the control of a viral or tumor specific gene promoter. In embodiments, the oncolytic herpes simplex virus includes nucleic acid encoding an anti-CD47 antibody under the control of a viral or tumor specific gene promoter. In embodiments, the oncolytic herpes simplex 1 virus includes nucleic acid encoding an anti-CD47 antibody under the control of a viral or tumor specific gene promoter. In embodiments, the oncolytic herpes simplex 2 virus includes nucleic acid encoding an anti-CD47 antibody under the control of a viral or tumor specific gene promoter.

In embodiments, the recombinant oncolytic virus includes nucleic acid encoding an anti-CD47 antibody under the control of a herpes simplex virus (HSV) promoter. In embodiments, the oncolytic herpes simplex virus includes nucleic acid encoding an anti-CD47 antibody under the control of a herpes simplex virus (HSV) promoter. In embodiments, the oncolytic herpes simplex 1 virus includes nucleic acid encoding an anti-CD47 antibody under the control of a herpes simplex virus (HSV) promoter. In embodiments, the oncolytic herpes simplex 2 virus includes nucleic acid encoding an anti-CD47 antibody under the control of a herpes simplex virus (HSV) promoter. In embodiments, the HSV promoter is an immediate early (IE) promoter. In embodiments, the HSV IE promoter is an IE 4/5 promoter.

The recombinant oncolytic virus can include a nucleic acid encoding a marker that can be used to determine whether the virus is present in the cell. The marker can be a selectable marker. A selectable marker is a gene introduced into a cell that confers a trait suitable for artificial selection. In embodiments, the recombinant oncolytic virus includes a nucleic acid encoding a marker within an ICP6 gene. In embodiments, the oncolytic herpes simplex virus includes a nucleic acid encoding a marker within an ICP6 gene. In embodiments, the oncolytic herpes simplex 1 virus includes a nucleic acid encoding a marker within an ICP6 gene. In embodiments, the oncolytic herpes simplex 2 virus includes a nucleic acid encoding a marker within an ICP6 gene. In embodiments, the marker is a selectable marker.

In embodiments, the pharmaceutical composition has one or more compounds of the present disclosure and one or more pharmaceutically acceptable excipients. In embodiments, the pharmaceutical compositions, the compound, or pharmaceutically acceptable salt thereof, is included in a therapeutically effective amount. In an aspect, provided herein is a pharmaceutical composition including a recombinant oncolytic virus as described herein, and a pharmaceutically acceptable carrier.

The pharmaceutical composition of the present disclosure can be prepared and administered in a wide variety of dosage formulations. Compounds described can be administered orally, rectally, or by injection (e.g. intratumorally, intracavitary, intravenously, intramuscularly, intracutaneously, subcutaneously, intraduodenally, or intraperitoneally). For example, the compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure can additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, *J Microencapsul.* 13:293-306, 1996; Chonn, *Curr. Opin. Biotechnol.* 6:698-708, 1995; Ostro, *Am. J Hosp. Pharm.* 46:1576-1587, 1989). The compositions can also be delivered as nanoparticles.

In embodiments, provided herein is a pharmaceutical composition including a recombinant oncolytic virus encoding an anti-CD47 antibody, and a pharmaceutically acceptable carrier. In embodiments, provided herein is a pharmaceutical composition including an oncolytic herpes simplex virus encoding an anti-CD47 antibody, and a pharmaceutically acceptable carrier. In embodiments, provided herein is a pharmaceutical composition including an oncolytic herpes simplex virus encoding an anti-CD47 antibody under the control of a viral or tumor specific gene promoter, and a pharmaceutically acceptable carrier. In embodiments, provided herein is a pharmaceutical composition including an oncolytic herpes simplex virus encoding an anti-CD47 antibody under the control of a herpes simplex virus (HSV) promoter, and a pharmaceutically acceptable carrier. In embodiments, provided herein is a pharmaceutical composition including an oncolytic herpes simplex virus encoding an anti-CD47 antibody under the control of a herpes simplex virus (HSV) immediate early (IE) promoter, and a pharmaceutically acceptable carrier. In embodiments, provided herein is a pharmaceutical composition including an oncolytic herpes simplex virus encoding an anti-CD47 antibody under the control of a herpes simplex virus (HSV) immediate an IE 4/5 promoter. promoter, and a pharmaceutically acceptable carrier. In embodiments, the pharmaceutical composition further includes an anti-cancer agent.

III. Methods of Use

In an aspect, provided herein is a method for killing tumor cells in a subject including administering to a subject an effective amount of the recombinant oncolytic virus according to any embodiment as described herein. The compositions provided herein are oncolytic viruses that express an anti-CD47 antibody. While not wishing to be held to theory, the oncolytic virus replicates preferentially in the tumor cell and and the anti-CD47 antibody binds to the CD47 receptor that helps the tumor evade the host immune system. In aspects, the composition is administered directly to the tumor location. Methods for tumor location and access are known in the art. Compositions can be administered to a subject in need by any of the methods further described below. Progress in tumor killing can be monitored by any of the methods of imaging tumors or measuring tumor markers known in the art.

In an aspect, provided herein are methods of treating cancer in a subject in need including administering to the patient an effective amount of a pharmaceutical composition including a recombinant oncolytic virus as described above, and a pharmaceutically acceptable carrier as described herein or the recombinant oncolytic virus according to any embodiment as described herein. In embodiments, the pharmaceutical composition is co-administered with an anti-cancer therapy. The anti-cancer therapy can include, but is not limited to, chemotherapy (anti-cancer agents), radiation therapy, surgery, targeted therapy, immunotherapy, or cell therapy. Anticancer agents can include, but are not limited to, checkpoint inhibitors and PARP inhibitors (see "anticancer agents" in Definitions). The pharmaceutical composition and anti-cancer agent can be in separate dosage formats. The pharmaceutical composition and anti-cancer agent can be in different types of dosage formats. The pharmaceutical composition and anti-cancer agent can be administered by different routes of administration.

In embodiments, the cancer is a chronic cancer. Chronic cancer is cancer that cannot be cured but that ongoing treatment, also called extended treatment, can control for months or years. As with other chronic disease, the goal of extended treatment for cancer is to help patients live as well as possible for as long as possible. Cancer progression can be monitored by methods known in the art.

In embodiments, the cancer is a solid tumor. Solid tumors include, but are not limited to, histiocytic lymphoma, cancers of the brain, genitourinary tract, lymphatic system, stomach, larynx and lung. In embodiments, the cancer an inflammatory chronic cancer. Markers of inflammation, such at cytokine expression, can be monitored.

In embodiments, the cancer is a CD47 expressing cancer. Because the recombinant oncolytic viruses disclosed herein express an anti-CD47 antibody, it would be expected that the compositions would be particularly effective in such cancers. A tumor type can be tested for the expression of CD47 by methods known in the art, such as by ELISA or FACS detection using an anti-CD47 antibody. Gliablastomas and ovarian cancers are demonstrated herein to express CD47. In embodiments, the cancer is glioblastoma, ovarian cancer, pancreatic cancer, leukemia, myeloma, or lymphoma. In embodiments, cancer is glioblastoma. In embodiments, cancer is ovarian cancer. In embodiments, cancer is pancreatic cancer. In embodiments, cancer is leukemia. In embodiments, cancer is myeloma. In embodiments, cancer is lymphoma.

In an aspect, provided herein is a method of treating a subject with an overactive immune system, including administering to the patient an effective amount of a pharmaceutical composition including a recombinant oncolytic virus as described above, and a pharmaceutically acceptable carrier as described herein or the recombinant oncolytic virus according to any embodiment as described herein.

In embodiments of methods of treating a subject with an overactive immune system, the subject has asthma or eczema. In embodiments, the subject has asthma. In embodiments, the subject has eczema. In embodiments of methods of treating a subject with an overactive immune system, the subject has allergic rhinitis.

In an aspect, provided herein is a method of treating a subject with an autoimmune disease, including administering to the patient an effective amount of a pharmaceutical composition including a recombinant oncolytic virus as described above, and a pharmaceutically acceptable carrier as described herein or the recombinant oncolytic virus according to any embodiment as described herein.

In embodiments, the autoimmune disease is arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, and allergic asthma. In embodiments, the autoimmune disease is arthritis. In embodiments, the autoimmune disease is rheumatoid arthritis. In embodiments, the autoimmune disease is psoriatic arthritis. In embodiments, the autoimmune disease is juvenile idiopathic arthritis. In embodiments, the autoimmune disease is scleroderma In embodiments, the autoimmune disease is systemic scleroderma. In embodiments, the autoimmune disease is multiple sclerosis. In embodiments, the autoimmune disease is systemic lupus erythematosus (SLE). In embodiments, the autoimmune disease is myasthenia gravis. In embodiments, the autoimmune disease is juvenile onset diabetes. In embodiments, the autoimmune disease is diabetes mellitus type 1. In embodiments, the autoimmune disease is Guillain-Barre syndrome. In embodiments, the autoimmune disease is Hashimoto's encephalitis. In embodiments, the autoimmune disease is Hashimoto's thyroiditis. In embodiments, the autoimmune disease is ankylosing spondylitis. In embodiments, the autoimmune disease is psoriasis. In embodiments, the autoimmune disease is Sjogren's syndrome. In embodiments, the autoimmune disease is vasculitis. In embodiments, the autoimmune disease is glomerulonephritis. In embodiments, the autoimmune disease is auto-immune thyroiditis. In embodiments, the autoimmune disease is Behcet's disease. In embodiments, the autoimmune disease is Crohn's disease. In embodiments, the autoimmune disease is ulcerative colitis. In embodiments, the autoimmune disease is bullous pemphigoid. In embodiments, the autoimmune disease is sarcoidosis. In embodiments, the autoimmune disease is ichthyosis. In embodiments, the autoimmune disease is Graves ophthalmopathy. In embodiments, the autoimmune disease is inflammatory bowel disease. In embodiments, the autoimmune disease is Addison's disease. In embodiments, the autoimmune disease is Vitiligo. In embodiments, the autoimmune disease is asthma. In embodiments, the autoimmune disease is allergic asthma.

In an aspect, provided herein is a method of treating a subject with an infectious disease, including administering to the patient an effective amount of a pharmaceutical composition including a recombinant oncolytic virus as described above, and a pharmaceutically acceptable carrier as described herein or the recombinant oncolytic virus according to any embodiment as described herein. The recombinant oncolytic virus compositions disclosed herein can boost a subject's immune system to fight off an infection. In embodiments infectious disease is human immunodeficiency virus (HIV). In embodiments infectious disease is COVID-19. In embodiments infectious disease is influenza. In embodiments infectious disease is pneumonia. In embodiments infectious disease is syphilis. In embodiments infectious disease is anthrax. In embodiments infectious disease is gonorrhea. In embodiments infectious disease is HPV. In embodiments infectious disease is mononucleosis. In embodiments infectious disease is West Nile fever. In embodiments infectious disease is Zika. In embodiments infectious disease is malaria. In embodiments infectious disease is plague.

In embodiments, immune modulation includes activating natural killer (NK) cells. NK cells can play a critical anti-tumor activity in cancers including GBM via natural cytotoxicity and ADCC, especially in combination with antibody therapy (see, for example, Ref. 31). Oncolytic virus compositions provided herein induce activation of NK cells. NK cell activation induction can be confirmed by cytotoxicity assays and by measuring the expression of the activation marker CD69 on NK cells, such as by flow cytometry (see Examples). In embodiments, activation of NK cells is measured as induction of cell-mediated antibody-dependent cellular cytotoxicity. In embodiments, activation of NK cells is measured as expression of CD69 on NK cells. In embodiments, activation of NK cells is measured as increased NK cell cytotoxicity.

In an aspect, provided herein is a method for increasing cytotoxicity of natural killer (NK) cells and/or CD8 T cells in a subject, including administering to the patient an effective amount of a pharmaceutical composition including a recombinant oncolytic virus as described above, and a pharmaceutically acceptable carrier as described herein or the recombinant oncolytic virus according to any embodiment as described herein.

In an aspect, provided herein is a method for increasing survival and/or proliferation of immune cells in a subject, including administering to the patient an effective amount of a pharmaceutical composition including a recombinant oncolytic virus as described above, and a pharmaceutically acceptable carrier as described herein or the recombinant oncolytic virus according to any embodiment as described herein.

In embodiments, the immune cell is a natural killer (NK) cell. In embodiments, the immune cell is a CD8 T-cell.

The compositions may be administered in a single dose (e.g. bolus injection) or multiple doses. If multiple administrations, they may be performed by the same or different routes and may take place at the same site or at alternative sites. It is also possible to proceed via sequential cycles of administrations that are repeated after a rest period. Intervals between each administration can be from several hours to one year (e.g. 24 h, 48 h, 72 h, weekly, every two weeks, monthly or yearly). Intervals can also be irregular (e.g.

following tumor progression). The doses can vary for each administration within the range described above.

Any of the conventional administration routes are applicable including parenteral, topical or mucosal routes. Parenteral routes are intended for administration as an injection or infusion. Common parenteral injection types are intravenous (into a vein), intra-arterial (into an artery), intradermal (into the dermis), subcutaneous (under the skin), intramuscular (into muscle) and intratumoral (into tumor or at its close proximity). Infusions typically are given by intravenous route. Mucosal administrations include without limitation oral/alimentary, intranasal, intratracheal, intrapulmonary, intravaginal or intra-rectal route. Topical administration can also be performed using transdermal means (e.g. patch and the like). Administrations may use conventional syringes and needles (e.g. Quadrafuse injection needles) or any compound or device available in the art capable of facilitating or improving delivery of the active agent(s) in the subject. Routes of administration for the oncolytic virus include intravenous and intratumoral routes.

In embodiments, administering includes intratumoral, systemic, or intracavitary administration. In embodiments, administering is intratumoral administration. In embodiments, administering is systemic administration. In embodiments, administering is intracavitary administration.

The compositions may be administered once or several time (e.g. 2, 3, 4, 5, 6, 7 or 8 times etc) at a dose within the range of from 107 to $5 \times 10^9$ pfu. The time interval between each administration can vary from approximately 1 day to approximately 8 weeks, advantageously from approximately 2 days to approximately 6 weeks, preferably from approximately 3 days to approximately 4 weeks and even more preferably from approximately 1 week to approximately 3 weeks (e.g. every two weeks for example).

In an embodiment the method of the invention provides a higher therapeutic efficacy than the one obtained in the same conditions with a similar oncolytic virus (without immune checkpoint modulator) or the immune checkpoint modulator either individually or even in co-administration. In the context of the invention, the method of the invention provides at least 5%, at least 10%, at least 15%, at least 20%, or at least 25% more therapeutic efficacy than either the virus or the immune check point modulator alone or in co-administration. A higher therapeutic efficacy could be evidenced as described above in connection with the term "therapeutically effective amount" with a specific preference for a longer survival.

The present invention also provides kits including a different container (e.g., a sterile glass or plastic vial) for each virus dose to be administered. Optionally, the kit can include a device for performing the administration of the active agents. The kit can also include a package insert including information concerning the compositions or individual component and dosage forms in the kit.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Experimental Background

Oncolytic virus (OV) provides a therapeutic approach for glioblastoma (GBM) as its mechanism of action is completely different from the standard approaches for the treatment of GBM. Oncolytic herpes simplex virus (oHSV), one of the most widely investigated oncolytic viruses, is genetically engineered so that it can selectively lyse cancer cells while leaving normal cells intact. Like many other OVs, oHSV can also alert the patients' immune system to attack tumor cells. Talimogene laherparepvec (Imlygic), the first FDA-approved oncolytic viral therapy, consists of an oHSV (see, for example, Ref. 2). oHSV has proven relatively safe and has shown some activity in treating GBM (see, for example, Ref. 3). In previous studies, data showed that oHSV treatment dramatically increased the intratumoral infiltration of immune cells (see, for example, Refs. 4-8) However, most tumor cells have evolved to engage the immune checkpoints and down-modulate the immune cells, thereby evading the anti-tumor immune response (see, for example, Refs. 9-10). Thus, engineering oHSV to express a transgene(s) that could enhance immune responses and/or block engagement of immune checkpoints could be an effective approach to improve the overall efficacy of oHSV against GBM.

Tumor-associated macrophages (TAM) and microglia are the major tumor-promoting immune cells in the GBM microenvironment (see, for example, Refs. 11-12) Hence, re-education of TAM and tumor-associated microglia in GBM is a promising antitumor strategy (See, for example, Refs. 13-14). The signal-regulatory protein (SIRP)$\alpha$-CD47 pathway is one of the most studied phagocytosis checkpoints in macrophages and microglia (see, for example, Ref. 15). CD47-SIRP$\alpha$ myeloid checkpoint blockade has been shown to effectively enhance tumor phagocytosis and hence reduce tumor burden (see, for example, Refs. 16-18). A humanized anti-CD47 antibody, which directly inhibits the CD47-SIRP$\alpha$ interaction, is currently in clinical trials showing strong activity against GBM (see, for example, Refs. 17, 19). For safety concerns, this antibody was engineered on a human IgG4 scaffold to minimize Fc-dependent effector functions of innate immunity such as antibody-dependent cellular cytotoxicity (ADCC) and complement-dependent cytotoxicity (CDC) (see, for example, Ref. 20). However, infusion toxicities and difficulty in passing through the blood brain barrier are challenges when the monoclonal antibody are administrated systemically to treat GBM.

In experiments described herein, oHSV was engineered to express a full length, soluble anti-CD47 antibody with an IgG1 scaffold (OV-H5F9-G1) and this was compared to another version that was engineered with an IgG4 scaffold (OV-H5F9-G4) in order to assess for locoregional treatment of glioblastoma (GBM), a devastating brain tumor without curative treatment options. Once it infects the GBM cell, the oHSV encodes a full-length anti-CD47 antibody that is secreted by the GBM and blocks the "don't eat me" signal normally mediated by the interaction of the innate immune cell's SIRP-$\alpha$ (a receptor) and its ligand, CD47, expressed by the tumor cell. Blocking this "don't eat me" signal allows for cytotoxicity against the tumor cell by antibody-dependent cellular phagocytosis (ADCP). In vitro, both versions of secreted antibodies blocked the CD47-SIRP-$\alpha$ axis, thereby enhancing phagocytosis of tumor cells by macrophages, with a stronger effect against GBM cells seen with the IgG1 version due to: (1) an additional ADCP effect via binding with macrophage Fc$\gamma$RIIIA (CD16) and (2) a strong antibody-dependent cellular cytotoxicity (ADCC) by CD16 (+) natural killer (NK) cells. Interestingly, data showed that the Fc-FcR-dependent cytotoxic effect was much stronger than the effect of blocking the CD47-SIRP$\alpha$ axis, i.e., the former contributes most to the overall cytotoxic effect of OV-H5F9-G1 against GBM. In vivo, following locoregional oncolytic virotherapy of GBM, these multifaceted functions of OV-H5F9-G1 and OV-H5F9-G4 led to improvement of survival in orthotopic xenograft animal models, compared to control oHSV alone, with a superior effect seen with the OV-H5F9-G1 construct compared to the OV-H5F9-G4 construct. Data showed that both OV-H5F9-G1 and OV-H5F9-G4, each encoding a secretable full length antibody, could be administered safely without apparent toxicity. Collectively, data herein demonstrated that an oncolytic herpes virus encoding a full length anti-CD47 antibody, especially an IgG1 version, is a promising approach for improving the treatment of GBM via its novel enhancement of FcR(+) innate immune cell function.

Example 2: Results

OV-Hu5F9-G1- or OV-Hu5F9-G4-Infected GBM Cells Secrete a Full-Length Anti-CD47 Antibody.

Figure 1A:
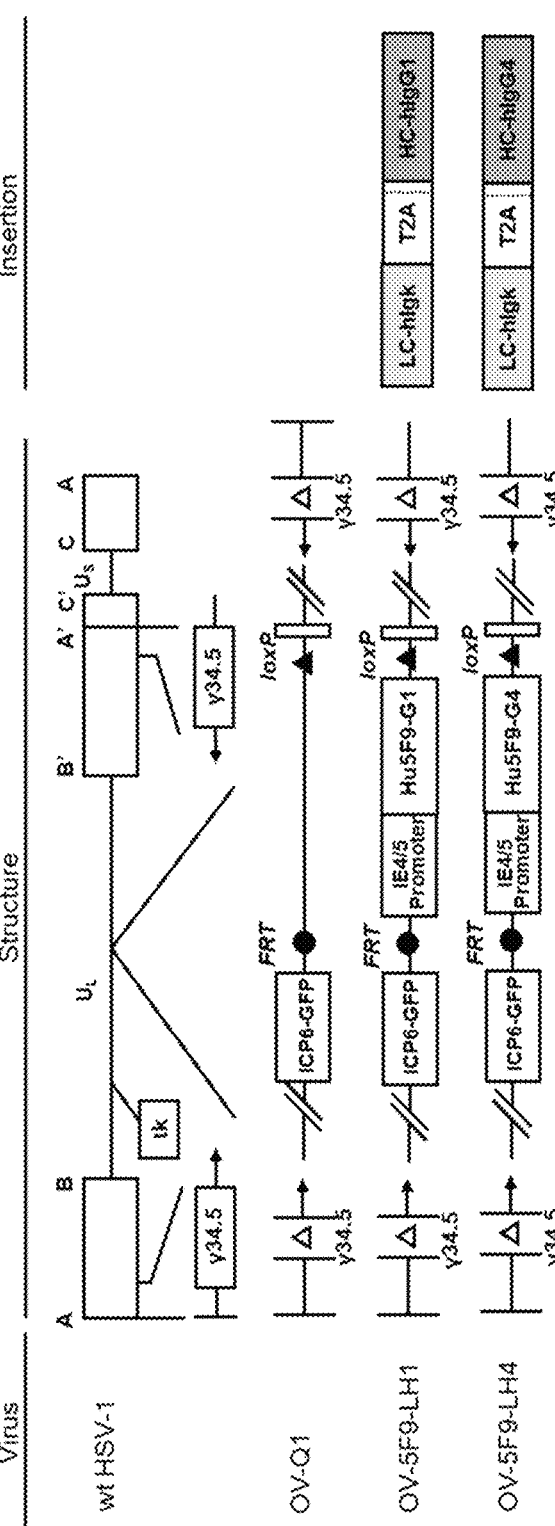
FIGS. 1A-1E depict construction and characterization of OV-Q1, OV-Hu5F9-G1 and OV-Hu5F9-G4 (Hu5F9 also known as αCD47 (alpha-CD47) throughout this specification).
Figure 1B:
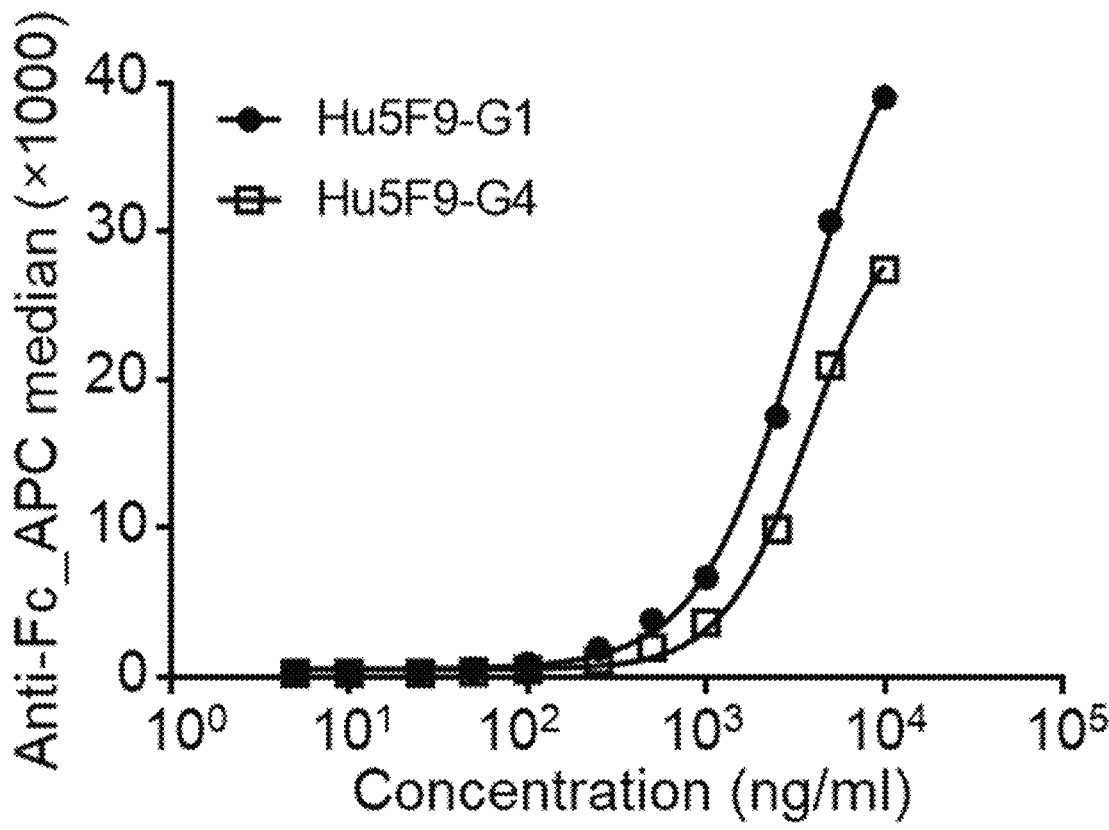
Figure 1C:
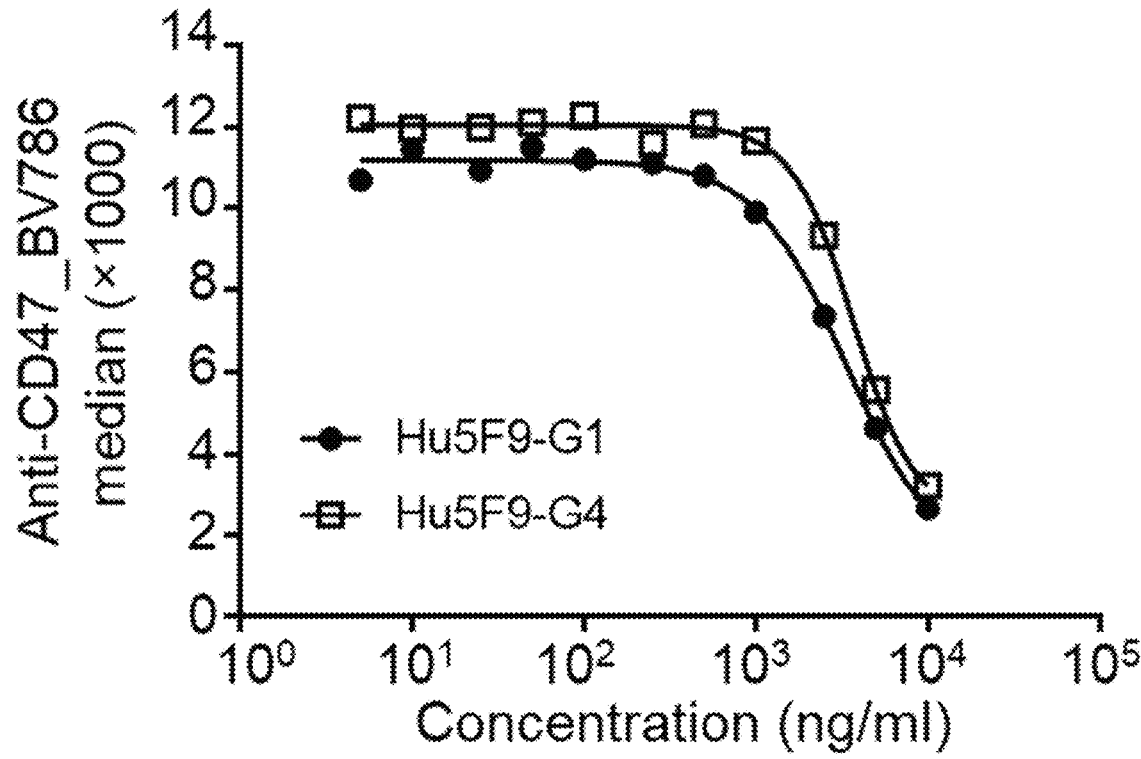

First, we assessed six human GBM cell lines, including patient-derived stem-like GBM30, GBM43 and BT422, and observed that each uniformly expressed CD47 on the cell surface. Next, constructs of αCD47-G1 (IgG1 version) and OV-αCD47-G4 (IgG4 version) were generated, that express an IgG1 or IgG4 version of humanized anti-human CD47 antibody coding genes including a full-length of both heavy chain and light chain, driven by the promoter of the HSV-1 immediate early gene IE4/5. αCD47-G4 was re-constructed as previously reported (see, for example, Ref. 20). αCD47-G1 was constructed by replacing the human IgG4 constant region of αCD47-G4 with the human IgG1 constant region. For both versions of anti-CD47, the light chain and heavy chains were linked with a T2A self-cleaving peptide as illustrated in FIG. 1A. The top line of FIG. 1A is the genetic map of wild type HSV-1. The second line is a genetic map of control oHSV, OV-Q1, with deletion of two copies of γ34.5, dysfunction of ICP6, and insertion of the GFP gene. The third line is a genetic map of OV-αCD47-G1 showing the inserted coding gene of IgG1 version of anti-CD47 (Hu5F9-G1) that is constructed on human IgG1 scaffold. The light chain and heavy chain coding genes of Hu5F9-G1 are linked by a T2A sequences and are driven by the viral pIE4/5 promoter. The fourth line is the genetic map of OV-αCD47-G4 demonstrating the inserted coding gene of the IgG4 version of anti-CD47 (αCD47-G4) that is constructed on the scaffold of human IgG4 instead of IgG1.

Figure 7A:
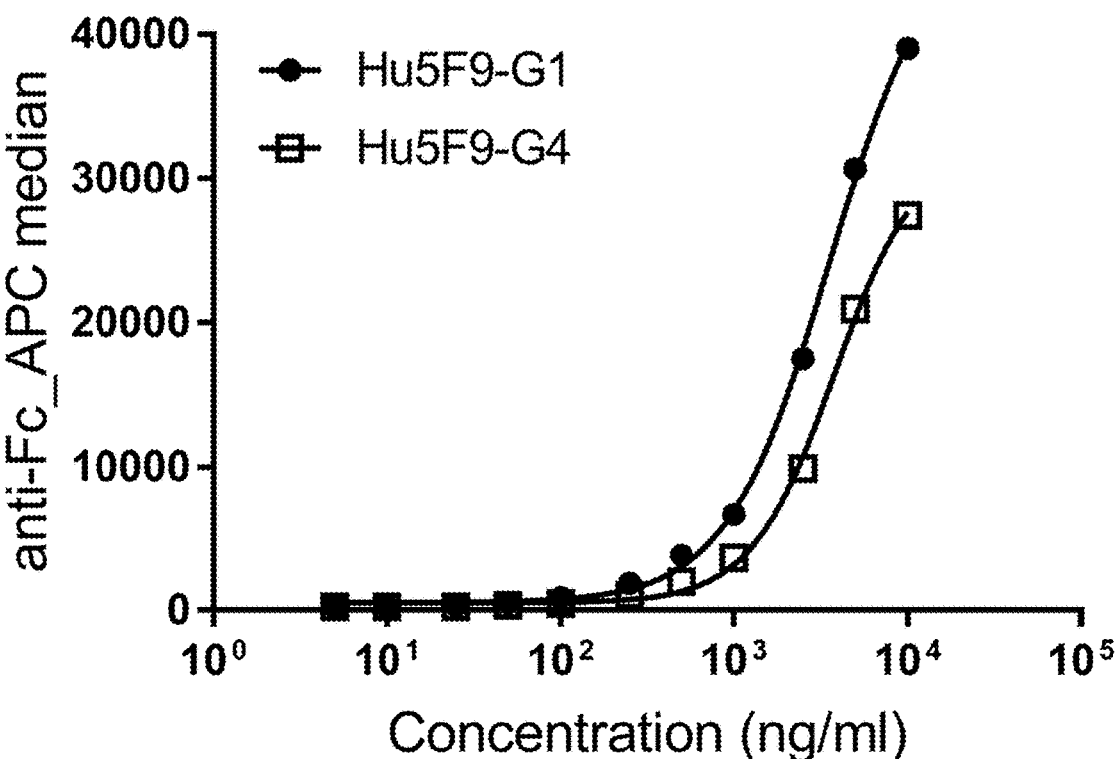
FIGS. 7A-7B are graphs showing dose-dependent binding.
Figure 7B:
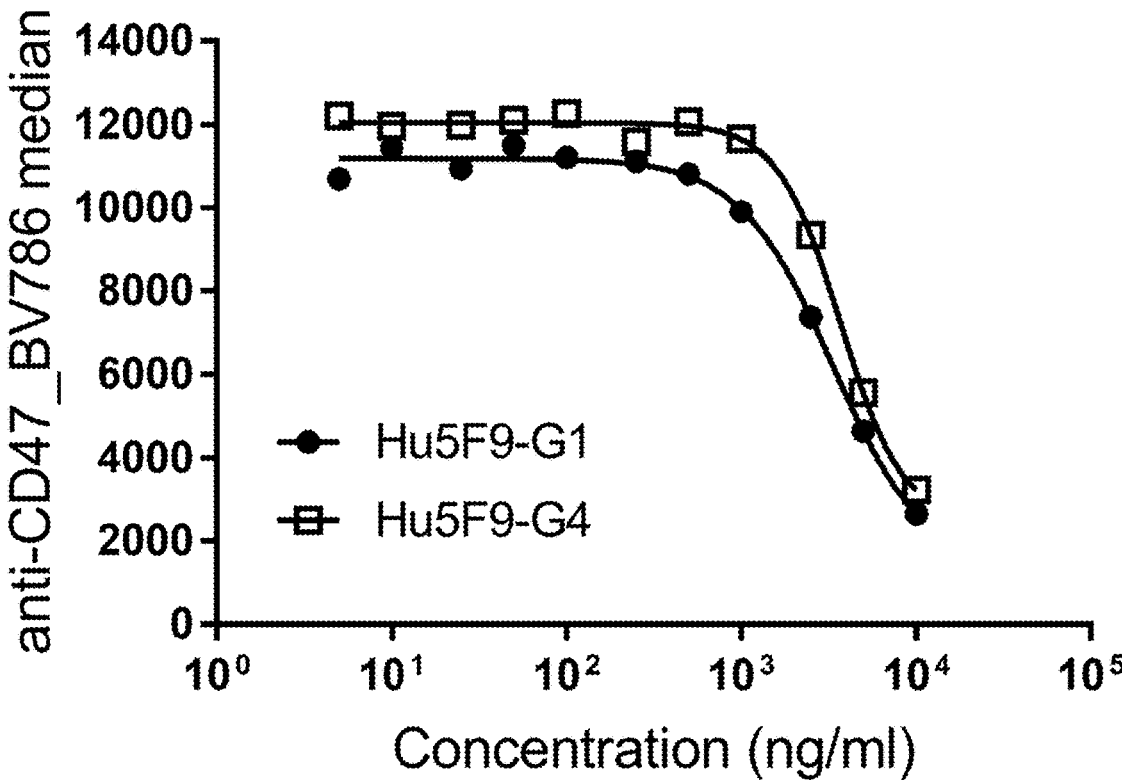
Figure 8A:
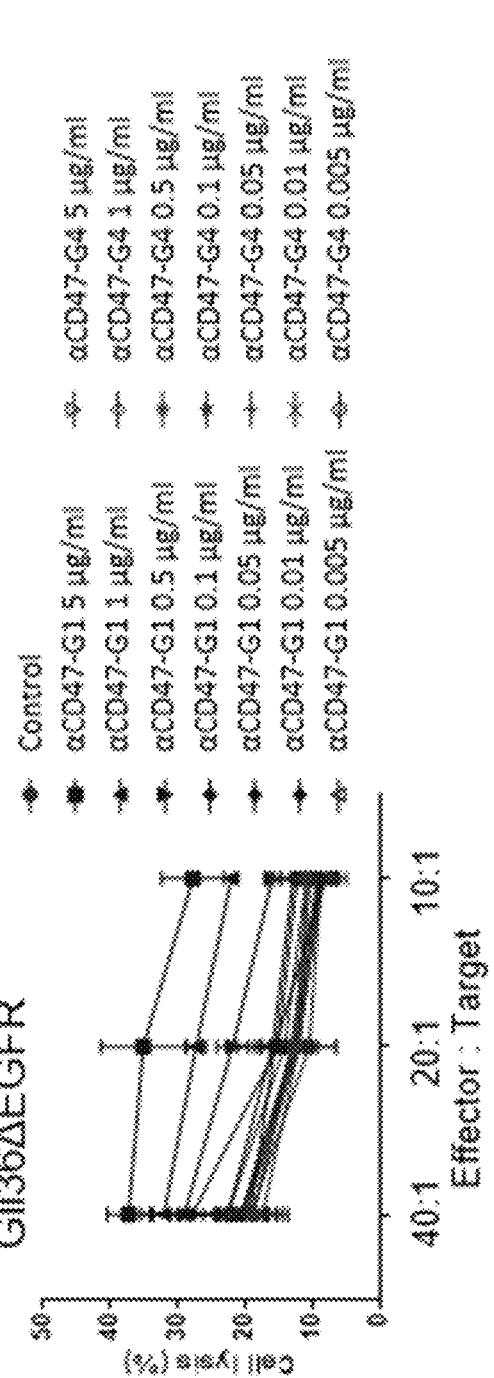
FIGS. 8A-8D show that αCD47-G1 but not αCD47-G4 induces cytotoxicity of human NK cells against GBM cells.
Figure 8B:
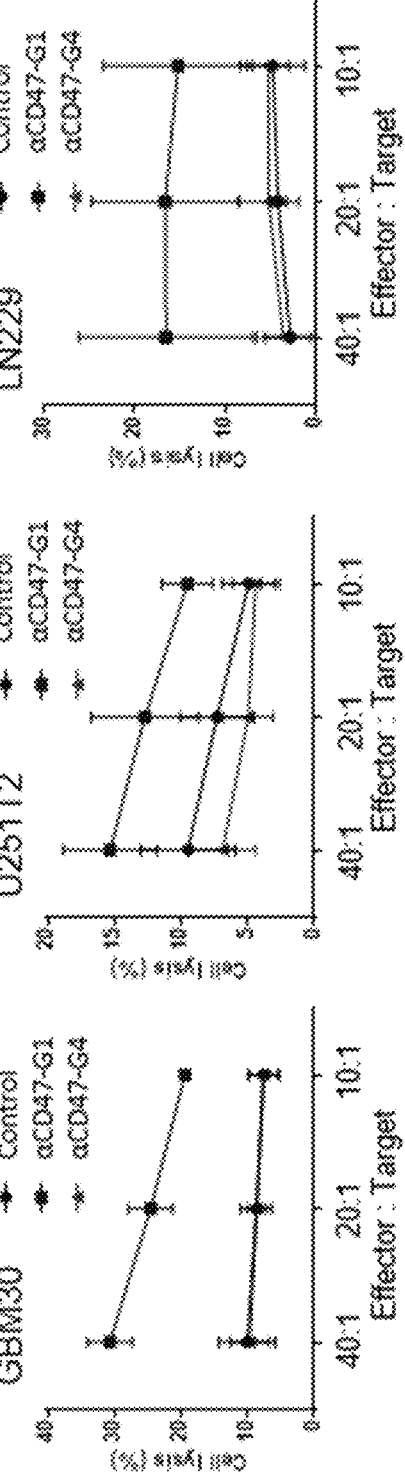
Figure 8C:
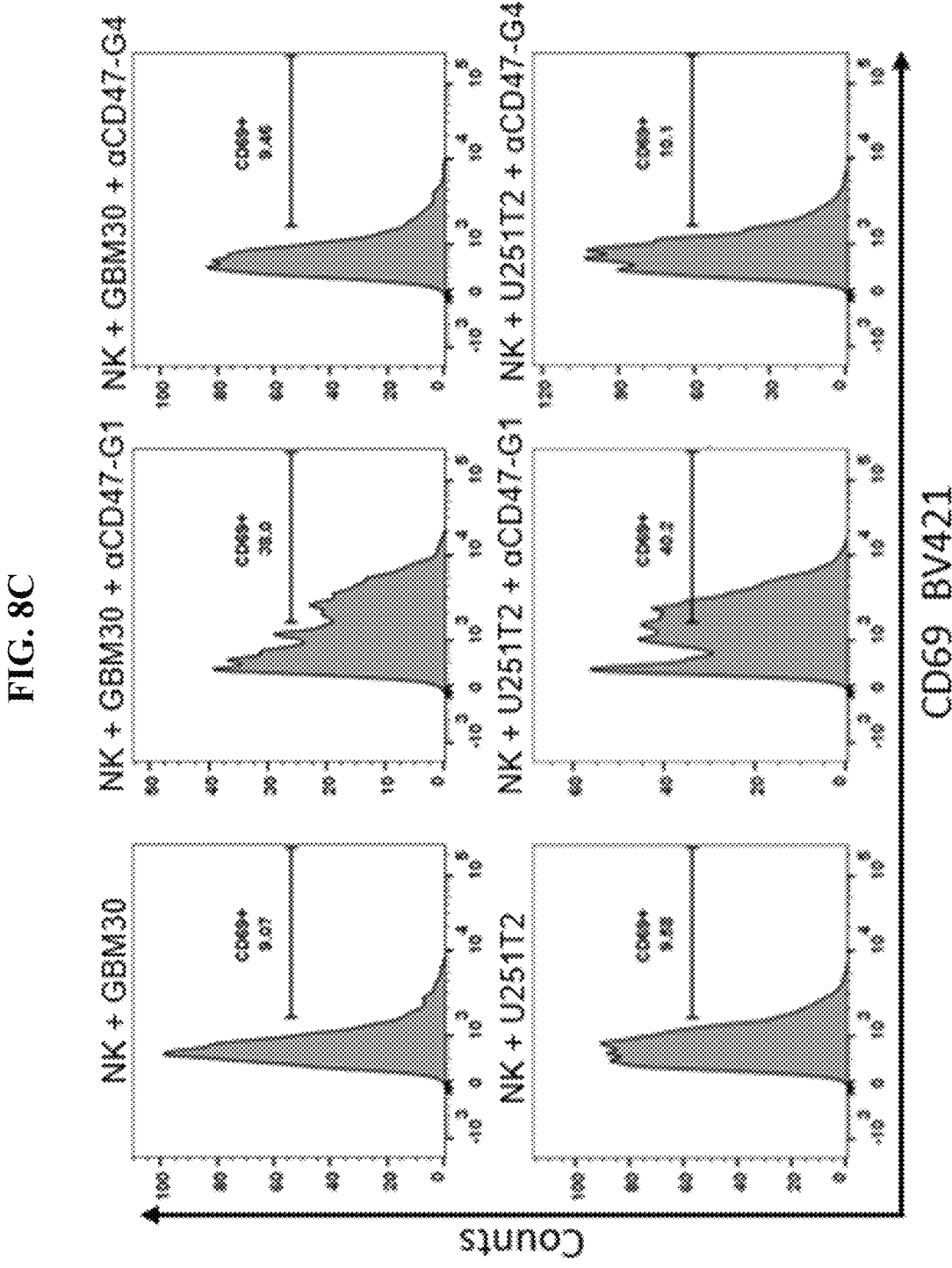
Figure 8D:
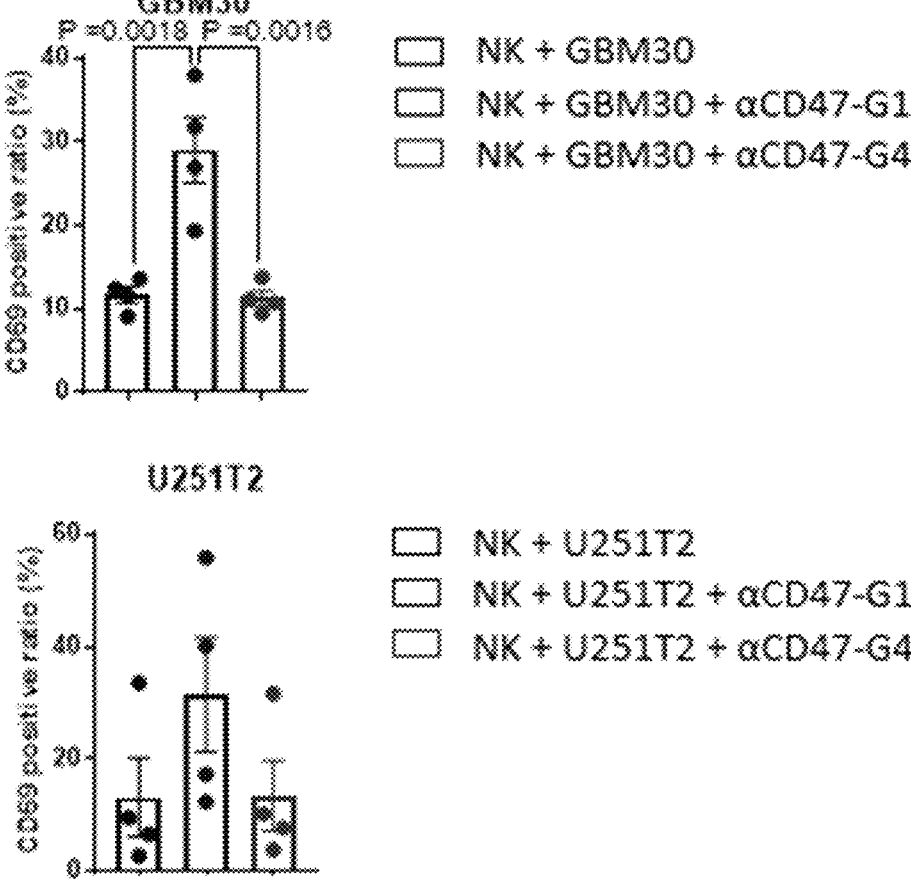

The CD47 binding affinity and blocking activity of αCD47-G1 and αCD47-G4 were tested by a flow cytometric assay, using the antibodies purified from supernatants of cultured CHO cells lentivirally transduced with the corresponding coding vector. For this, CD47(+) U251T2 cells were incubated with αCD47-G1 or αCD47-G4 at gradient concentrations. Results showed dose-dependent binding of αCD47-G1 and αCD47-G4 to CD47(+) U251T2 GBM cells, demonstrating that the two antibodies have almost equal binding affinity to the CD47(+) U251T2 cells (FIG. 7A). For the blocking assay, U251T2 cells were incubated with Hu5F9-G1 or Hu5F9-G4 at gradient concentrations, followed by staining with a commercially available anti-CD47 (clone, B6H12). Results showed a similar dose-dependent decrease of BV786 signal when Hu5F9-G1 and Hu5F9-G4 were added, indicating that Hu5F9-G1 and Hu5F9-G4 have a similar CD47 blocking capacity (FIG. 7B).

Figure 1D:
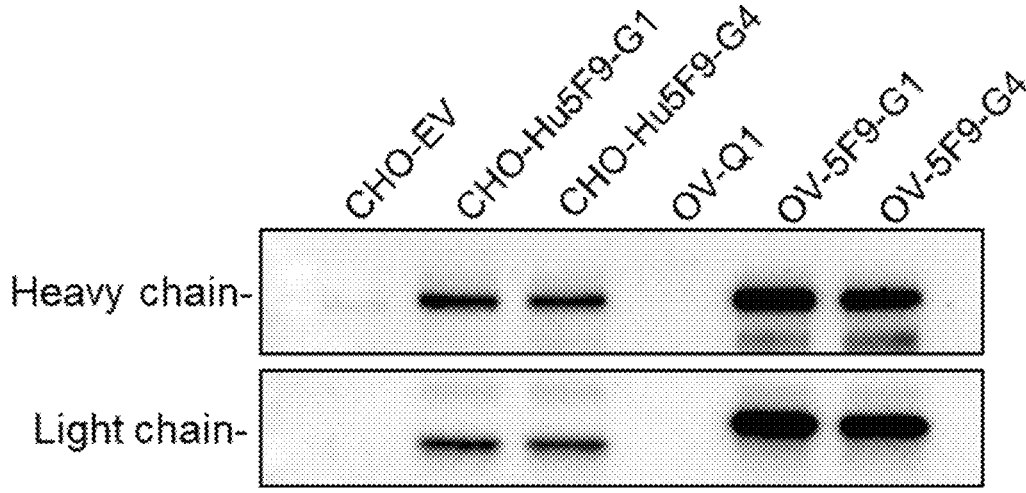
Figure 1E:
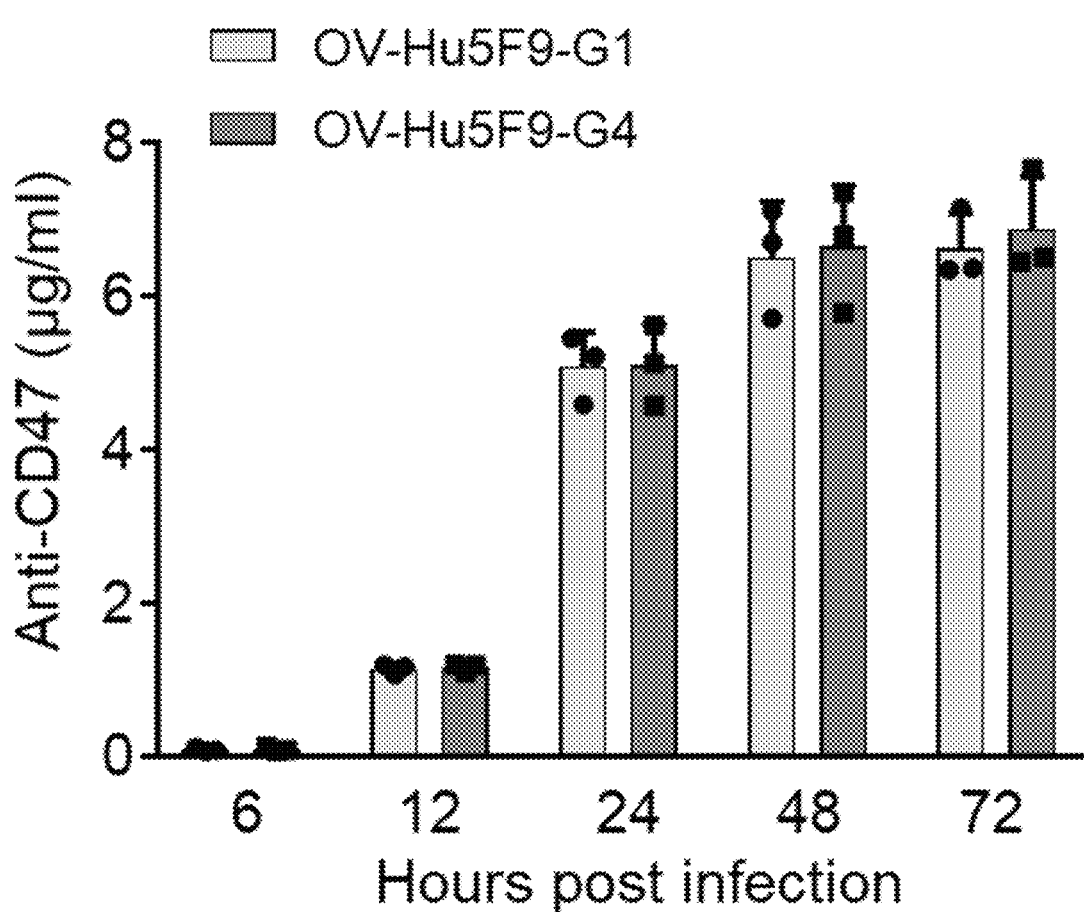

After demonstrating the two antibody constructs worked in a lentiviral vector, experiments were performed to generate oHSV expressing each version of the antibodies, using the parental oHSV named OV-Q1, which was double-attenuated with an inactivated ribonucleotide reductase gene (ICP6) and deletions of both copies of the neurovirulence gene (ICP34.5) that limits its replication only in tumor cells and reduces its neurovirulence (see, for example, Refs. 21-22). The two oHSVs were generated in a manner that was previously reported (see, for example, Ref. 4) and are termed OV-αCD47-G1 and OV-αCD47-G4. The genetic maps of wild-type human HSV-1, OV-Q1, OV-αCD47-G1 and OV-αCD47-G4 are illustrated in FIG. 1A. Infection of GBM cells with OV-αCD47-G1 or OV-αCD47-G4 enabled the infected cells to secrete IgG1 or IgG4 versions of anti-CD47, respectively. The supernatants from OV-αCD47-G1-, OV-αCD47-G4- or OV-Q1-infected U251T2 GBM cells were concentrated with protein G columns twenty-four hours after saturated infection (MOI=3) to obtain the requisite amount required for detection by immunoblot. An immunoblot was undertaken with the concentrated supernatants and demonstrated that human IgG heavy chain and light chain existed within the supernatants from OV-αCD47-G1- and OV-αCD47-G4-infected U251T2 GBM cells (FIG. 1D). The light chain expressed by OV-αCD47-G1 and OV-αCD47-G4 displayed a larger molecular size, likely due to remaining of the 17 amino acid N-terminus residues of the T2A peptide left in light chain resulting from the self-cleavage of T2A between glycine (G) and proline (P) at its C-terminus (see, for example, Ref. 23) (FIG. 1D). The yield of anti-CD47 from OV-αCD47-G1- and OV-αCD47-G4-infected U251T2 GBM cells were quantified by flow cytometry assay, using corresponding antibodies purified from CHO cells with known concentrations as standards. The OV-5F9-G1- and OV-5F9-G4-infected U251T2 GBM cells released appreciable amount of anti-CD47 as early as 12 hours post infection, and the yields reached peak levels >6 μg/ml in culture at 24 hours post infection (FIG. 1E).

OV-5F9-G1 and OV-5F9-G4 Retain Oncolytic Potency and Virus Production.

Figure 2A:
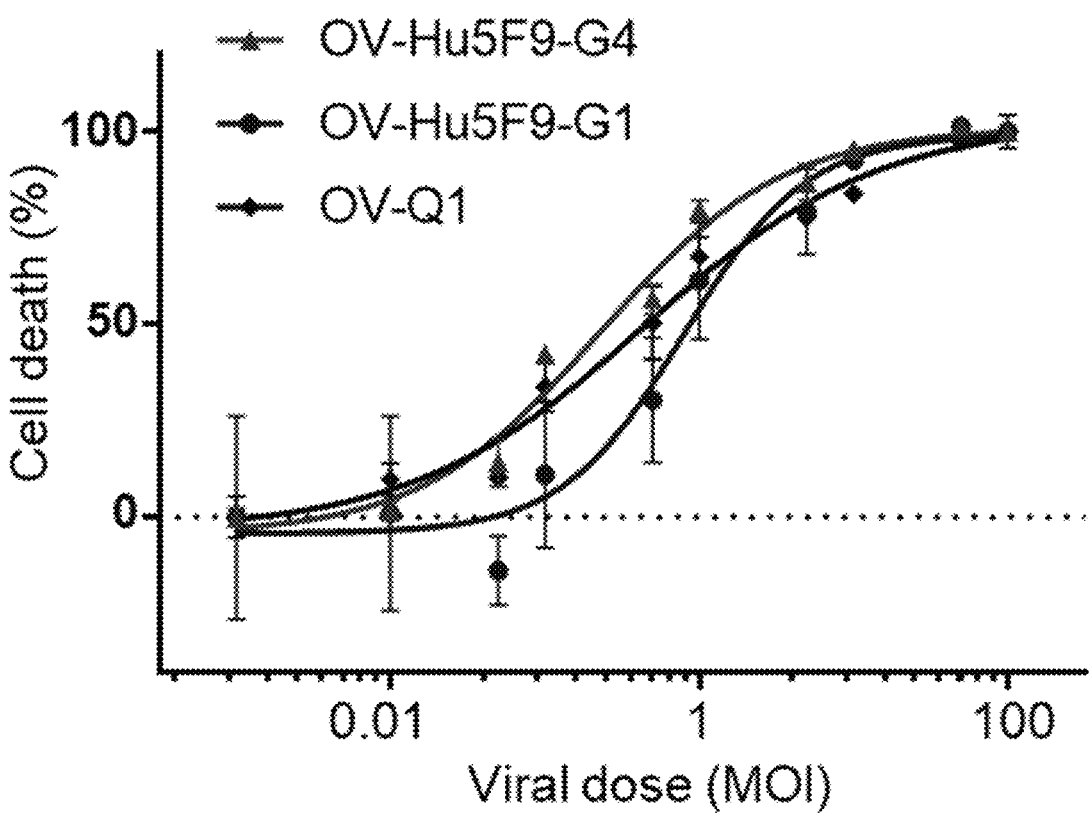
FIGS. 2A-2D demonstrate viral production and infectivity of OV-αCD47-G1 and OV-αCD47-G4.
Figure 2B:
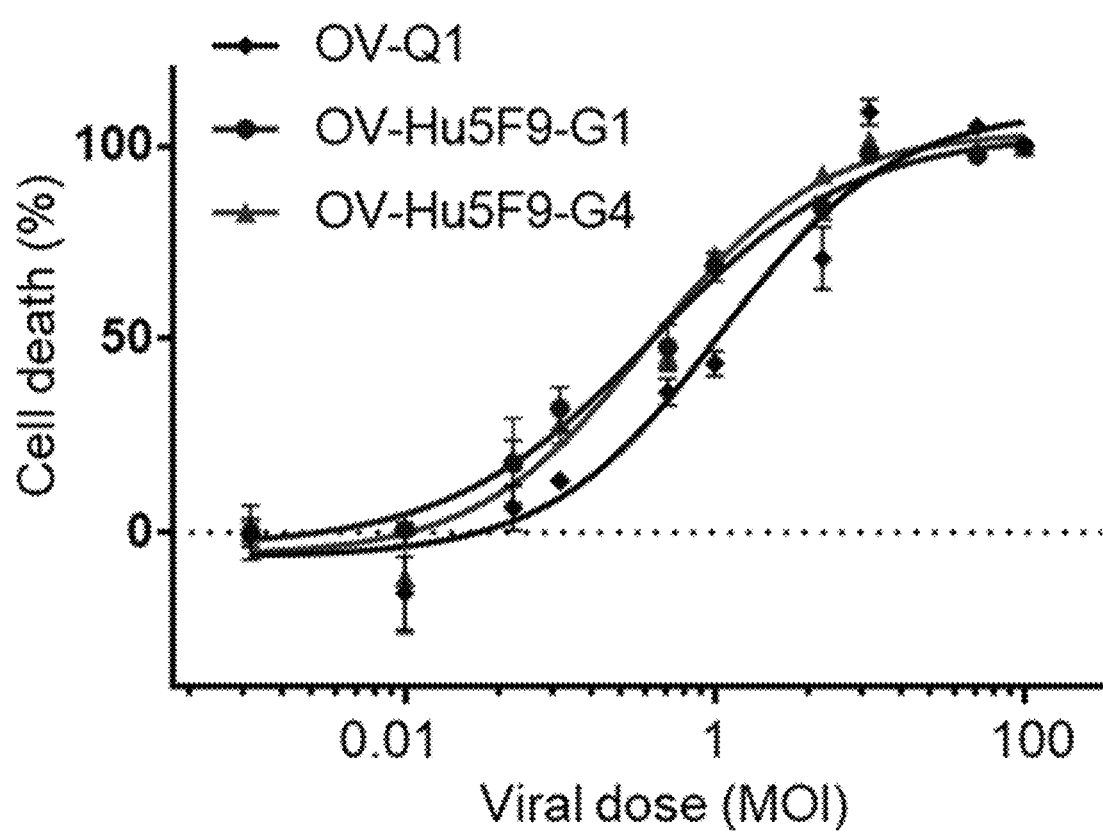

To test the oncolytic effect of OV-αCD47-G1 and OV-αCD47-G4, the GBM cell lines U251T2 (FIG. 2A) and Gli36dEGFR (FIG. 2B) were infected with the corresponding viruses. There were no significant difference in cell death among GBM cells infected with OV-5F9-G1, OV-5F9-G4, or the parental oHSV named OV-Q1.

Figure 2C:
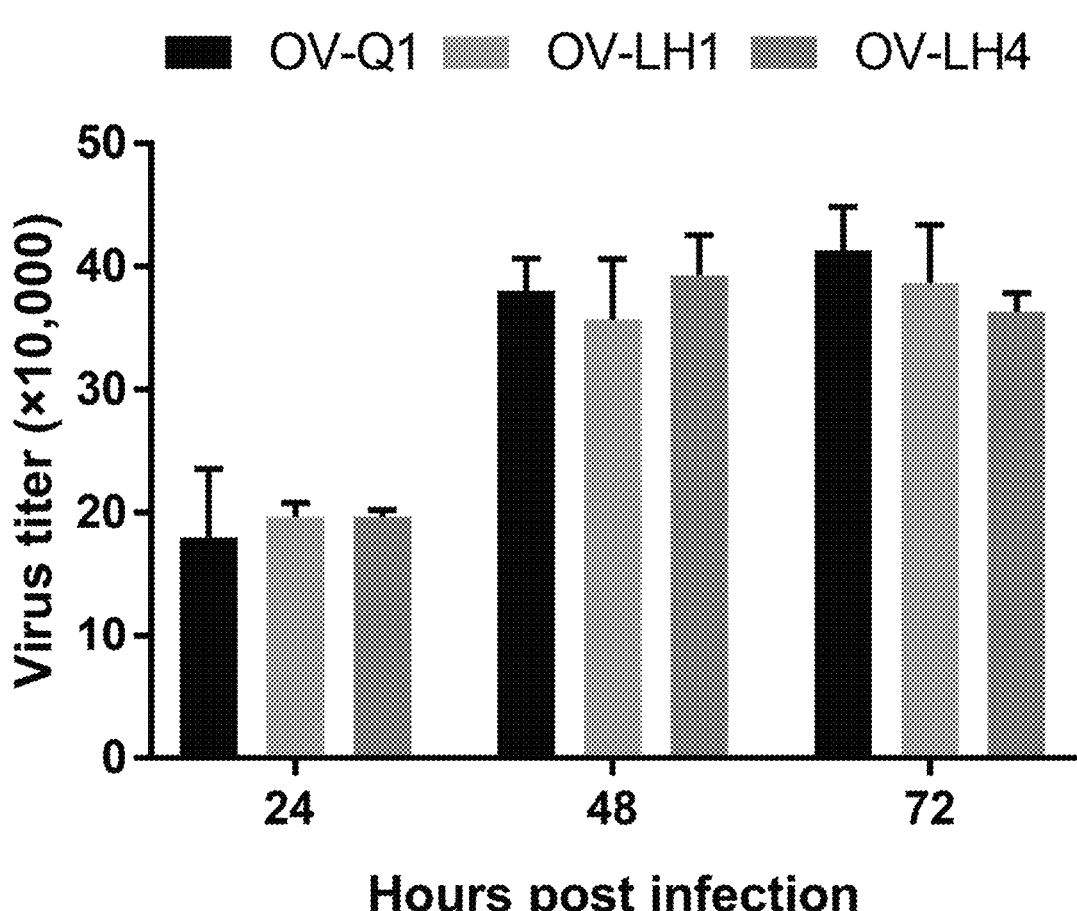
Figure 2D:
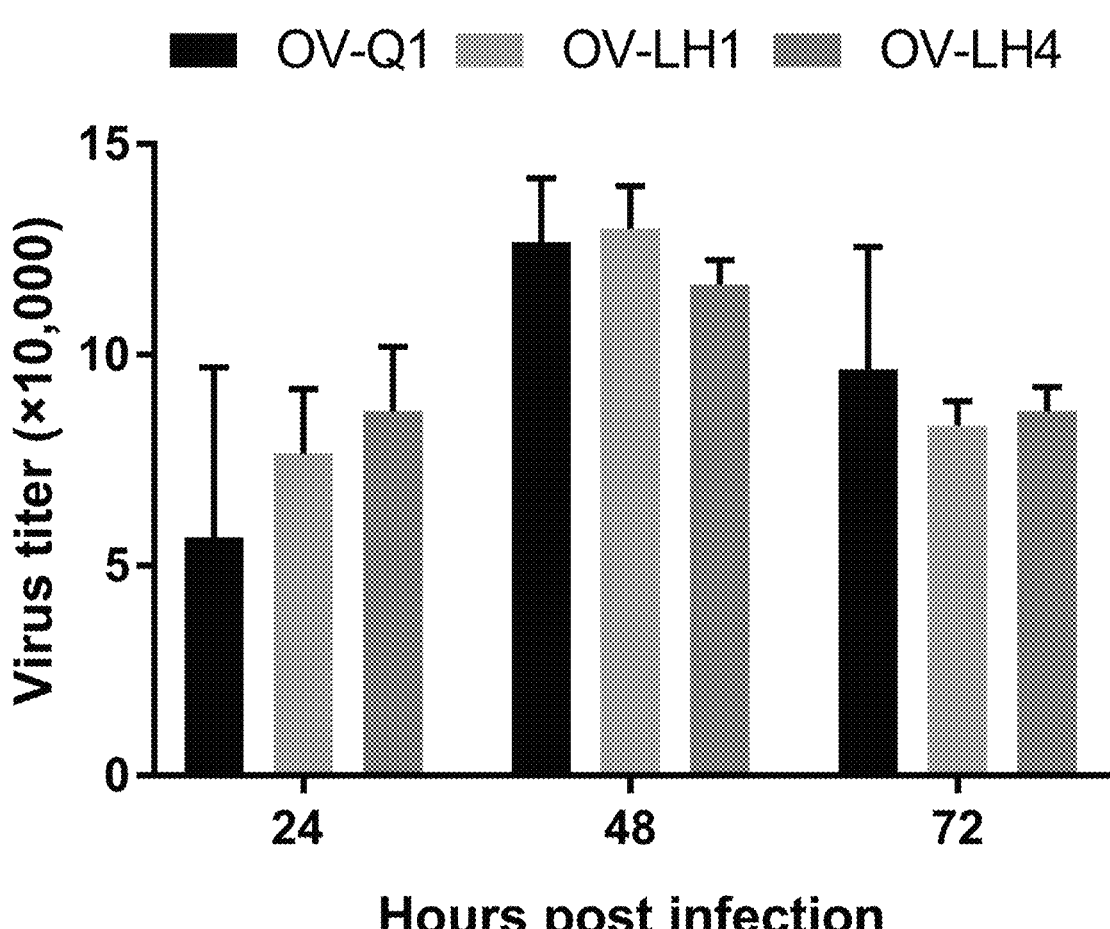

Next, the viral production capacities of OV-αCD47-G1 and OV-αCD47-G4 were evaluated. Results showed that OV-αCD47-G1 and OV-αCD47-G4-infected U251T2 GBM cells (FIG. 2C) or Gli36 GBM cells (FIG. 2D) produce similar amounts of oHSV when compared to the same GBM cells infected with the parental oHSV OV-Q1. Therefore, engineering oHSV to infect GBM with Hu5F9-G1 or Hu5F9-G4 did not affect their oncolysis or viral production.

The Enhancement of Macrophage-Mediated Phagocytosis by αCD47-G1 is Largely Mediated by Antibody Dependent Cellular Phagocytosis (ADCP). Not Via Blockade of CD47.

Figure 3A:
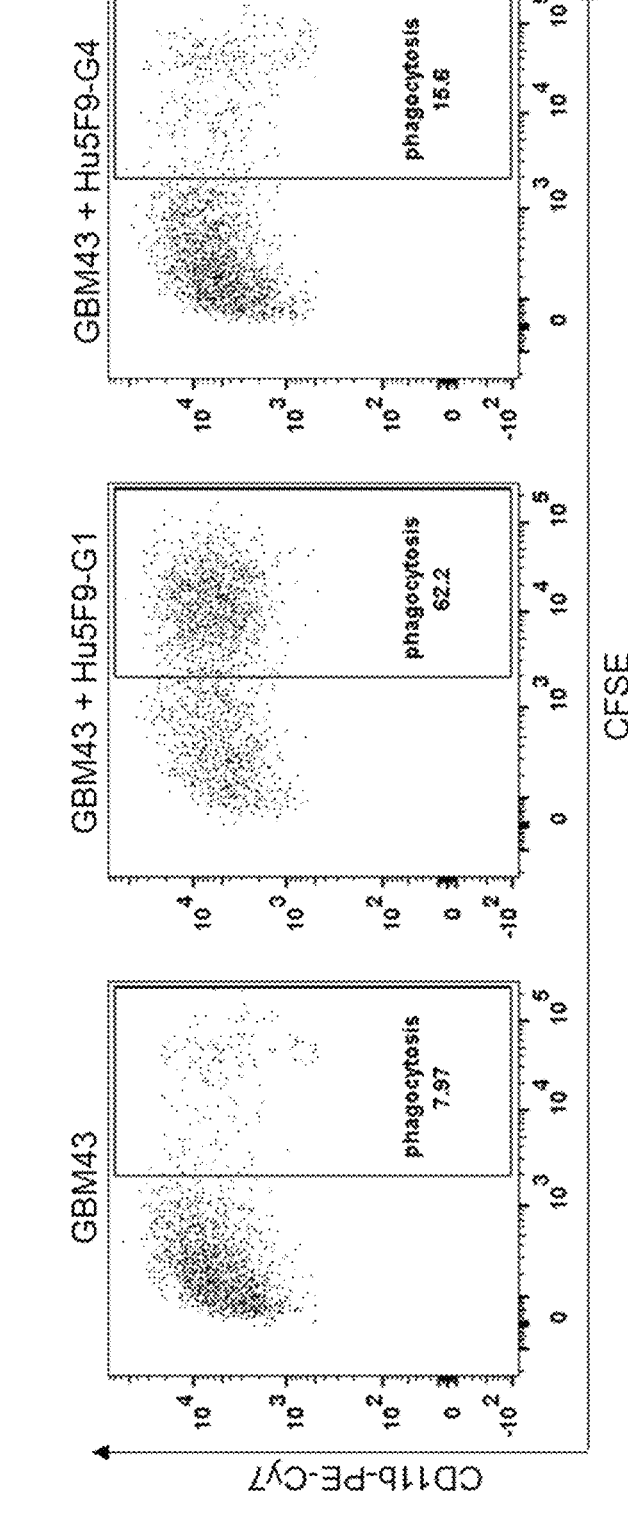
FIGS. 3A-3H demonstrate αCD47-G1 and αCD47-G4 induce phagocytosis of GMB cells by macrophages.
Figure 3B:
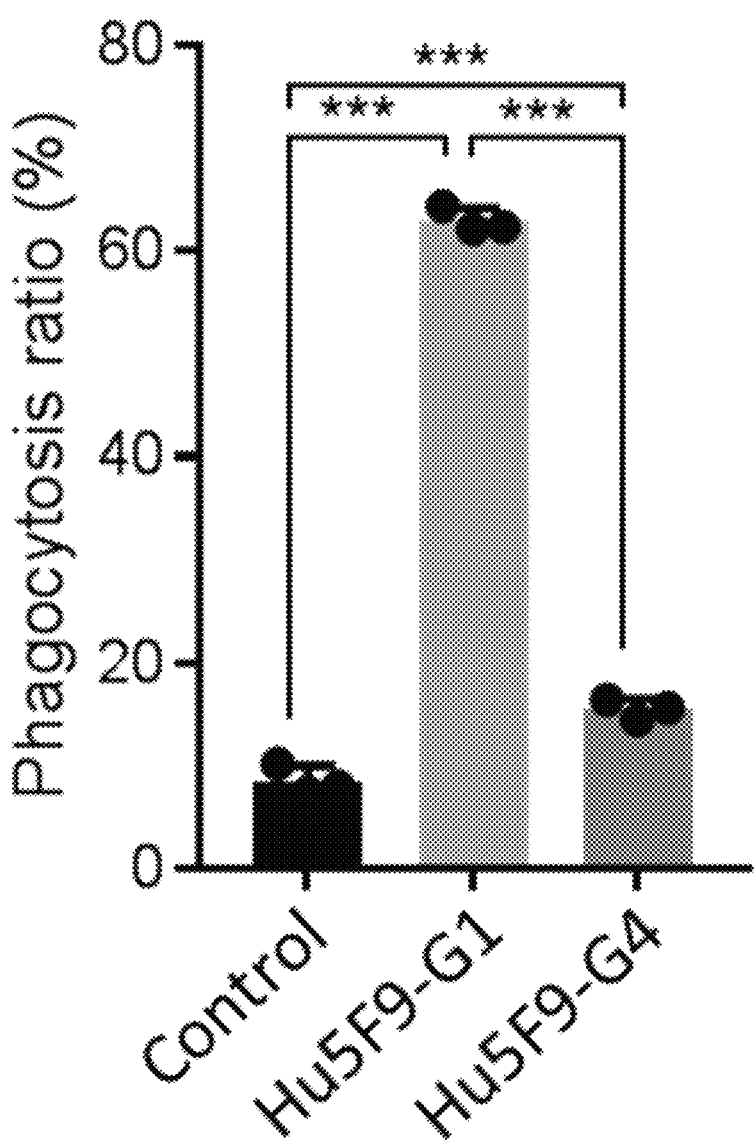
Figure 3C:
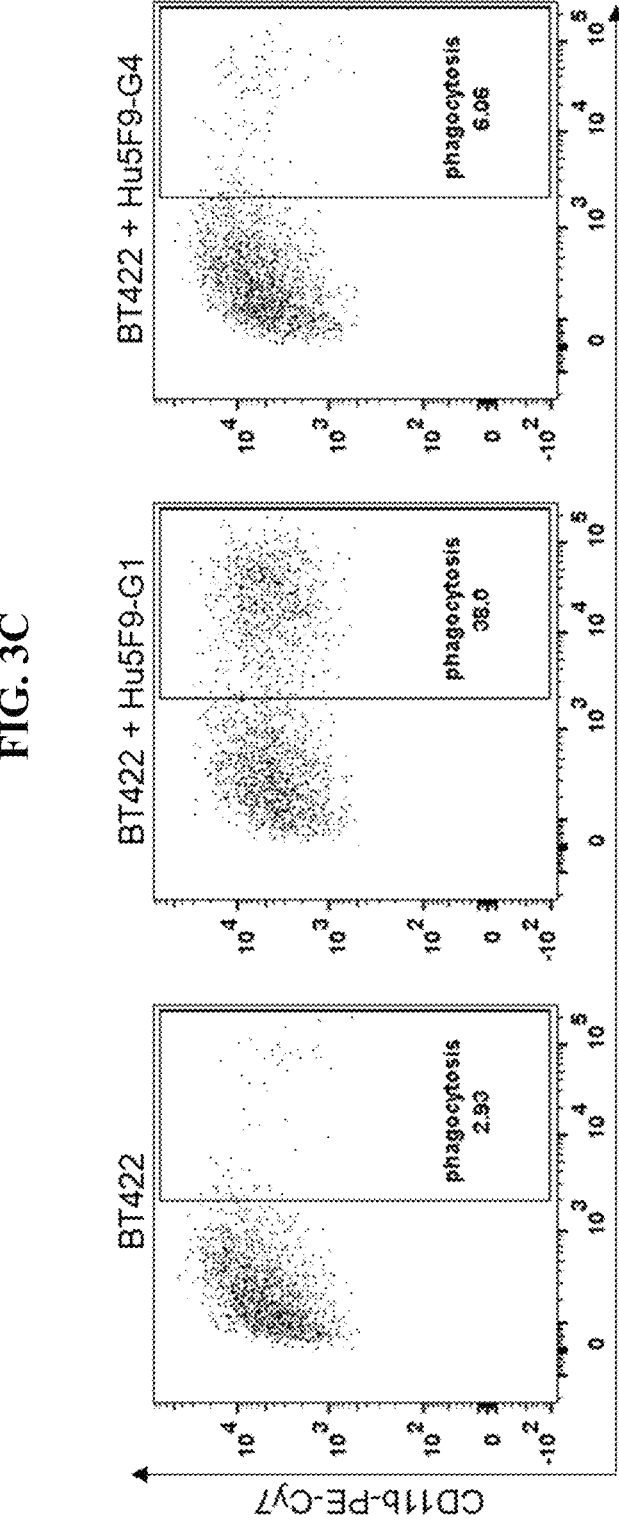
Figure 3D:
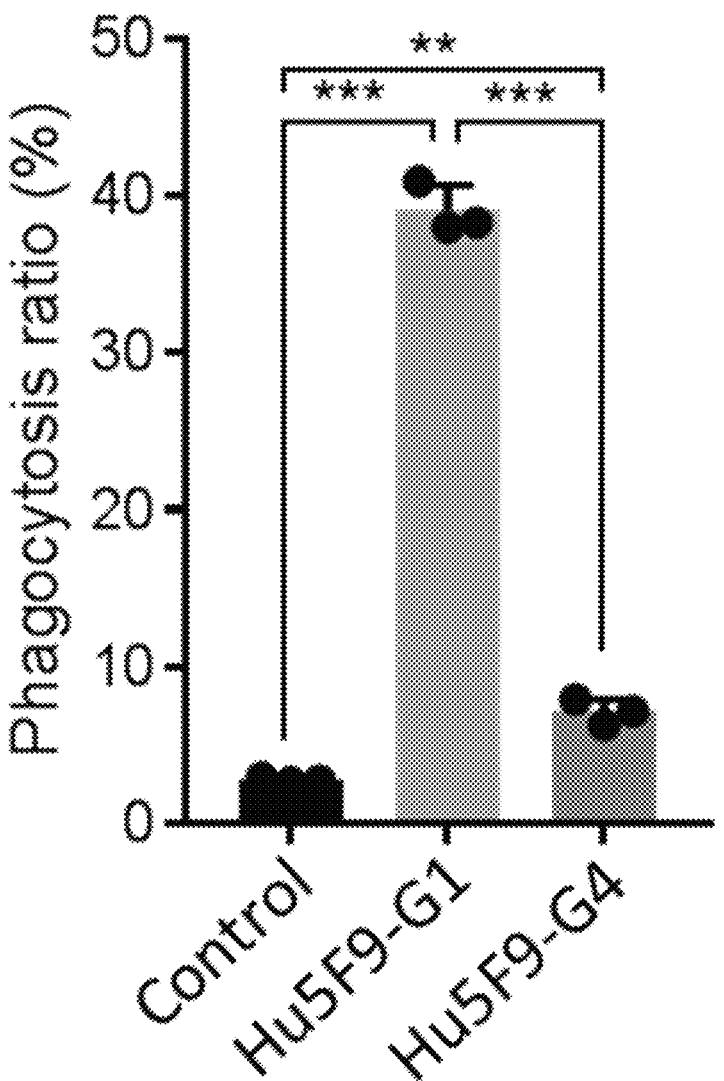
Figure 3E:
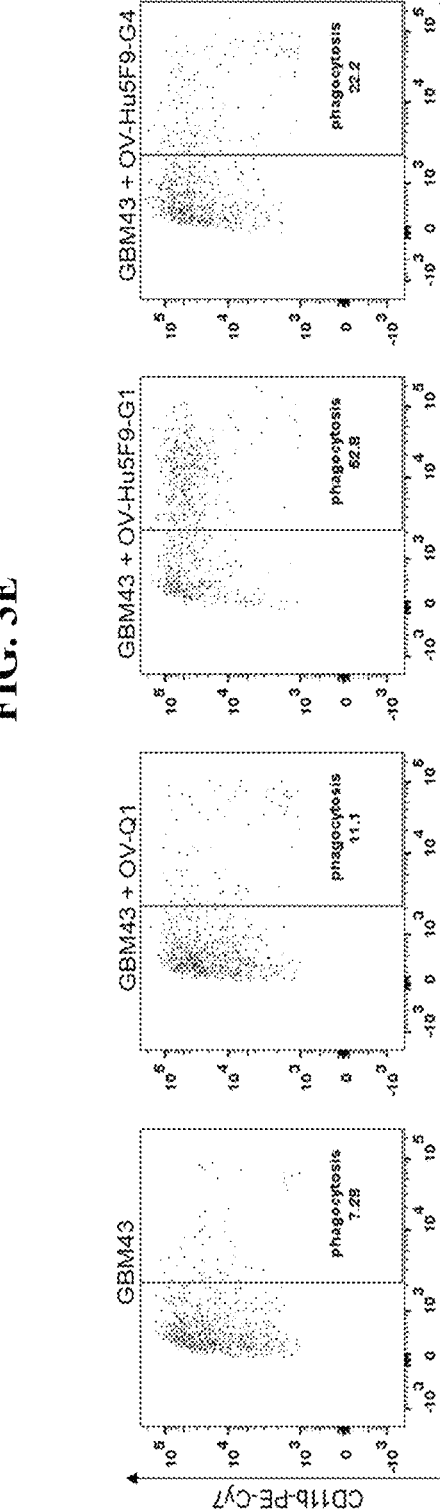
Figure 3F:
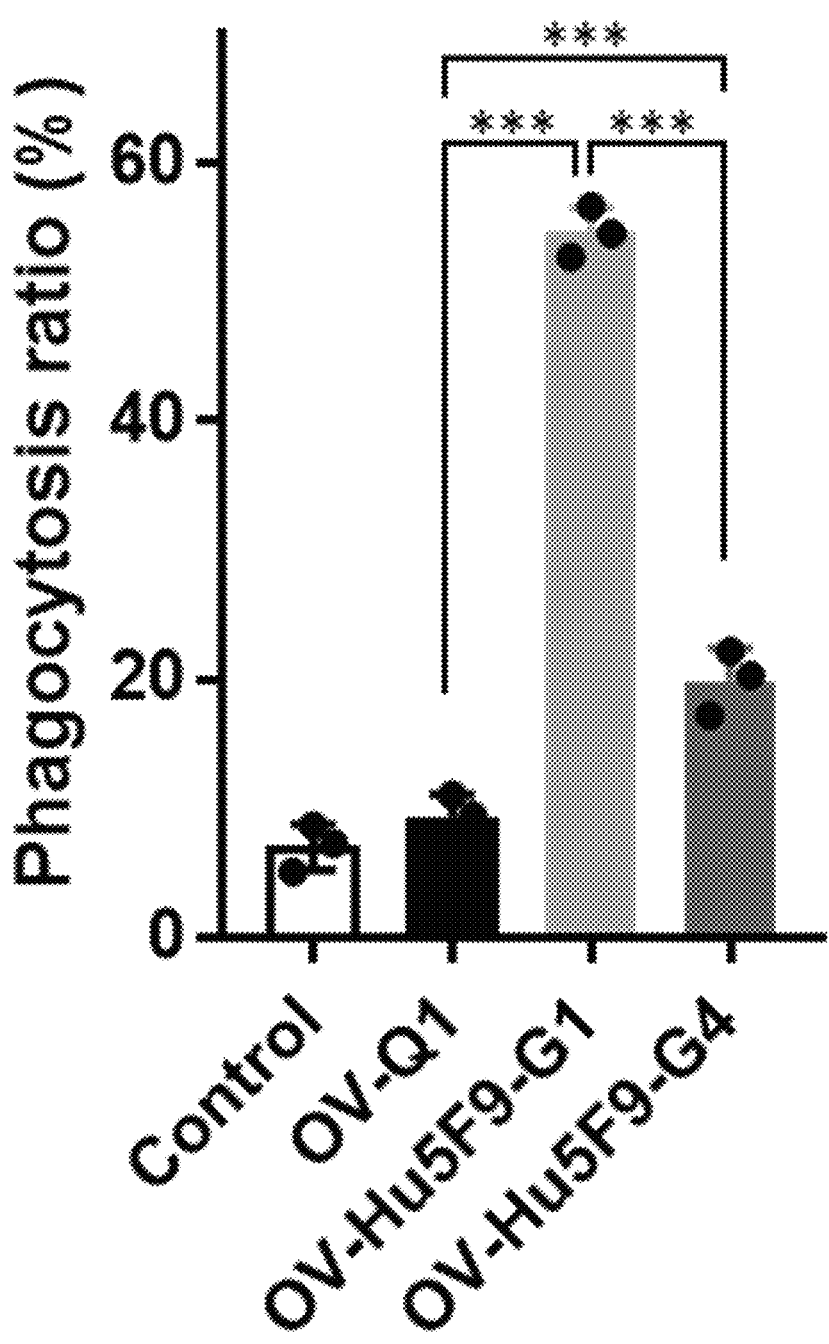
Figure 3G:
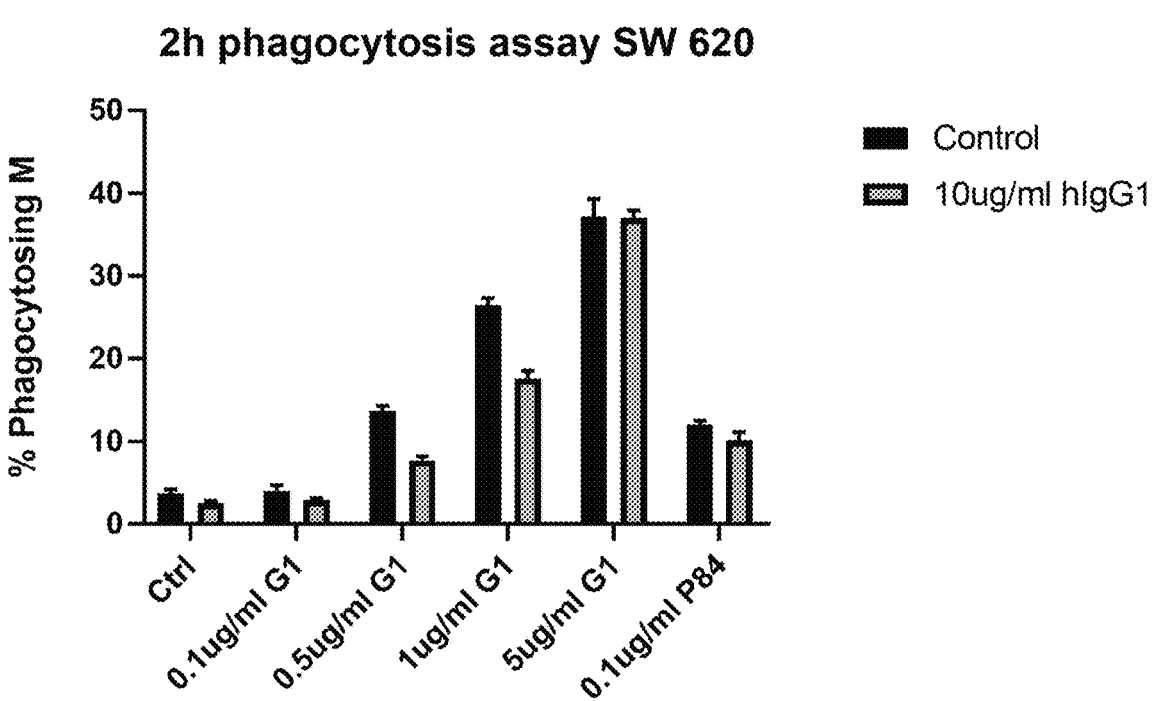
Figure 3H:
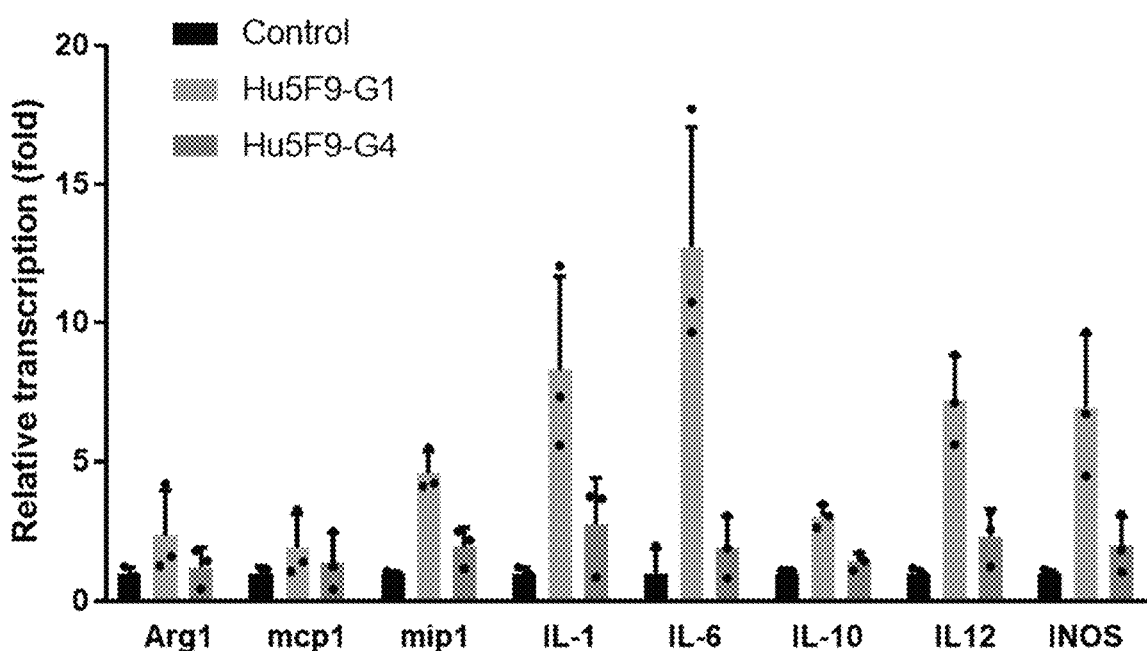

Next, the ability of αCD47-G1 and αCD47-G4 to modulate phagocytosis of GBM cells by macrophages was compared. For this purpose, mouse bone marrow derived-macrophages were used as effector cells, as performed by many other groups[22]. Patient-derived GBM cells GBM43 and BT422 were used as target cells and were labeled with CFSE and pre-incubated with αCD47-G1 or αCD47-G4 purified from lentivirally infected CHO cells. Flow cytometry results showed that both αCD47-G1 and αCD47-G4 induced a significantly higher level of phagocytosis against GBM43 and BT422 cells compared to the corresponding OV-Q1-infected GBM cells. Notably, the effect of αCD47-G1 on macrophage phagocytosis against GBM43 or BT422 cells was significantly higher than that observed for αCD47-G4 (FIG. 3A-D). IgG4-based antibodies have the effect of blocking CD47-SIRPα yet have a weak ADCP effect while IgG1-based antibodies block CD47-SIRPα and have a strong ADCP effect due to the difference between IgG1 and IgG4 antibodies. Consistent with this, the overall effect of αCD47-G1 was significantly higher than that of αCD47-G4. Compared to control derived from OV-Q1-infected GBM cells, the effect of the purified αCD47-G1 had a dramatic increase while the effect of the purified αCD47-G4 had a moderate increase (FIG. 3A-D). These data suggest that the phagocytosis increased by αCD47-G1 was mainly from ADCP and blocking CD47-SIRPα contributed substantially less. The phagocytosis assays were also repeated with the supernatants from OV-αCD47-G1, OV-αCD47-G4 or OV-Q1 infected U251T2 GBM cells. Consistent with the above results, the effect of OV-αCD47-G1 on ADCP was higher than that of OV-αCD47-G4. The effect of OV-αCD47-G1 is approximately three-fold of the effect of OV-αCD47-G4 (FIG. 3E, 3F). FIG. 3G shows phagocytosis assay performed with Fc receptor blocking. For blocking the Fc receptors, BMDM cells were incubated with isotype human IgG1 at the dose of 10 mg/ml for 30 min in advance. FIG. 3H shows cytokine gene transcription assay. BMDM were cocultured with GBM43 at the ratio of 1:1 with or without the presence of αCD47-G1 or αCD47-G4 for 6 hours. Then, total RNA was extracted and reverse-transcribed for detecting the transcription level of the indicated genes by real time PCR.

αCD47-G1 Induces Potent NK Cell-Mediated Antibody-Dependent Cellular Cytotoxicity (ADCC) Against GBM.

Figure 4A:
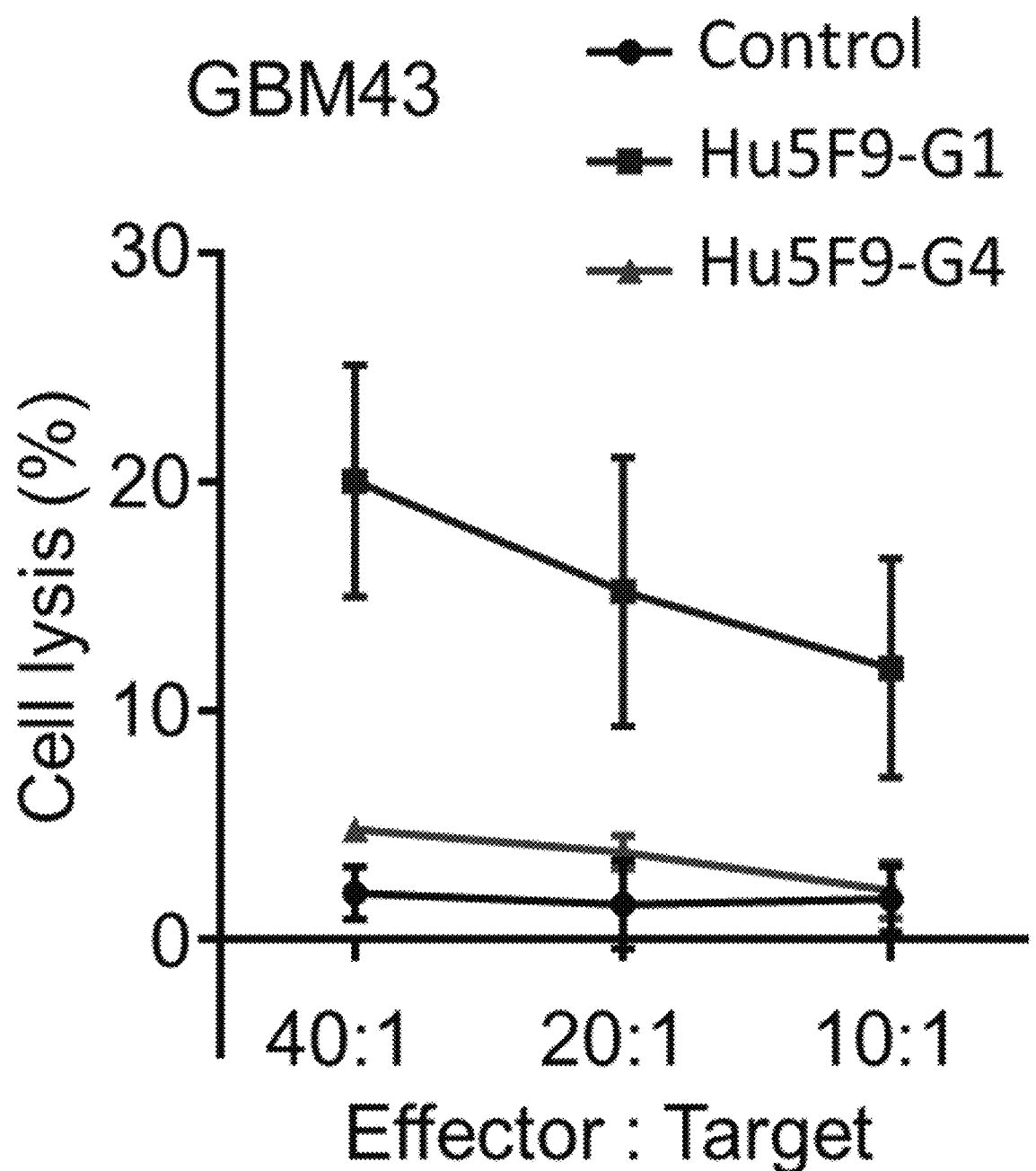
FIGS. 4A-4E demonstrate αCD47-G1 but not αCD47-G4 induces cytotoxicity of human NK cells against GBM cells.
Figure 4B:
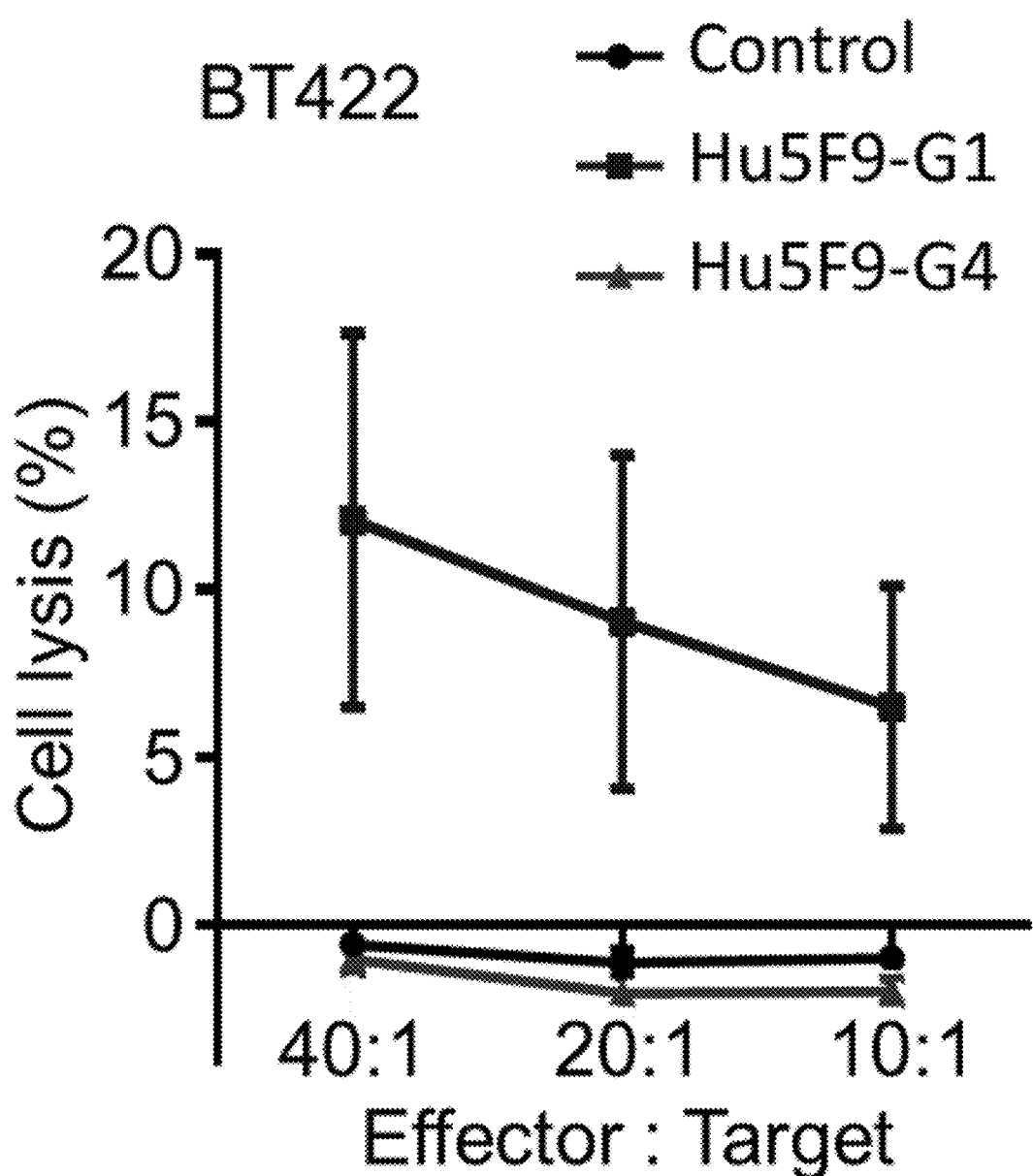
Figure 4C:
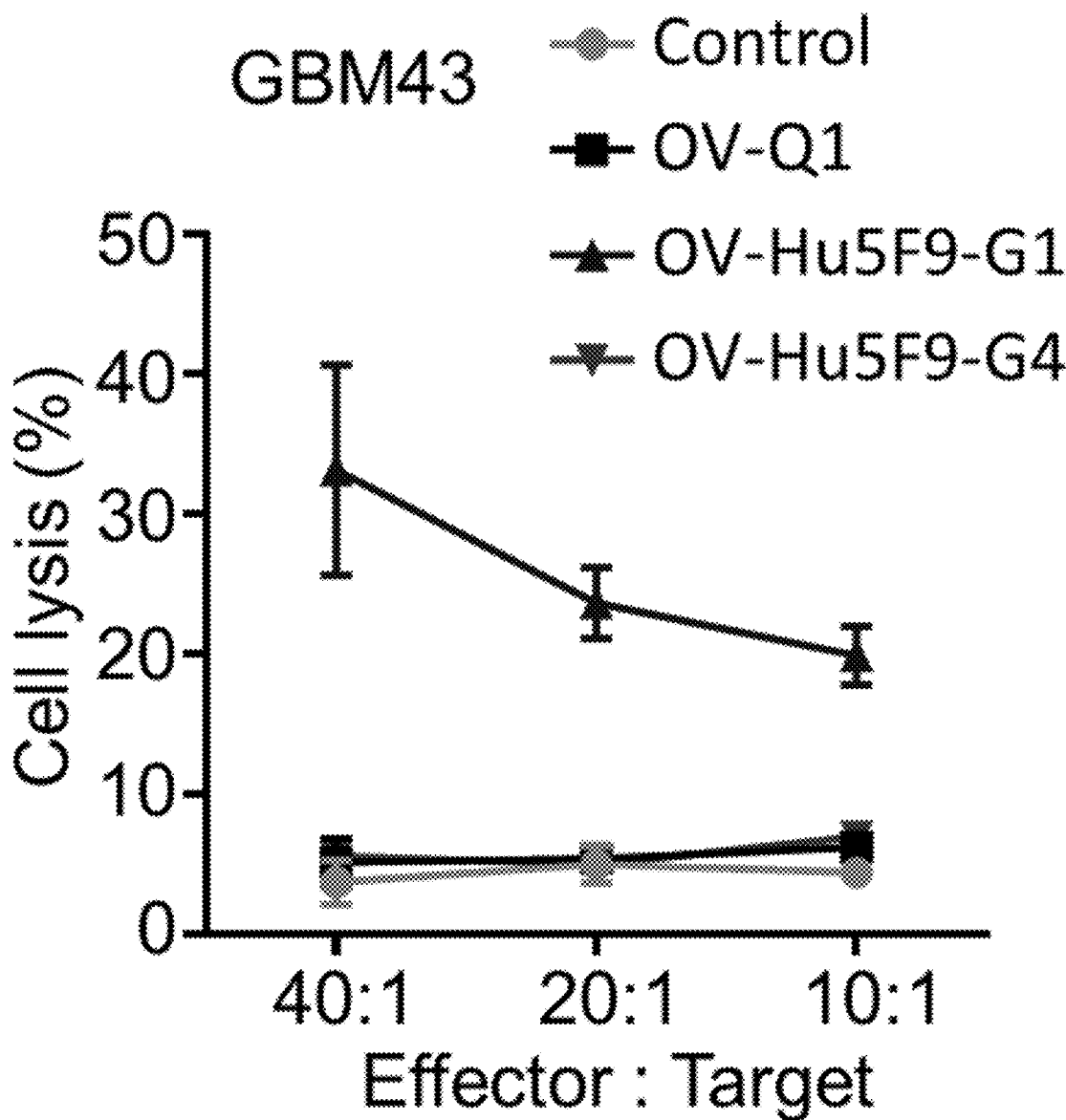
Figure 4D:
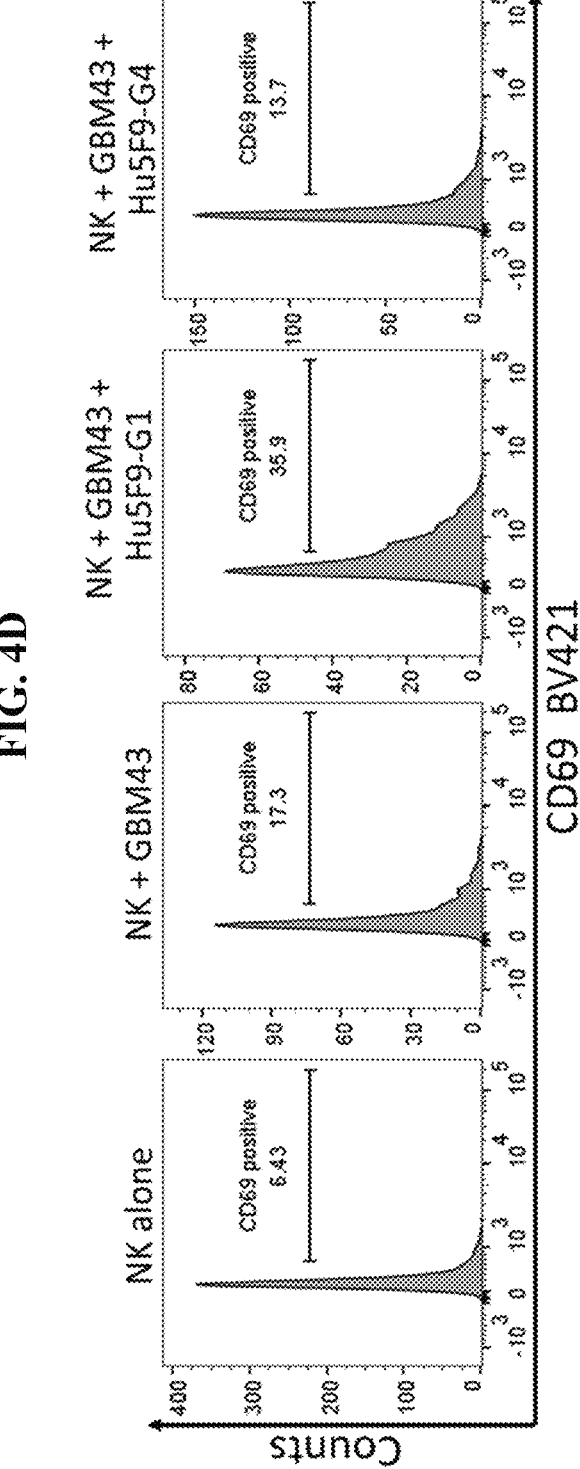
Figure 4E:
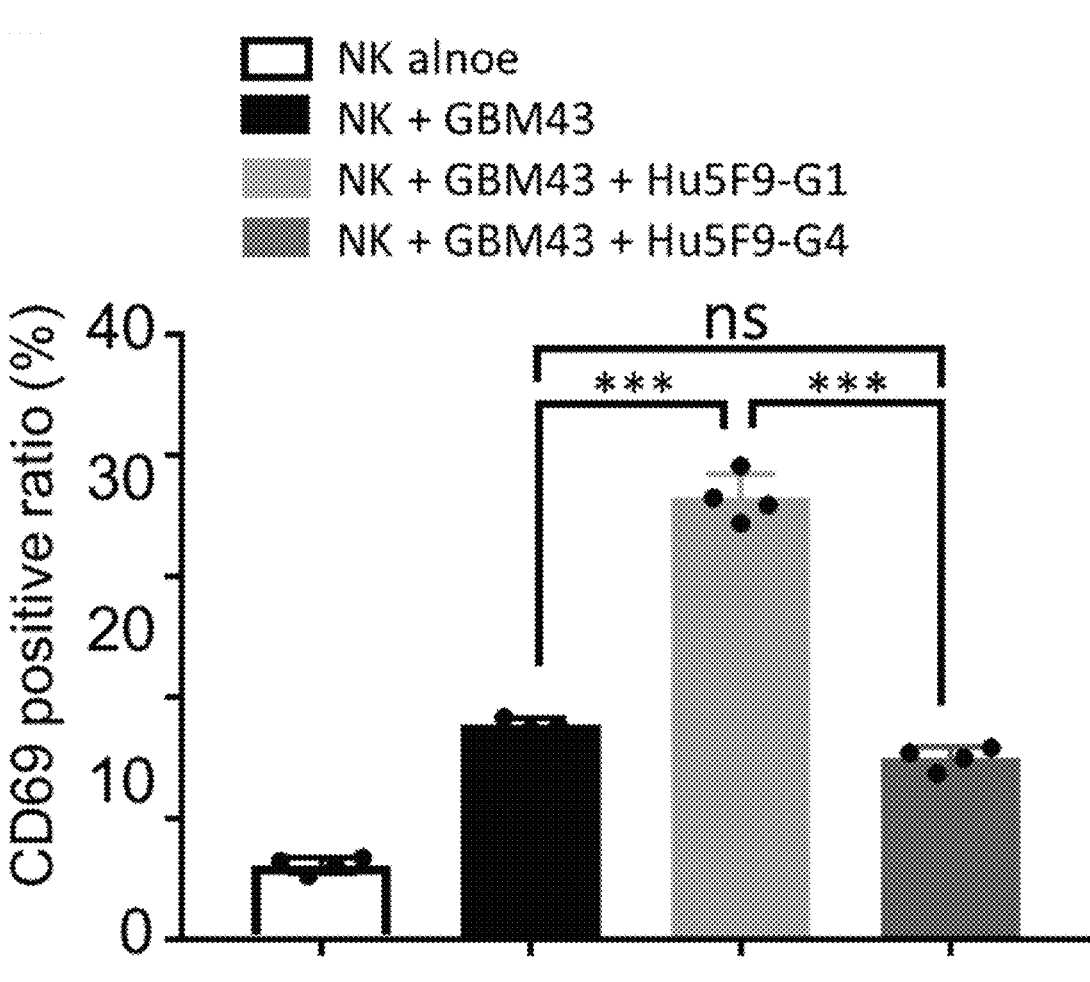

NK cells play a critical anti-tumor activity in cancers including GBM via natural cytotoxicity and ADCC, especially in combination with antibody therapy (see, for example, Ref. 31). In order to determine how Hu5F9-G1 or Hu5F9-G4 affects NK cell anti-tumor activity, freshly isolated human NK cells were used to measure the effect of the two antibodies on ADCC. Human GBM patients-derived tumor cells GBM43 and BT422 were used as target cells. The target cells were labeled with Chromium-51 ($^{51}$Cr) for 1 hour, and were then incubated with αCD47-G1, αCD47-G4 purified from supernatants of lentivirus-infected CHO cells or vehicle for 30 min. The effector NK cells and the target cells were then co-cultured at the ratios of 40:1, 20:1 and 10:1 for 4 hours. Released $^{51}$Cr was measured for evaluating the levels of NK cell cytotoxicity. The results showed that when GBM43 and BT422 were used as target cells, αCD47-G1 but not αCD47-G4 induced strong NK cell cytotoxicity (FIG. 4A, 4B). This experiment was repeated with the supernatants from OV-αCD47-G1- and OV-αCD47-G4-infected U251T2 GBM cells. The GBM43 cells incubated with the conditioned medium from OV-αCD47-G1-infected U251T2 GBM cells underwent substantially more cytolysis than those incubated with the medium from OV-Q1-infected U251T2 cells. However, no difference was found between conditioned media from OV-Q1- and OV-αCD47-G4-infected U251T2 GBM cells (FIG. 4C). NK cell activation induced by Hu5F9-G1 was also confirmed by measuring the expression of the activation marker CD69 on NK cells by flow cytometry. The results showed that αCD47-G1 but not αCD47-G4 dramatically increased the surface expression of CD69 on NK cells (FIG. 4D, 4E, 8C, 8D). To confirm that the effect of OV-αCD47-G1 was mediated by Fc receptor, blocking of the Fc receptors was found to reduce antitumor activity of αCD47-G1 secreted from GBM cells.

While Both OV-αCD47-G1 and OV-αCD47-G4 Improve Oncolytic Virotherapy, OV-αCD47-G1 Shows a Superior Effect.

Figures 5A, 5B:
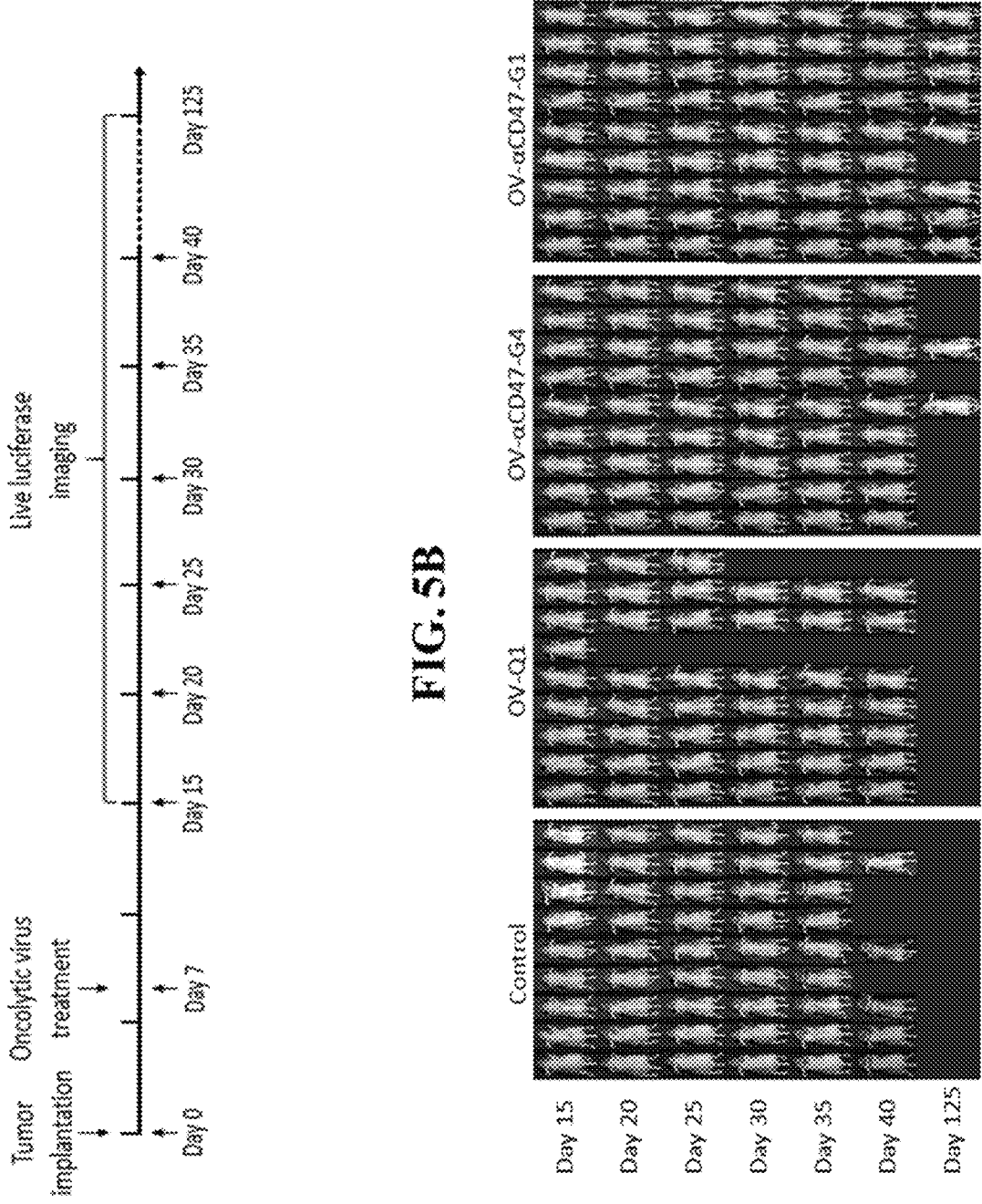
FIGS. 5A-5E shows a comparison of the effectiveness of OV-αCD47-G1 versus OV-αCD47-G4 to improve in vivo oncolytic virotherapy of GBM in an orthotopic model of human GBM.
Figure 5C:
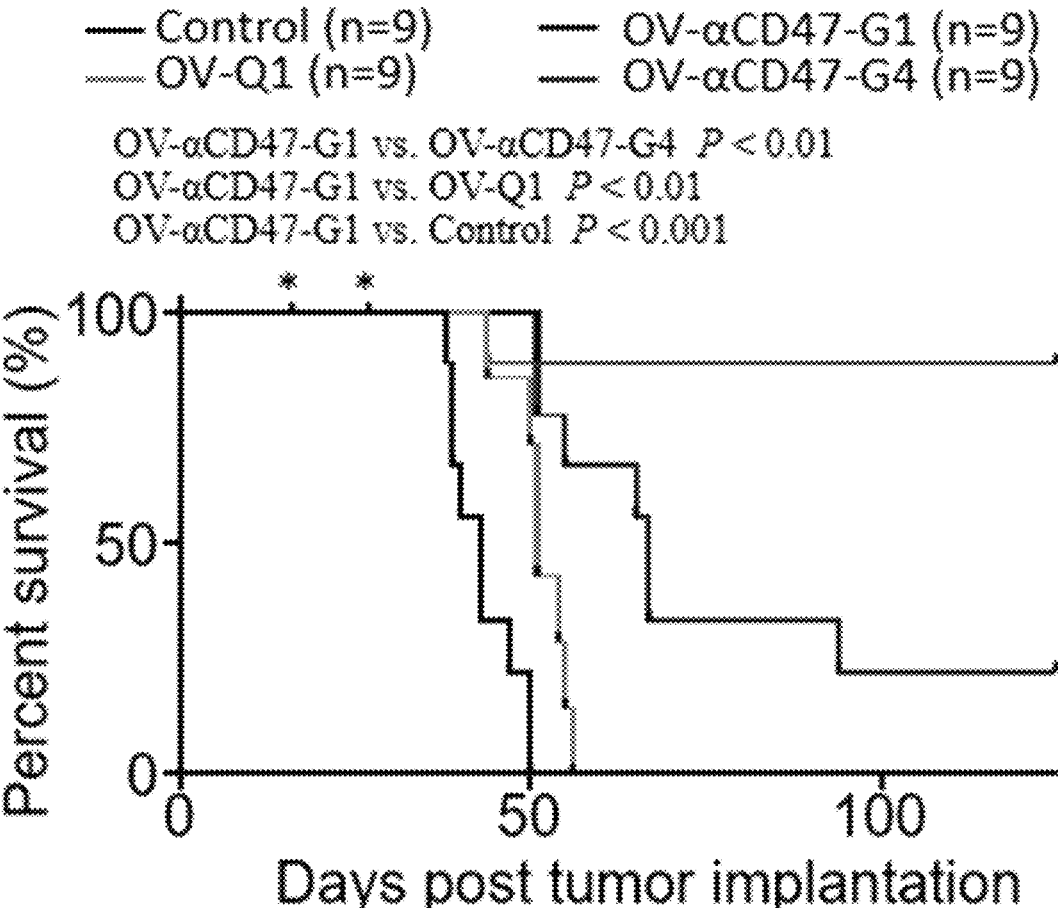
Figure 5D:
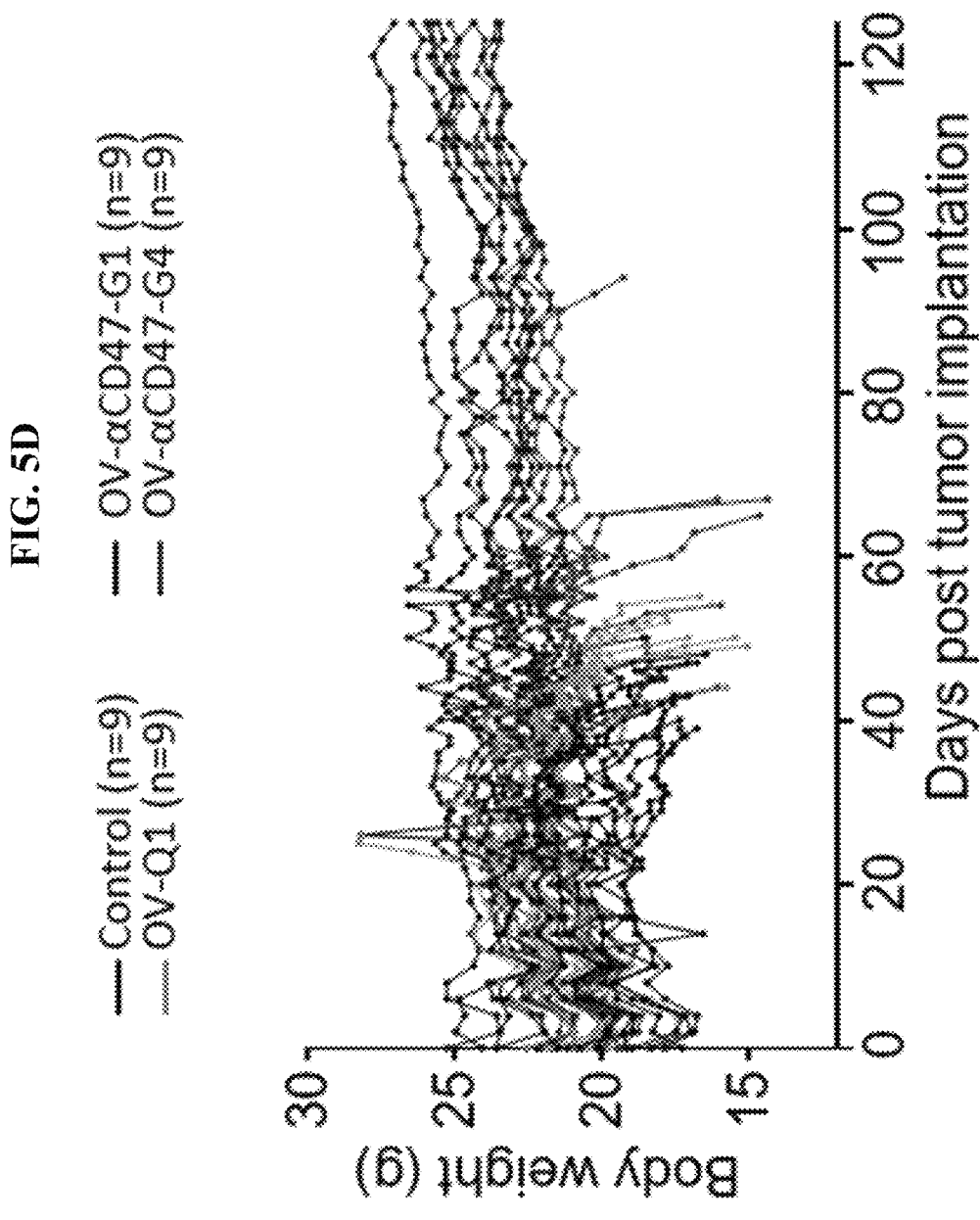
Figure 5E:
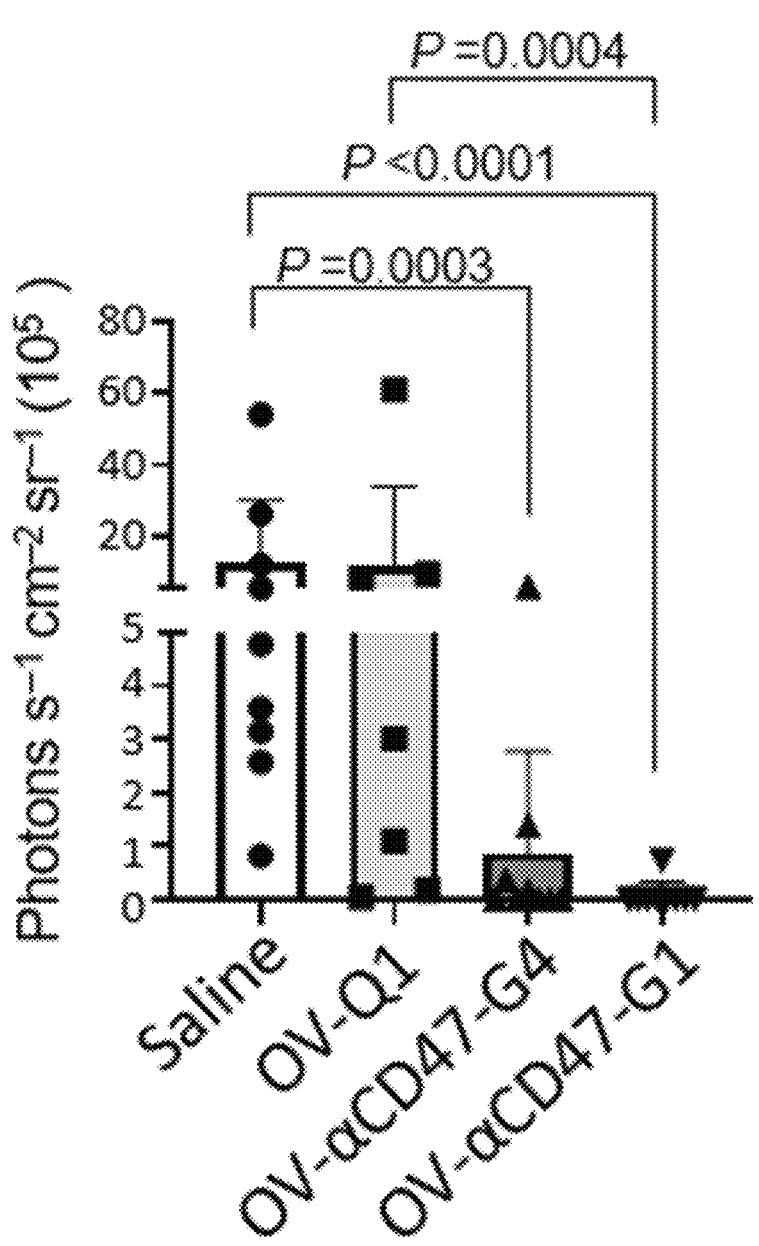
Figure 6A:
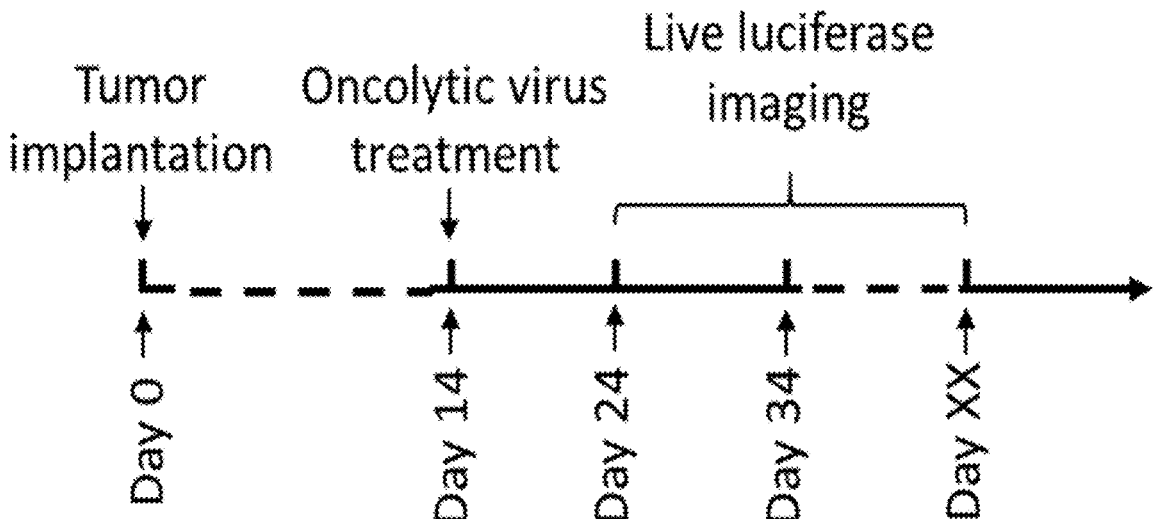
FIGS. 6A-6D demonstrate OV-αCD47-G1 is safer and more effective than the combination of OV-Q1 and i.p. administrated αCD47-G1.
Figure 6B:
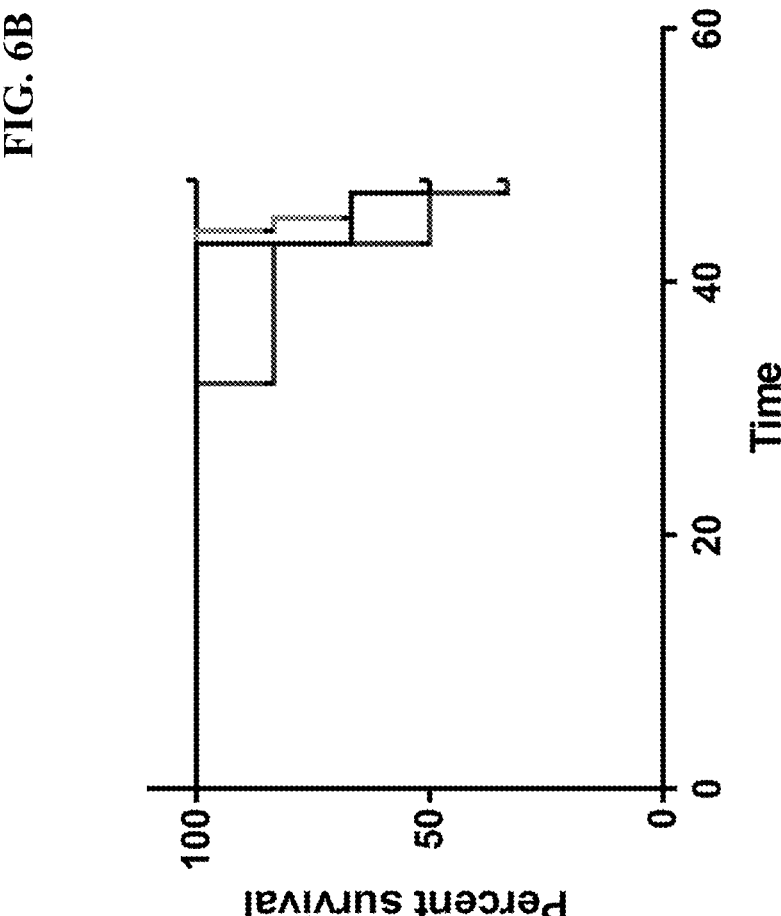
Figure 6C:
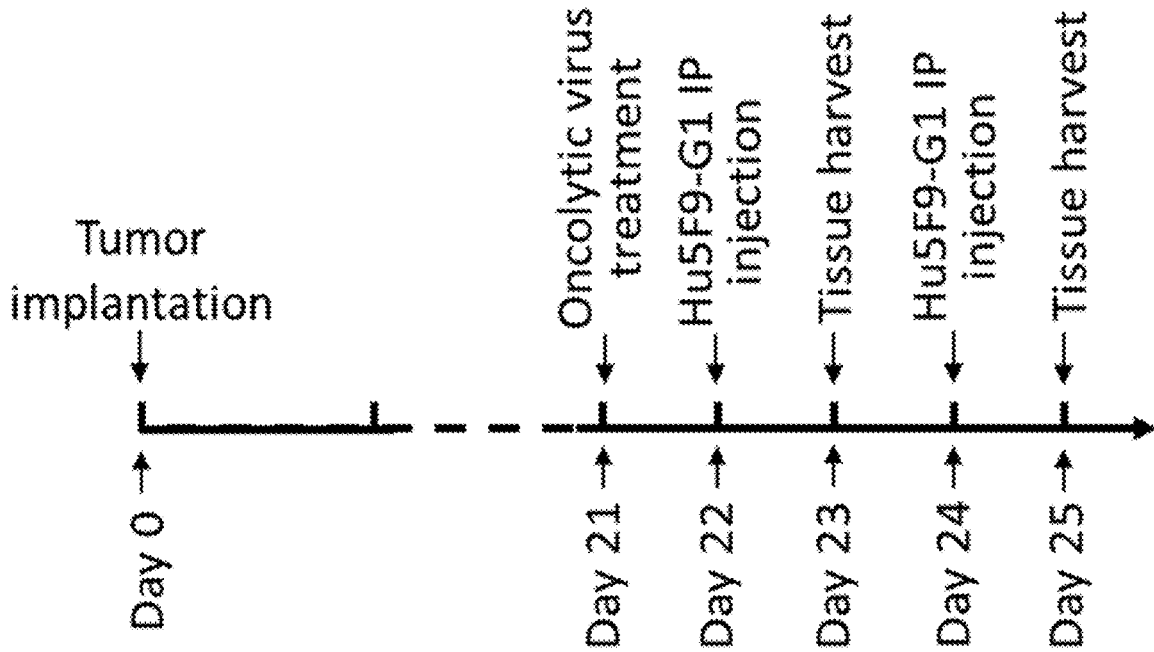
Figure 6D:
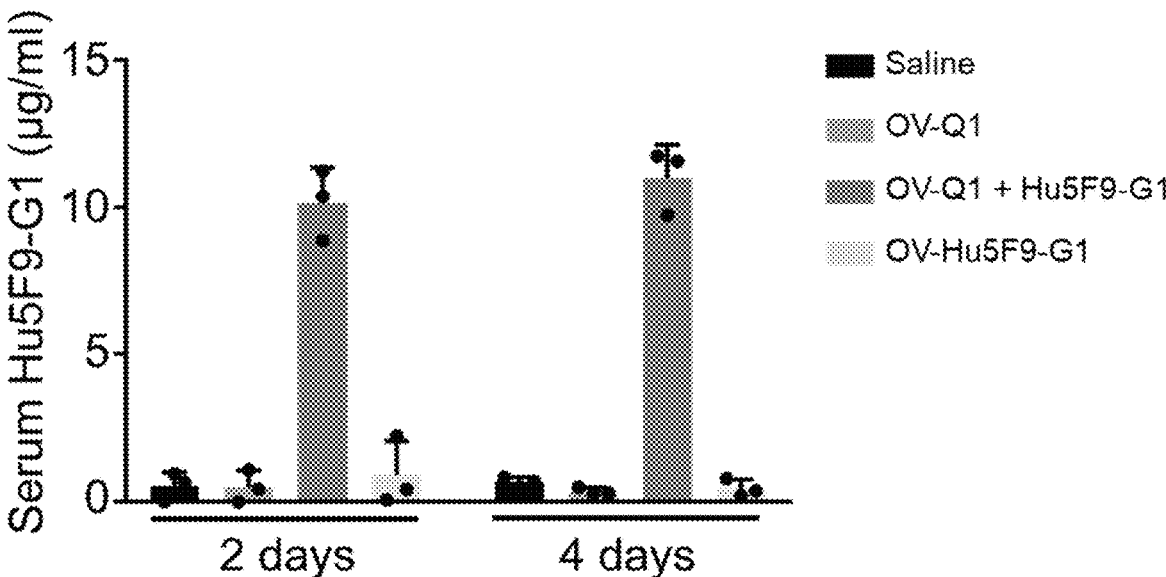

To evaluate the efficacy of OV-αCD47-G1 and OV-αCD47-G4 for the in vivo treatment of GBM, previously described xenograft GBM mouse models were utilized by intracranially (i.c.) injecting luciferase-expressing GBM43 cells into athymic nude mice (see, for example, Ref. 32). Seven days after tumor implantation, animals received an i.c. injection with OV-αCD47-G1, OV-αCD47-G4 or OV-Q1 at the dose of $2 \times 10^5$ PFU per mouse, or saline as a placebo control. Tumor progression was monitored by luciferase-based imaging every five days from day 15 post tumor implantation (FIG. 5A). Xenograft GBM mouse models were established by intracranially injecting $1 \times 10^5$ GBM43-FLL cells to athymic nude mice. Seven days later, mice were intratumorally injected with $2 \times 10^5$ PFU of OV-Q1, OV-αCD47-G1, OV-αCD47-G4 or vehicle. Mice were weighed every day, and luciferase-based image were taken every 5 day from day 15 post tumor implantation to evaluate tumor progression. OV-αCD47-G1 was significantly more effective than OV-αCD47-G4 at inhibiting the progression of GBM tumors in vivo and both were superior to OV-Q1 (FIG. 5B-D). OV-Q1 slowed GBM progression moderately as compared to vehicle control and prolonged the median survival from 43 days to 51 days. OV-αCD47-G4 treatment prolonged median survival time of the GBM mice compared to both saline control and OV-Q1 treatment. Eight out of nine mice from the OV-αCD47-G1 group and two out of nine mice from the OV-αCD47-G4 group survived over 125 days without GBM symptoms and exhibited no detectable luciferase signal (FIGS. 5B, C and E). Body weight recording of the experimental mice further indicated that the mice treated with OV-αCD47-G1 were healthier compared to mice in other groups at the late stage of the study with continuously increasing body weights (FIG. 5D)

OV-αCD47-G1 is Superior to OV-αCD47-G4 and to Separate Intracranial Delivery of OV and Systemic αCD47-G1 in Improving Outcome in an Immunocompetent GBM Model We next sought to evaluate the efficacy of OV-αCD47-G1 in an immunocompetent GBM mouse model. A modified CT2A mouse GBM model was used for this purpose. The mouse CT2A GBM cells were modified to express human CD47 for generating the CT2A-hCD47 cells. The purpose for this modification is allow the αCD47-G1 antibody to bind to the human CD47 expressed on CT2A-hCD47 GBM cells. By i.c. injection of CT2A-hCD47 cells into immunocompetent wild-type C57BL/6 mice, we established a GBM immunocompetent mouse model and repeated the survival study in FIG. 5 with slight modification (FIG. 18A). The treatment of these mice with OV-αCD47-G1 significantly prolonged their median survival when compared to those mice treated with OV-αCD47-G4, OV-Q1 or vehicle control (FIG. 18B). However, in contrast to the xenograft model, we did not see a significant difference from the mice treated with OV-αCD47-G4 and either OV-Q1 or vehicle control (FIG. 18B). Possible explanations for this include: (1) the human-CD47-mediated "don't eat me" signal may not function well in the immunocompetent C57BL/6 mice; (2) the murine macrophages still receive the murine-CD47-mediated "don't eat me" signal from the CT2A-hCD47 GBM that cannot be blocked by human αCD47-G1 or αCD47-G4; (3) human αCD47-G1 can still bind to a murine Fc receptor to induce ADCP or ADCC but αCD47-G4 cannot, as shown for other antibodies[33] Body weight recordings of the mice in the study supported the findings that OV-αCD47-G1 was the only effective treatment for the immune competent mouse GBM model (FIG. 18C).

Next, we repeated the survival study with the CT2A-hCD47 GBM mouse model to compare the effectiveness of i.c. administration of OV-αCD47-G1 against the combination of i.c. administration of OV-Q1 combined with continuous release of αCD47-G1 mAb into the GBM environment by an osmotic pump. For the purpose, we set up 5 different treatment groups of i.c. administration: Group 1, saline; Group 2, OV-Q1; Group 3, osmotic pump delivery of αCD47-G1; Group 4, a combination of OV-Q1 plus osmotic pump delivery of αCD47-G1 mAb and Group 5, OV-αCD47-G1. Three days post tumor implantation (day 3), the two groups with OV-Q1 injection (Groups 2 and 4) and the group with OV-αCD47-G1 injection (Group 5) received $2\times10^5$ PFU corresponding virus per mouse. On days 4 to 7, the two groups with an osmotic pump delivery of αCD47-G1 received the i.c. delivery of the antibody by the pump at the rate of 1.0 μg per hour for 72 hours, i.e. 24 μg per day, which is about 2-3 times of the amount produced by the injected virus, based the data from FIG. 1F. Mice in other groups received i.c. saline as control (FIG. 18D). As a single agent, compared to saline, both OV-Q1 and αCD47-G1 delivery by the pump showed a modest but not statistically significant improvement in mouse survival (FIG. 1E). The combination of OV-Q1 and αCD47-G1 delivery by the pump seems to be better than αCD47-G1 alone and the P value is on the boarder of significance (P=0.0737) but was not significantly different when compared to OV-Q1 alone. Consistent with other two animal models (FIGS. 5C and 21B), OV-αCD47-G1 significantly prolonged the survival of the GBM mice when compared to OV-Q1 (FIG. 18E). OV-αCD47-G1 is the best among all the tested groups and in particular is statistically superior to the combination of i.c. OV-Q1 and αCD47-G1 delivery by the pump. As the OV-αCD47-G1 therapeutic combines OV-Q1 and αCD47-G1 into a single agent, and the single agent shows therapeutic survival outcomes superior to αCD47-G1 alone, OV-Q1 alone, and their combination, the two-in-one single agent, i.e., an oncolytic virus expressing a full-length IgG1 anti-CD47 antibody is an innovative, convenient, and effective approach for the treatment of experimental GBM.

Figure 9:
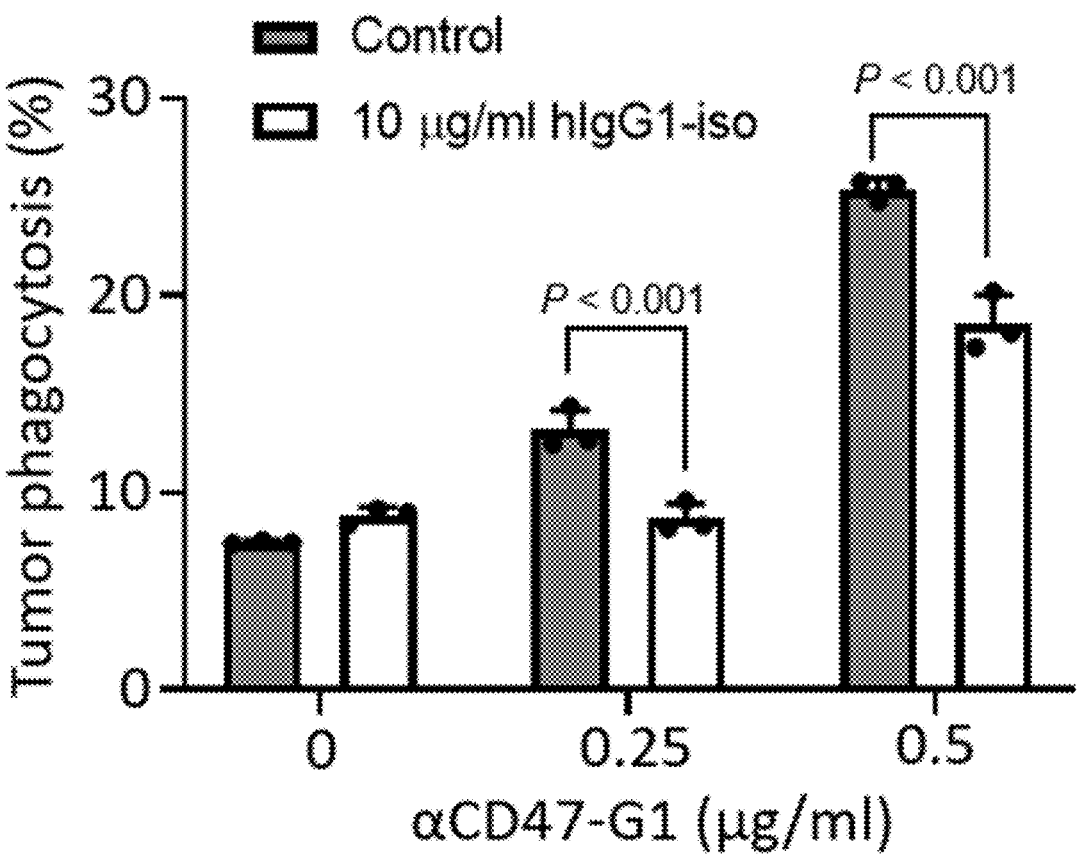
FIG. 9 shows percentage of BMDM phagocytosis of GBM43 cells (CD11b+CFSE+) assayed by flow cytometry. BMDM were incubated with vehicle control or human IgG1 at the dose of 10 μg/ml for 30 min prior to co-culture with GBM43 cells in the presence of increasing αCD47-G1 for 2 hours.
Figure 10:
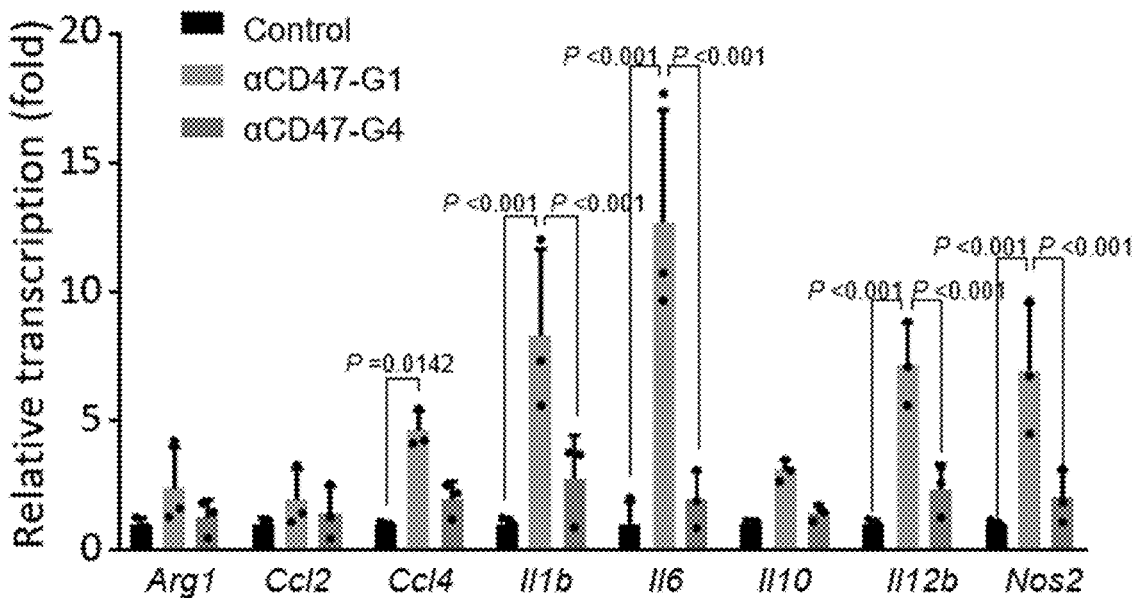
FIG. 10 shows expression levels of Arg1, Ccl2, Il1b, Il6, Il10, Il2b, and Nos2 where BMDM were cocultured with GBM43 cells at a ratio of 1:1 with or without αCD47-G1 or αCD47-G4 for 6 hours.

To prove that αCD47-G1 induces GBM phagocytosis via ADCP, we repeated the phagocytosis assay with Fc receptor blockade. Preincubating BMDM with high-dose (10 μg/ml) isotype human IgG1, which competes with αCD47-G1 to bind to Fc receptors, significantly inhibited αCD47-G1-induced GBM phagocytosis by BMDM (FIG. 9). We also found that αCD47-G1 but not αCD47-G4 dramatically activated transcription of typical macrophage cytokine genes of mouse BMDM that have been reported to response to IgG1 antibody (see, for example, Ref. 28), such as Il1b, Il6, Il10, Il12b and Nos2 (FIG. 10).

Figure 11:
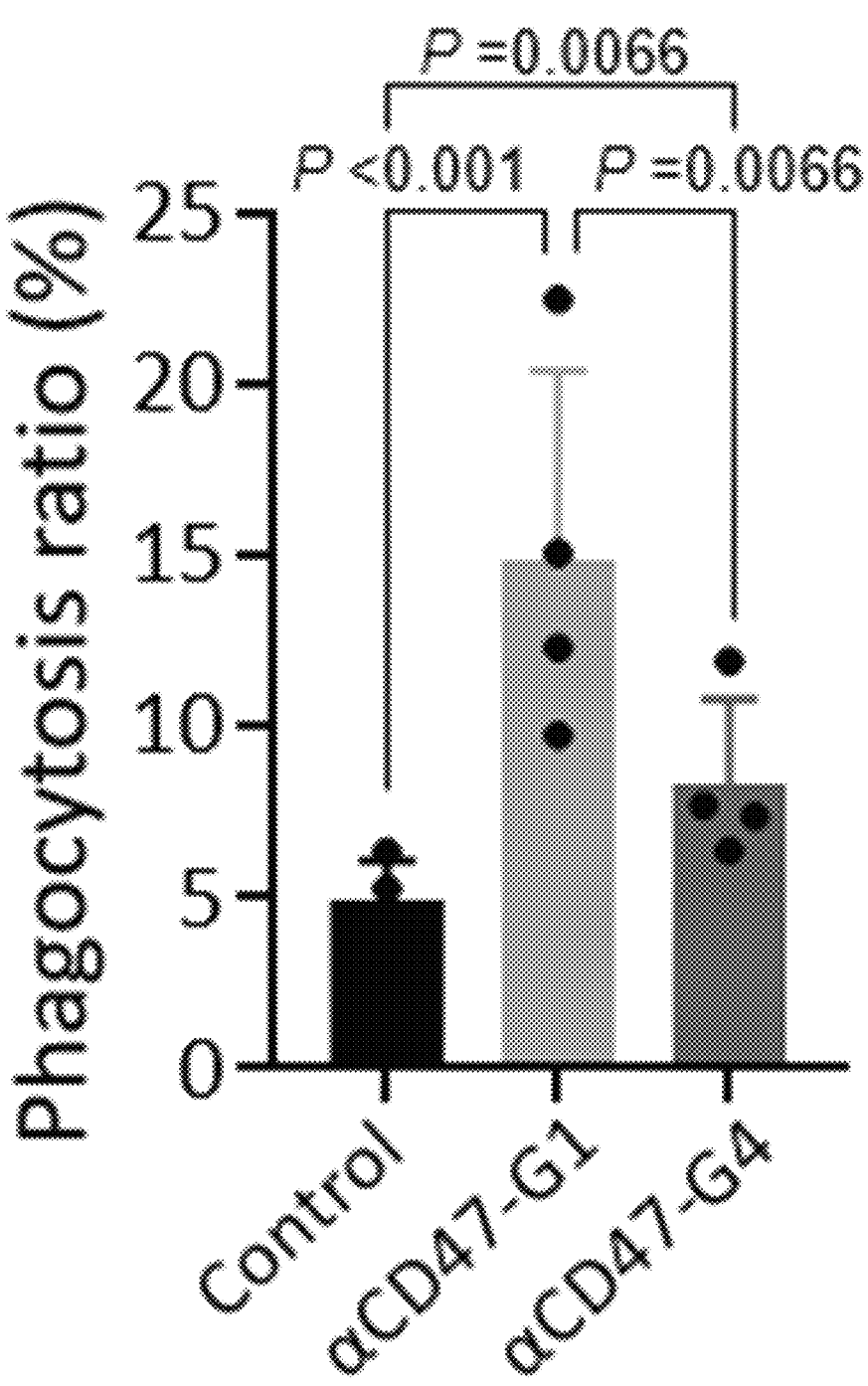
FIG. 11 shows the effect of 5 μg/ml of αCD47-G1 and αCD47-G4 purified from CHO cells on phagocytosis of GBM43 cells by primary human macrophages.
Figure 12:
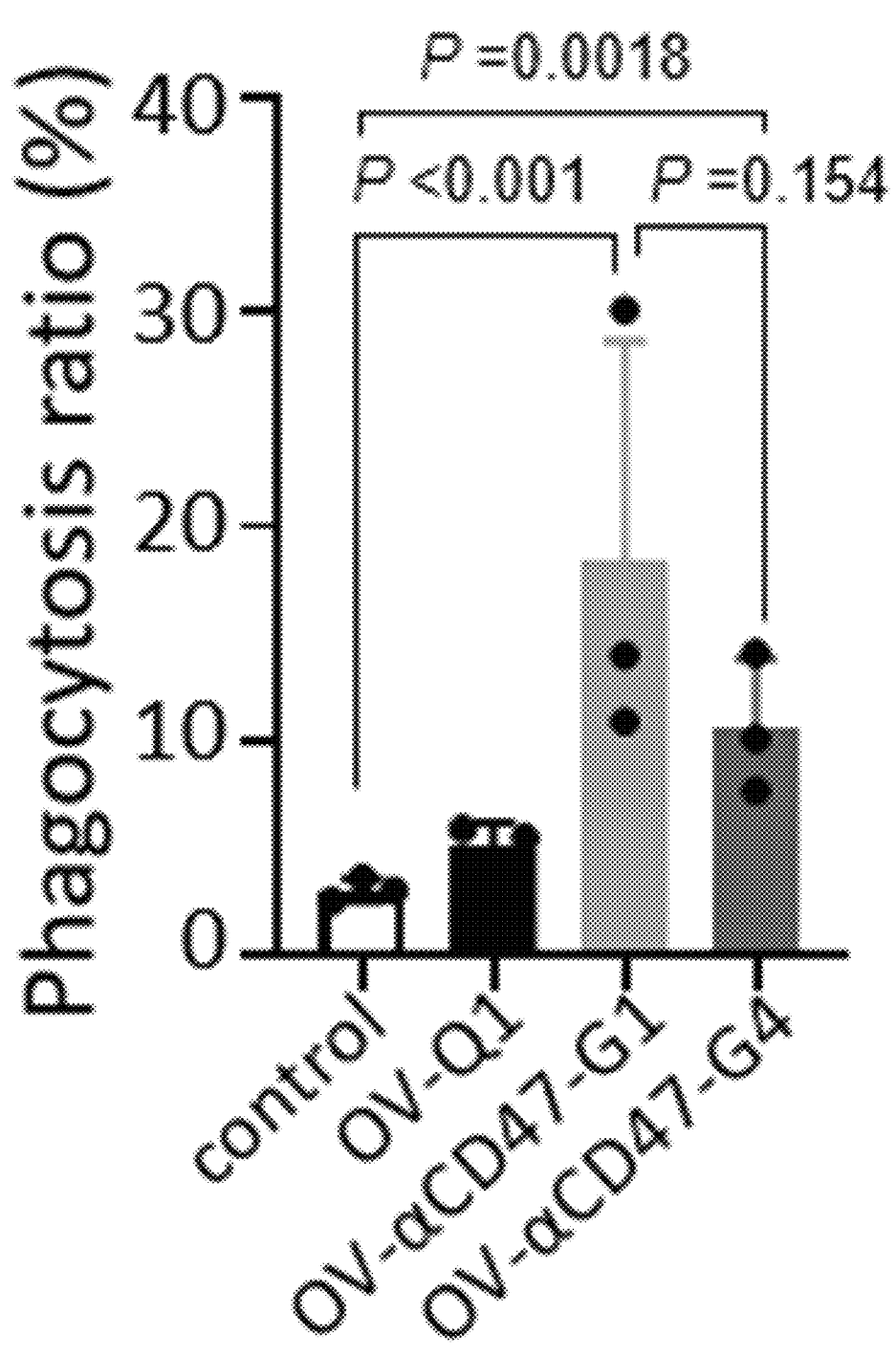
FIG. 12 shows shows the effect of conditioned media from OV-αCD47-G1- and OV-αCD47-G4-infected U251T2 human GBM cells on phagocytosis of GBM43 cells by primary human macrophages.

The effects of αCD47-G1 and αCD47-G4 on inducing the human macrophage phagocytosis were also determined. For this purpose, primary human donor-derived macrophages were used as effector cells, as previously reported by other groups (see, for example, Ref. 29). Patient-derived GBM43 GBM cells labeled with CFSE were used as target cells. Target cells were cocultured with the human primary macrophages at a ratio of 2:1 for 4 hours in the presence of αCD47-G1 or αCD47-G4 that purified from lentivirus-infected CHO cells. Similar to the results as we collected using mouse BMDM, compared to vehicle control, both αCD47-G1 and αCD47-G4 significantly enhanced the phagocytosis of GBM43 cells by human macrophages, although the effect of the former is more substantial than the latter due to having additional strong ADCP effect (FIG. 11). Similar results were found by using the unconcentrated supernatants from OV-αCD47-G1-, OV-αCD47-G4- or OV-Q1-infected U251T2 GBM cells. Both αCD47-G1 secreted by OV-αCD47-G1-infected cells and αCD47-G4 secreted by OV-αCD47-G4-infected cells significantly enhanced the phagocytosis of GBM43 cells by human macrophages, although the effect of the former is more substantial than the latter (FIG. 12). αCD47-G1 also activated the transcription of typical macrophage cytokine genes of human macrophages, such as IL1B, IL6, IL10, NOS2 (FIG. 13A) and IL12A (FIG. 13B).

For both murine and human macrophages, the increased phagocytosis effect of αCD47-G1 above vehicle control should be from both blockade of "don't eat me" signaling and ADCP while the effect above αCD47-G4 should be from ADCP only, as IgG1 rather than IgG4 antibodies can induce substantial ADCP via an Fc receptor-mediated effect, likely due to the distinct physical properties of IgG1 and IgG4 antibodies (see, for example, Ref. 30).

Comparison of Systemic i.v. Injection Versus Locoregional OV Delivery of the Anti-CD47 Antibody To evaluate the efficacy of delivering αCD47-G1 antibody to the GBM microenvironment by i.c. OV-αCD47-G1 versus systemic i.v. administration, we modified a previously described xenograft GBM mouse model by i.c. injecting $1\times10^5$ GBM43 cells into athymic nude mice (FIG. 14) (see, for example, Ref. 32). Twenty-one days after tumor implantation (day 0), mice were divided to four groups for i.c. administration: Group 1, saline; Group 2, OV-Q1; Group 3, a combination of OV-Q1 plus intraperitoneal (i.p.) delivery of αCD47-G1; and Group 4, OV-αCD47-G1. The viral dose for the two groups receiving an i.c. injection of OV-Q1 and the group receiving i.c. injection of OV-αCD47-G1 on day 21 was $2\times10^5$ plaque-forming unit (PFU) per mouse. Group 3 received i.p. αCD47-G1 at a dose of 150 μg per mouse on day 22. Mice in other groups received i.p. saline on day 22 as control. All mice were sacrificed on day 23 to determine the levels of the antibody in plasma by ELISA and in the central nervous system (CNS) by IHC (FIG. 14).

Mice with i.p. injection of αCD47-G1 (150 μg/mouse) had approximately 10 μg/ml of αCD47-G1 detected in the plasma, while Groups 1, 2 and 4 had no or little αCD47-G1 detected in the plasma (FIG. 15A). Brains isolated from the experimental mice were used for histologic study. H&E staining was performed to distinguish GBM tissues from normal brain tissues (FIGS. 15B and C). The immunohistochemical staining with an anti-HSV antibody, anti-human Fc antibody, anti-CD11b or anti-NKp46 antibody indicated oHSV-infected areas, presence of αCD47-G1, distribution of macrophages or NK cells, respectively. The anti-human Fc staining showed that there was a measurable amount of αCD47-G1 detectable in the brains of the mice treated with OV-αCD47-G1 but no anti-human Fc staining was found in the brains of those that were i.c. treated with saline or OV-Q1 or in mice that received i.p. injections of αCD47-G1 (FIGS. 15B and C). The anti-human Fc staining localized in the same area of the anti-HSV staining in the brains treated with OV-αCD47-G1. The results showed that CDT 1b(+) macrophage and NKp46(+) NK cell infiltration increased only in the tumor-bearing hemispheres compared to the non-tumor hemispheres. The macrophages and NK cells in the brains of saline-treated mice were mainly located at the surrounding area of the entire tumor but rarely infiltrated into the central area of the tumor. However, treatment with OV-Q1 or OV-αCD47-G1 substantially increased intratumoral infiltration of CD11b(+) macrophages and NKp46(+) NK cell (FIGS. 15B and C).

To confirm our findings, we repeated this experiment with some modifications: performing i.p. administration of αCD47-G1 or saline twice (once on day 22 and another on day 24) and sacrificing the mice on day 25 without other modifications to the treatment protocol (FIG. 16). Similar results were observed. Plasma αCD47-G1 (approximately 10 μg/ml) was only detectable after i.p. administration of αCD47-G1 (FIG. 17A). The enhancement of intratumoral infiltration of CD11b (+) macrophages and NKp46(+) NK cells induced by oHSV treatment was somewhat more obvious compared to the experiment performed in FIGS. 15B and C (see FIGS. 17B and C). Our data demonstrate that αCD47-G1 was not only detectable at 2 but also 4 days post OV-αCD47-G1 treatment in the OV-αCD47-G1 treated brains rather than the other groups (FIGS. 15B and C), suggesting continuous releasing of αCD47-G1 from OV-αCD47-G1-infected GBM cells.

OV-Hu5F9-G1- or OV-Hu5F9-G4-Infected A2780 Cells Secrete a Full-Length Anti-CD47 Antibody.

Firstly, we detected CD47 expression on A2780, the human ovarian cancer cell line and observed that CD47 was expressed on the surface of A2780 cell line. For the blocking assay, A2780 cells were firstly incubated with αCD47-G1 or αCD47-G4 at gradient concentrations. Then the cells were stained with a BV786-conjugated anti-CD47 antibody. Results showed a similar dose-dependent decrease of BV786 signal when cells were preincubated with αCD47-G1 and αCD47-G4, indicating that αCD47-G1 and αCD47-G4 have a similar CD47 blocking capacity (FIG. 19). OV-αCD47-G1- and OV-αCD47-G4 were constructed by inserting the coding genes of αCD47-G1 and αCD47-G4 into the oncolytic herpes virus backbone (OV-Q1) respectively. The inserted genes of anti-CD47 antibody were driven by the virus immediately early gene promoter IE4/5 to get a high-level expression after infection (FIG. 20). For testing the anti-CD47 antibody yield of OV-αCD47-G1- and OV-αCD47-G4-infected cells, human ovarian cancer cells, A2780 cells, were saturated infected by OV-αCD47-G1 and OV-αCD47-G4 at the MOI of 2. Anti-CD47 antibodies were detected in the supernatant of infected cells as soon as 6 hours after infection. and the yield of anti-CD47 antibody reached over 5 ug/ml at 24 hours after infection. Then we tested if the insertion of anti-CD47 antibody coding gene affect the oncolytic effect of OV-αCD47-G1 and OV-αCD47-G4. A2780 cells were infected with different titers of OV-αCD47-G1, OV-αCD47-G4 or the parental virus (OV-Q1). There was no obvious difference in cell death was observed among that caused by infection of OV-αCD47-G1, OV-αCD47-G4 or OV-Q1. Therefore, the insertion of αCD47-G1 and αCD47-G4 coding genes does not affect the oncolytic ability of OV-αCD47-G1 and OV-αCD47-G4.

αCD47-G1 Activates the Antitumor Effect of Macrophages

For testing the macrophage phagocytosis activation effects of αCD47-G1 and αCD47-G4, human primary macrophages were isolated for using as effector cells. Human ovarian cancer cells A2780 were used as target cells. The target cells were cocultured with the human macrophages at the ratio of 2:1 for 4 hours in the presence of purified αCD47-G1 or αCD47-G4. The phagocytosis results showed that compared to vehicle control, αCD47-G1 dramatically, while αCD47-G4 moderately enhanced the phagocytosis of human macrophages against A2780 cells (FIG. 21A). The supernatants from OV-αCD47-G1-, OV-αCD47-G4- or OV-Q1-infected A2780 cells were used to repeat this experiment. Similar results were observed that compared to the supernatant from OV-Q-infected cells, the supernatant from OV-αCD47-G1-cells significantly supernatant enhanced the phagocytosis effect of human macrophages against A2780 cells, while that from OV-αCD47-G4-infected cells showed moderate function (FIG. 21B).

We also tested the effect of αCD47-G1 and αCD47-G4 on mouse macrophage phagocytosis activation. Bone marrow derived macrophages (BMDMs) isolated from BALB/c mice were used as effector cells. CFSE labeled human ovarian cancer cells A2780 were used as target cells. The target cells were cocultured with the BMDMs at the ratio of 2:1 for 4 hours in the presence of purified αCD47-G1 or αCD47-G4. The phagocytosis results showed that compared to vehicle control, αCD47-G1 significantly activated the phagocytosis function of mouse BMDMs against A2780 cells. However, αCD47-G4 has moderate effect on mouse BMDM phagocytosis activation (FIG. 21C). The supernatants from OV-αCD47-G1-, OV-αCD47-G4- or OV-Q1-infected A2780 cells were used to repeat this experiment with mouse BMDMs. Both αCD47-G1 secreted by OV-αCD47-G1-infected cells and αCD47-G4 secreted by OV-αCD47-G4-infected cells significantly enhanced the phagocytosis of mouse BMDMs against A2780 cells, although the effect of the former is more substantial than the latter due to αCD47-G1 having additional strong ADCP effect (FIG. 21D).

The effect of αCD47-G1 and αCD47-G4 on regulating the cytokine release of human macrophages were also tested. Human macrophages were incubated with αCD47-G1, αCD47-G4 or vehicle for 6 hours. Then the total RNA was isolated for measuring the gene transcription level by real time PCR. The results showed that αCD47-G1 dramatically activated the transcription of some typical macrophages cytokine genes such as IL6, IL10, iNOS and IL12 (FIGS. 22A and 22B).

OV-αCD47-G1 Activates the Antitumor Effect of NK Cells

To determine the effect of αCD47-G1 and αCD47-G4 on NK cell anti-tumor activity, we used freshly isolated human NK cells as effector cell and ovarian cancer cells as target cells to perform NK cell cytotoxicity assays. Chromium-51 pre-labeled target cells were incubated with purified αCD47-G1 or αCD47-G4. Then the effector NK cells were cocultured with the pretreated target cells at different ratios for 4 hours. The release of chromium-51 was measured for evaluating the cytotoxicity. The results showed that αCD47-G1 but not αCD47-G4 induced strong NK cell cytotoxicity against ovarian cancer cells (FIG. 23A). Then the supernatants from OV-Q1-, OV-αCD47-G1- and OV-αCD47-G4-infected A2780 cells were used to repeat this experiment. Consistent results were observed. Only the supernatant from OV-αCD47-G1- but not that from OV-αCD47-G4-infected A2780 cells induced strong NK cell cytotoxicity compared to the OV-Q1 supernatant (FIG. 23B). The NK cell activation effect of αCD47-G1 was also confirmed by measuring the expression of the NK cell activation marker CD69 with flow cytometry. The results showed that with the presence of tumor cells, αCD47-G1 but not αCD47-G4 significantly increased the surface expression of CD69 on NK cells (FIG. 23C). The similar results were also found when using the supernatants from OV-Q1-, OV-αCD47-G1- and OV-αCD47-G4-infected A2780 cells. Only the supernatant from OV-αCD47-G1- but not OV-αCD47-G4-infected cells significantly increased the surface expression of CD69 on NK cells (FIG. 23D). We also measured the granzyme B production of NK cells. Our data showed that with the presence of A2780 cells, αCD47-G1 significantly promoted the granzyme B production of NK cells compared to control group, while αCD47-G4 showed slightly effect on that (FIG. 23E).

OV-αCD47-G1 Improves the Therapeutic Efficacy Against Ovarian Tumor

To evaluate the efficacy of OV-αCD47-G1 and OV-αCD47-G4 for the in vivo treatment of ovarian cancer, we utilized a previously described xenograft model of ovarian cancer by s.c. injecting $5 \times 10^6$ A2780 cells into nude mice (see Ref. 60). 1 day after tumor implantation, animals received an intratumoral injection with OV-αCD47-G1, OV-αCD47-G4 or OV-Q1 at the dose of $1 \times 10^5$ plaque-forming unit (pfu) per mouse, or saline as a placebo control. Tumor progression was monitored by measuring the tumor size. OV-αCD47-G1 was significantly more effective than OV-αCD47-G4 at inhibiting the progression of tumors in vivo and both are superior to OV-Q1 (FIG. 24). OV-Q1 moderately slowed tumor progression as compared to vehicle control (FIG. 24).

We also detected the distribution of anti-CD47 antibody after OV-αCD47-G1 or OV-αCD47-G4 treatment. NOD-scid IL2Rgamma$^{null}$ (NSG) mice were implanted with patient derived ovarian tumor fragments. 5 days after the implantation, animals received an intratumoral injection with OV-αCD47-G1, OV-αCD47-G4 or OV-Q1 at the dose of $1 \times 10^6$ plaque-forming unit (pfu) per mouse. 2 days after injection, the tumor fragments were isolated for immuno-histochemical staining with an anti-HSV antibody and anti-human Fc antibody.

OV-αCD47-G1 Enhances the Therapeutic Efficacy in an Immunocompetent Ovarian Cancer Mouse Model We next sought to evaluate the efficacy of OV-αCD47-G1 in an immunocompetent ovarian cancer mouse model. The mouse ID8 ovarian cancer cells were modified to express human CD47 for generating the ID8-hCD47 cells. The purpose for this modification is to make the αCD47-G1 antibody be able to bind to the human CD47 expressed on ID8-hCD47 cells. By intraperitoneal (i.p.) injection of ID8-hCD47 cells into immunocompetent wild-type C57BL/6 mice, we established an ovarian cancer immunocompetent mouse model and repeated the survival study with slight modification (FIG. 25). The treatment of these mice with OV-αCD47-G1 significantly prolonged their median survival when compared to those mice treated with OV-Q1 (FIG. 25).

The Combination of OV-αCD47-G1 with Olaparib Demonstrates an Enhanced Effect In Vitro and In Vivo Olaparib, a poly (ADP-ribose) polymerase (PARP) inhibitor, was the first PARP inhibitor approved for treating ovarian cancer. The PARP enzyme plays a role in DNA repair. Inhibiting this enzyme may contribute to cancer cell death and increased sensitivity to chemotherapy. By blocking this enzyme, DNA inside the cancerous cells is less likely to be repaired, leading to cell death and possibly a slow-down or stoppage of tumor growth. To detect whether OV-αCD47-G1 enhanced olaparib function for treating ovarian cancer, we performed the combination therapy with OV-αCD47-G1 and olaparib in vivo and in vitro. A2780 cells were treated with olaparib overnight, and the pretreated cells were 51Cr-labeled and used as target cells. These cells were then incubated with the supernatant from OV-αCD47-G1- or OV-Q1-infected cells. The effector NK cells and target cells were then co-cultured at the ratios of 40:1, 20:1, and 10:1 for 4 hours and assayed for cytotoxicity. The results demonstrated that olaparib pre-treatment enhanced NK cell cytotoxicity. In addition, we found that when olaparib was given with the supernatant from OV-αCD47-G1-infected cells, a significantly higher degree of NK cell cytotoxicity was observed as compared to either treatment alone (FIG. 26).

DISCUSSION

In this study, oncolytic virotherapy and antibody therapy were combined into a single therapeutic agent, aiming to destroy tumor cells directly by oncolysis and indirectly by converting the "cold" immune-evasive tumor microenvironment (TME) to a "hot" TME. A platform was developed by using oncolytic virus as a locoregional delivery vehicle of the full-length anti-CD47 antibody. This novel reagent can be administered intratumorally or intracranially post-surgery. This two-in-one, economical, and effective reagent should be able to be administered intratumorally pre-, intra-or post-operatively. Experimentally, the local delivery of OV-αCD47-G1 leads to (1) direct tumor lysis by oHSV; (2) innate immune cell infiltration and activation at the TME by oHSV; (3) blockade of the "don't eat me" signal normally mediated by the interaction between SIRP-α and CD47 expressed by macrophages and GBM, respectively; (4) αCD47-G1-mediated ADCP via bridging Fcγ receptors on macrophages and CD47 on GBM; and (5) αCD47-G1-mediated ADCC by NK cells. These multifaceted oncolysis and immunomodulatory roles collectively halt the spread of the GBM.

The systemic administration of the IgG4 anti-CD47 antibody (αCD47-G4) has shown significant anti-tumor activity in several types of malignancies in both preclinical and clinical studies (see, for example, Refs. 17-19). αCD47-G4 was constructed on a human IgG4 scaffold to minimize adverse effects resulting from Fc-dependent effector functions resulting from systemic administration of αCD47-G1 such as ADCC and ADCP. Using this approach, the αCD47-G4 mAb is largely limited to blocking the CD47-SIRPα axis while being unable to induce the FcR+innate immune effector cell responses of ADCC and ADCP, which result from Fc portion of the IgG1 mAb binding to the FcR on macrophages and NK cells. We therefore generated OV-αCD47-G1 as well as OV-αCD47-G4 to understand the importance of the Fc-FcR interaction in tumor clearance. While OV-αCD47-G1 and OV-αCD47-G4 released full length αCD47-G1 and αCD47-G4 mAbs, respectively, once GBM was infected, we found the anti-tumor efficacy of OV-αCD47-G1 to be significantly higher than OV-αCD47-G4 in vitro and in vivo. The data presented here suggest this is because αCD47-G4 can only block the CD47-SIRPα "don't-eat-me" signal, while αCD47-G1 combines this effect with Fc-dependent effector functions that result from ADCC and ADCP. Our antibody distribution data comparing systemic to locoregional delivery of the αCD47-G1 molecule suggest that the locoregional delivery of αCD47-G1 to the TME by OV-αCD47-G1 is an effective approach, even when compared to delivering the combination of oHSV and αCD47-G1 locoregionally but delivering them as two separate therapeutics.

Monoclonal antibodies (mAbs) have been widely and successfully used as targeted therapies in many cancers. However, the intravenous (i.v.), subcutaneous (s.c.), or intramuscular (i.m.) routes of administration may be impeding their efficacy in solid tumors with challenging TMEs. Because of large molecular sizes, s.c. and i.m. administration of mAbs require an additional absorption step, whereby mAbs are transported from the interstitial space into the lymphatic system prior to draining into the blood stream (see, for example, Ref. 34). However, regardless of the route of administration, the systemic delivery of mAbs is mainly distributed in plasma rather than the targeted tissue. To achieve an effective local dose in targeted tissues such as solid tumors, a high systemic dose of mAb is required but can result in adverse side effects and excessive cost. Moreover, traversing the blood-brain barrier (BBB) for mAb treatment of GBM is another challenge that largely precludes the systemic approach for mAb therapy in most GBM patients.

The current study suggests that re-engineered oHSV is an excellent platform to deliver mAbs in solid tumors such as GBM because the mAbs can be delivered beyond the BBB locoregionally by the GBM itself given the neurotropic properties of HSV. Further, the infected GBM can produce the mAb continually within the TME, thereby achieving an effective local dose and improving the likelihood of an anti-tumor response as FcR+ innate immune effect cells migrate to the virally infected tumor site. To achieve effective dose at the GBM microenvironment, the encoded anti-CD47 mAb gene is designed to be driven by a strong oHSV promoter, the promoter of the HSV-1 immediate early gene IE4/5.

TAMs have been found to be the major immune cells that promote tumor development in the GBM microenvironment (see, for example, Ref. 35). Since modulating TAMs is considered to be a promising anti-tumor strategy, targeting the CD47-SIRPα axis in these cells should be a good approach for the treatment of GBM. CD47 is highly expressed on numerous types of tumors including GBM (see, for example, Refs. 16, 26, 36). CD47 acts as an anti-phagocytic "don't eat me" signal by binding to SIRPα on the surfaces of macrophages. Activation of SIRP-α results in the inhibition of phagocytosis (see, for example, Ref. 18). Expression of CD47 helps the tumor cells escape from elimination by macrophages and facilitates their metastasis (see, for example, Ref. 37). Disrupting this CD47-SIRPα axis using mAbs has been shown to increase the phagocytosis of cancer cells and inhibit the progression of some hematological malignancies as well as solid tumors (see, for example, Refs. 17, 19, 38, 39).

αCD47-G4 (5F9-G4) is a humanized mAb whose construction was carried out by grafting its complementarity determining regions (CDRs) onto a human IgG4 scaffold to minimize Fc-dependent effector functions such as ADCC and ADCP. The αCD47-G1 antibody has identical CDRs but is grafted onto a human IgG1 scaffold. Therefore, they should have a near-identical ability to interrupt the "don't eat me" CD47-SIRPα interaction. Despite this, our study suggests that when locoregional delivery is available for GBM via its infection with oHSV, the αCD47-G1 antibody should be considered instead of αCD47-G4. This is because we show that the αCD47-G1 antibody has superior in vitro anti-tumor efficacy compared to that of αCD47-G4. Indeed, while both can block the CD47-SIRPα interaction, the αCD47-G1 antibody expressed by OV-αCD47-G1 can induce Fc-dependent ADCP mediated by macrophages and ADCC mediated by NK cells, while the αCD47-G4 antibody can only interrupt the "don't-eat-me" signal. Consistent with these data, our in vivo efficacy data showed that OV-αCD47-G1 played a better role than OV-αCD47-G4 in impeding GBM growth and facilitating its eradication. Our data also suggest that both the Fc-dependent anti-tumor effect and the effect resulting from the interruption of the CD47-SIRPα axis are important in the experimental treatment of GBM.

When systemic delivery of oncolytic virus is considered for tumors outside of the CNS, OV-αCD47-G4 may prove to be effective. Considering that both the oHSV backbone and anti-CD47 antibody have been tested in the clinic, our novel oHSV expressing an anti-CD47 antibody should likely be considered for translation into the clinic for the treatment of systemic solid tumors.

As αCD47-G1 and αCD47-G4 have an identical Fab recognizing CD47, any differences that we observed in phagocytosis must be attributable to the Fc portion of these two antibodies instead of the "don't eat signal". Our in vitro data show that IgG4-based antibodies have a weak phagocytosis effect, while IgG1-based antibodies induce a strong phagocytosis effect likely due to the distinct physical properties of IgG1 and IgG4 antibodies (see, for example, Ref. 30). When we used murine macrophages as effector cells and human GBM as target cells, the phagocytotic effect of the purified αCD47-G1 was dramatic while the same effect when using purified αCD47-G4 was relatively very moderate. These data suggest that the overall phagocytosis increased by αCD47-G1 was largely due to ADCP, while the phagocytosis from blocking CD47-SIRPα interaction was substantially less compared to ADCP. We may conclude that the Fc receptor-mediated ADCP effect is stronger than CD47-mediated "don't eat me" signaling. However, this could be due to a low binding affinity between murine SIRPα and human CD47, thus resulting in a low level of "don't eat me" signaling[40]. In fact, when we used human macrophages as effector cells against human GBM cells, we observed a significant but not dramatic difference between αCD47-G1 and αCD47-G4 as shown for murine macrophages against human GBM cells.

As provided herein, the full-length antibodies including both heavy and light chains are produced by a strong viral promoter, which can increase the locoregional delivery of antibodies in the TME but eliminate toxicities that could result from high dose systemic administration that would be required to achieve therapeutic levels in the CNS, however unlikely. Our therapeutic oHSV will not only activate the innate immune system but also continuously produce the mAb locally as long as the OV persists within the TME. In the ideal situation, once tumor cells are completely lysed by the OV, replicating virus dissipates and antibody production will cease thereby limiting the potential for long-term local tissue toxicity. Although our current approach is designed to produce a full-length antibody to directly target immune cells with IgG1 and IgG4 options, our platform can be used to deliver other forms of mAbs such as single chain mAbs (scFv) or any mAb with diverse functions such as T cell checkpoint blockade including anti-PD1, anti-PD-L1, anti-CTL4 or mAbs that directly target tumor cells, e.g., the anti-EGFR mAb (see, for example, Refs. 41-42).

Herein, data has shown development of a novel, effective oHSV platform to loco-regionally deliver antibodies to treat GBM, combining immune checkpoint inhibition (in macrophages in our case) and Fc-dependent innate immune cell functions. This platform can be extended to express other transgenes to target immune cells and/or tumor cells in TME and as a result to enhance the overall efficacy of oncolytic virotherapy.

Also provided is a combination of monoclonal antibody (mAb) and oncolytic virus together to improve the efficacy of ovarian cancer therapy. The results showed that OV-αCD47-G1 could not only directly lysis tumor cell, but also activate NK cell ADCC and macrophages ADCP function in vitro. Furthermore, OV-αCD47-G1 also blockaded the "don't eat me" signal normally mediated by the interaction between SIRP-α and CD47 expressed by macrophages and ovarian tumor cells, respectively. Therefore, OV-αCD47-G1 treatment significantly improved the virotherapy efficacy against ovarian tumor in vivo.

Provided was OV-αCD47-G1 and OV-αCD47-G4, which are designed to secret αCD47-G1 and αCD47-G4 respectively to the ovarian cancer tumor microenvironment after intratumoral administration. CD47 is highly expressed on numerous types of tumors including ovarian cancer cell. By binding to its receptor SIRPα on the surfaces of macrophages, CD47 that expressed on ovarian cancer cell can bring a "don't eat me" signal to macrophages and protect the tumor cells from been phagocytized (see, for example, Ref. 51). Anti-CD47 antibodies have been used for blocking CD47-SIRPα axis to enhance the phagocytosis of ovarian cancer cells and have been proved effective by many clinical and preclinical trials (see, for example, Refs. 51, 59, 61, 62).

We found that compared with αCD47-G4, αCD47-G1 induced much stronger phagocytosis of A2780 cells by both human and mouse macrophages, besides that, αCD47-G1 but not αCD47-G4 dramatically induced the cytotoxicity of A2780 cells by human NK cells. While αCD47-G1 and αCD47-G4 they shared identical CDRs, they should have a near-identical ability to interrupt the "don't eat me" CD47-SIRPα interaction. Indeed, while both of αCD47-G1 and αCD47-G4 can block the CD47-SIRPα interaction, the αCD47-G1 antibody can induce Fc-dependent ADCP mediated by macrophages and ADCC mediated by NK cells, while the αCD47-G4 antibody can only interrupt the "don't-eat-me" signal. Consistent with these, the in vivo results compared to OV-αCD47-G4 treatment, OV-αCD47-G1 showed a stronger anti-tumor therapy effect.

In summary, provided herein is an effective oHSV platform coding full-length mAbs with IgG1 scaffold to treat ovarian tumor, which combines direct tumor lysis, innate immune infiltration and activation, immune checkpoint inhibition of macrophages, and Fc-dependent innate immune cell cytotoxic functions.

Example 3: Methods and Materials

Cells

Human GBM cell lines (Gli36ΔEGFR, U251T2 and LN229) and mouse GBM cells (CT2A-hCD47) were cultured with DMEM supplemented with 10% FBS, penicillin (100 U/ml) and streptomycin (100 μg/ml). CT2A-hCD47 cells were generated by transfecting CT2A cells to express the human CD47 gene. GBM43 spheroid cells derived from a GBM patient and modified to express an FFL gene were named GBM43-FFL and used for in vivo imaging. GBM43 and GBM43-FFL cells were maintained as tumor spheres with basic neurobasal medium supplemented with 2% B27 (Gibco), human epidermal growth factor (EGF, 20 ng/ml) and fibroblast growth factor (FGF, 20 ng/ml) in low-attachment cell culture flasks. BT422 cells derived from a GBM patient were cultured with NS-A basal medium (StemCell) with EGF (20 ng/ml) and FGF (20 ng/ml) in low-attachment cell culture flasks. Human ovarian cancer cell line A2780, Chinese hamster ovary cell line CHO, sand monkey kidney epithelium-derived Vero cells were cultured with DMEM supplemented with 10% FBS, penicillin (100 U/ml) and streptomycin (100 μg/ml). Monkey kidney epithelium-derived Vero cells used for viral propagation and plaque-assay-based viral titration were maintained with the same media as the GBM cell lines. Gli36ΔEGFR and U251T2 cells were authenticated by the University of Arizona Genetics Core via STR profiling in January 2015, and LN229 in March 2018. GBM43 were authenticated by the Cell Line Characterization Core at MD Anderson Cancer Center in February 2019. Vero cells were not authenticated after receipt. GBM43 was developed at Mayo Clinic and other cell lines were originally developed by our group or obtained from ATCC. All cell lines were routinely tested for absence of mycoplasma using the MycoAlert Plus Mycoplasma Detection Kit from Lonza (Walkersville, MD).

Generation and Purification of αCD47-G1 and αCD47-G4

CHO cells were used to produce αCD47-G1 and αCD47-G4 for functionality tests. The light chain and heavy chain coding genes of αCD47-G4 were reconstructed as previously reported (see Ref. 20). αCD47-G1 used the same light chain coding gene as αCD47-G4, but a modified αCD47-G4 heavy chain coding gene that replaced the human IgG4 constant region with the human IgG1 constant region as the heavy chain coding gene. Lentiviral vectors were used to transduce CHO cells to express αCD47-G1 or αCD47-G4. The light chain and heavy chain coding genes were carried by different lentiviral vectors with GFP and mCherry selection markers, respectively, for sorting the double positive CHO cells by using a FACS Aria II cell sorter (BD Biosciences, San Jose, CA, USA). The conditional supernatants of the lentivirus-infected CHO cells were used to purify αCD47-G1 and αCD47-G4 by using a protein G column (Thermo Fisher, 89927). For the in vivo test, the purified αCD47-G1 was desalted by fast protein liquid chromatography (FPLC).

CD47 Binding and Blocking Assays

U251T2 cells pre-blocked with 2% BSA were incubated with 0, 5, 10, 25, 50,100, 250, 500, 1000, 2500, 5000 and 10000 ng/ml purified αCD47-G1 or αCD47-G4 antibodies for 30 min. Then the cells were washed twice and stained with APC-conjugated anti-human Fc (Jackson ImmunoResearch, 209-605-098) for 20 min. After that the cells were washed twice and stained with BV786-conjunaged anti-CD47 antibody (clone, B6H12, BD, 563758) for 20 min. The cells were analyzed by using Fortessa X20 flow cytometer (BD Biosciences). Median of mean fluorescence intensity (MFI) of APC and BV786 was used to determine CD47 binding and blocking capacity of αCD47-G1 and αCD47-G4.

Measurement of Antibody Concentration

For gliablastoma studies: U251T2 cells were infected with OV-Q1, OV-αCD47-G1 or OV-αCD47-G4 at a MOI of 2. Two hours after infection, the infection media were replaced with fresh media. The supernatants from each group were then harvested at 6, 12, 24, 48 and 72 hpi to measure antibody concentration by ELISA. A series amount of αCD47-G1 and αCD47-G4 antibodies purified from CHO cells with known concentrations served as standards. The ELISA was performed as previously reported with slight modification (see Ref. 43). Briefly. recombinant human CD47 protein (abcam, ab174029) was used as coating reagent. Anti-human Fc antibody (sigma, MAB1307) was used as detecting antibody.

For ovarian cancer studies: A2780 cells were saturated infected with OV-Q1, OV-αCD47-G1 or OV-αCD47-G4 at a MOI of 2. Two hours after infection, the infection media were replaced with fresh media. The supernatants from each group were then harvested at 6, 12, 24, 48 and 72 hpi to measure antibody concentration by ELISA. A series amount of αCD47-G1 and αCD47-G4 antibodies purified from CHO cells with known concentrations served as standards. The ELISA was performed as previously reported with slight modification (see Ref. 69). Briefly. recombinant human CD47 protein (abcam, ab174029) was used as coating reagent. Anti-human Fc antibody (sigma, MAB1307) was used as detecting antibody.

Generation of OV-αCD47-G1 and OV-αCD47-G4

OV-αCD47-G1 and OV-αCD47-G4 were generated by using the fHsvQuik-1 system as previously described (see, for example, Refs. 4, 21). For driving expression of the light chain and heavy chain simultaneously with a strong viral promoter, the light chain and heavy chain coding genes were linked with a DNA sequence encoding a T2A self-cleaving peptide. The linked αCD47-G1 and αCD47-G4 light chain and heavy sequences were inserted into pT-oriSIE4/5 following the HSV pIE4/5 promoter to construct pT-oriSIE4/5-αCD47-G1 or pT-oriSIE4/5-αCD47-G4. pT-oriSIE4/5-αCD47-G1, pT-oriSIE4/5-αCD47-G4 or pT-oriSIE4/5 was recombined with fHsvQuik-1 for engineering OV-αCD47-G1, OV-αCD47-G4 and OV-Q1, respectively. Vero cells were used for propagating and titrating the viruses. Virus titration was performed using plaque assays. Briefly, monolayer Vero cells were seeded in a 96-well plate. After 12 h, these cells were infected with gradient-diluted viral solutions. The infection media were replaced with DMEM supplemented with 10% FBS, after two-hour infection. GFP-positive plaques were observed and counted with a Zeiss fluorescence microscope (AXIO observer 7) 2 days after infection to calculate the viral titer. To concentrate and purify the viral particles of OV-Q1, OV-αCD47-G1 and OV-αCD47-G4, the culture media containing viruses were harvested and centrifuged at 3,000 g for 30 min. Then the supernatants were collected and ultra-centrifuged at 100,000 g for 1 hour. The pellets of virus were resuspended with saline as needed.

Oncolysis and Viral Production Assay

For gliablastoma studies: The in vitro oncolysis assay was performed as previously reported with slight modification (see Ref. 44). Briefly, U251T2 and Gli36ΔEGFR cells were seeded onto 96-well plates at densities of 5,000 cells/well and allowed to attach for 24 h. Cells were then treated with graded concentrations of OV-Q1, OV-αCD47-G1 or OV-αCD47-G4. After 3 days, cell lysis was measured by using the cell counting kit-8 (CCK-8, Abcam, ab228554) following the manufactory's protocol. CCK8 tetrazolium salt is reduced by cellular dehydrogenases to an orange formazan product that is soluble in tissue culture medium. The amount of formazan produced is directly proportional to the number of living cells and is measured by absorbance at 460 nm. Cell lysis and viral dose curves were established to evaluate the in vitro oncolytic efficacy of OV-αCD47-G1 and OV-αCD47-G4.

The viral replication assay was performed as previously reported (see Ref. 4). Briefly, monolayers of U251T2 and Gli36ΔEGFR cells were seeded on 96-well plates and infected with OV-Q1, OV-αCD47-G1 or OV-αCD47-G4 at a MOI of 2. Two hours after infection, the infection media were replaced with fresh media. The supernatants from each group were then harvested at 24, 48 and 72 hpi and viral titers were determined by plaque assays.

For ovarian cancer studies: The in vitro oncolysis assay was analyzed by Real-Time Cell Analysis. Briefly, A2780 cells were seeded onto 96-well plates at densities of 5,000 cells/well and allowed to attach for 24 h. Cells were then treated with graded concentrations of OV-Q1, OV-αCD47-G1 or OV-αCD47-G4. After 3 days, cell lysis was measured by Real-Time Cell Analysis machine following the manufactory's protocol.

Macrophage Generation

For isolating and culturing mouse BMDM, BALB/c mice were sacrificed at the time of bone marrow harvest. Bone marrow cells were extracted from the tibias and femurs by flushing with culture medium using a 25 G needle. The cells were then passed through a 70 μm nylon mesh (BD Bioscience) and washed three times with PBS. Extracted BM cells were implanted with 2.4×107/100 mm culture dish (BD Falcon) and cultured for 7 days in the presence of murine M-CSF (PeproTech, 315-02) medium (replacing culture medium on day 3 and day 5).

For isolating and culturing human primary macrophages, peripheral blood was collected from health donors. Human monocytes were isolated and enriched by using the RosetteSep™ Human Monocyte Enrichment Cocktail kit (Stemcell, Cat #15068) from the peripheral blood. The enriched human monocytes were cultured with RPMI-1640 medium containing 20 ng/ml human M-CSF (PeproTech, Cat #300-25-50UG) and 2% human serum for 7 days to induce the macrophage differentiation (replacing culture medium on day 3 and day 5).

Flow Cytometry-Based Phagocytosis Assay

For gliablastoma studies: For the phagocytosis assay of mouse BMDM, GBM43 and BT422 cells stained with CFSE (Thermo fisher, C34554) were used as target cells. BMDM and target cells were cocultured at a ratio of 1:2 for 2 hours in the presence of vehicle control, αCD47-G1 or αCD47-G4 at the dose of 5 μg/ml, in a humidified, 5% CO2 incubator at 37° C. in ultra-low-attachment 96-well U-bottom plates (Corning) in serum-free 1640 (Life Technologies). Then the cells were harvested by centrifuging at 400 g for 5 min at 4° C. and stained with anti-mouse CD11b (BD, 552850) to identify macrophages. For blocking Fc receptors, BMDM were pre-incubated with 10 μg/ml isotype human IgG1 (Biolegend, 403505) for 30 min. All flow cytometry data were collected using an Fortessa X20 flow cytometer (BD Biosciences). Phagocytosis was measured as the number of CD11b+CFSE+ macrophages, quantified as a percentage of the total CD11b+ macrophages.

For the phagocytosis assay of human primary macrophage, GBM43 cells stained with CFSE (Thermo fisher, C34554) were used as target cells. Human macrophages and target cells were cocultured at a ratio of 1:2 for 4 hours in the presence of vehicle control, αCD47-G1 or αCD47-G4 at the dose of 5 μg/ml, in a humidified, 5% CO2 incubator at 37° C. in ultra-low-attachment 96-well U-bottom plates (Corning) in serum-free 1640 (Life Technologies). Then the cells were harvested by centrifuging at 400 g for 5 min at 4° C. and stained with anti-human CD11b (BD, 552850) to identify macrophages. All flow cytometry data were collected using an Fortessa X20 flow cytometer (BD Biosciences). Phagocytosis was measured as the number of CD11b+CFSE+ macrophages, quantified as a percentage of the total CD11b+ macrophages.

For ovarian cancer studies: For the phagocytosis assay of human primary macrophage, A2780 cells stained with CFSE (Thermo fisher, C34554) were used as target cells. human macrophages and target cells were cocultured at a ratio of 1:2 for 4 hours in the presence of vehicle control, αCD47-G1 or αCD47-G4 at the dose of 5 μg/ml, in a humidified, 5% CO2 incubator at 37° C. in ultra-low-attachment 96-well U-bottom plates (Corning) in serum-free 1640 (Life Technologies). Then the cells were harvested by centrifuging at 400 g for 5 min at 4° C. and stained with anti-human CD45 (BD, 552850) to identify macrophages. All flow cytometry data were collected using an Fortessa X20 flow cytometer (BD Biosciences). Phagocytosis was measured as the number of CD11b+CFSE+ macrophages, quantified as a percentage of the total CD45+ macrophages.

58

NK Cell Cytotoxicity and Activation Assay

For gliablastoma studies: GBM43, BT422, U251T2, GBM30, LN229 and Gli36ΔEGFR cells were used as target cells. Primary human NK cells isolated from leukopaks of health donors using an NK cell isolation kit (MACSxpress Miltenyi Biotec, San Diego, CA) and an erythrocyte depletion kit (Miltenyi Biotec) were used as effector cells. The target cells were labeled with $51^{Cr}$ for 1 h. GBM43, BT422, U251T2, GBM30 and LN229 cells were cocultured with 1 μg/ml αCD47-G1 or αCD47-G4 antibodies or vehicle for 30 min. Gli36ΔEGFR cells were cocultured with gradient doses of αCD47-G1 or αCD47-G4 antibodies or vehicle for 30 min. Then the target cells were cocultured with isolated human primary NK cells at different effector:target ratios at 37° C. for 4 h. Release of $51^{Cr}$ was measured with a MicroBeta2 microplate radiometric counters (Perkin Elmer, Waltham, MA). Target cells incubated in complete media were for spontaneous and in 1% SDS media were used for maximal $51^{Cr}$ release control. The cell lysis percentages were calculated using the standard formula: 100×(cpm experimental release–cpm spontaneous release)/(cpm maximal release–cpm spontaneous release). The assays were performed in at least three technical replicates with NK cells from different donors. The expression of CD69, an NK cell activation marker, was measured after 4 hours coculture of NK cells and GBM43, GBM30 or U251T2 cells at a ratio of 1:1 with flow cytometer by using the anti-CD56 (BD, 557919) and anti-CD69 (BD, 562883) antibodies.

For ovarian cancer studies: A2780 cells were used as target cells. Primary human NK cells isolated from leukopaks of health donors using an NK cell isolation kit (MACSxpress Miltenyi Biotec, San Diego, CA) and an erythrocyte depletion kit (Miltenyi Biotec) were used as effector cells. The target cells were labeled with $^{51}$Cr for 1 h. A2780 cells were cocultured with 1 μg/ml αCD47-G1 or αCD47-G4 antibodies or vehicle for 30 min. Then the target cells were cocultured with isolated human primary NK cells at different effector: target ratios at 37° C. for 4 h. Release of $^{51}$Cr was measured with a MicroBeta$^2$ microplate radiometric counters (Perkin Elmer, Waltham, MA). Target cells incubated in complete media were for spontaneous and in 1% SDS media were used for maximal $^{51}$Cr release control. The cell lysis percentages were calculated using the standard formula: 100×(cpm experimental release–cpm spontaneous release)/(cpm maximal release–cpm spontaneous release). The assays were performed in at least three technical replicates with NK cells from different donors. The expression of CD69 and granzyme B, NK cell activation markers, were measured after 12 hours coculture of NK cells and A2780 cells at the ratio of 1:1 with flow cytometer by using the anti-CD56 antibody (BD, 557919), anti-granzyme B antibody and anti-CD69 (BD, 562883) antibody.

Immunoblot and Quantitative PCR

For gliablastoma studies: Immunoblotting was performed following a protocol as previously described4. U251T2 cells were infected with OV-Q1, OV-αCD47-G1 or OV-αCD47-G4 at a MOI of 2. Two hours after infection, the infection media were replaced with fresh media. The supernatants from each group were then harvested at 24 hpi. The supernatants harvested at 24 hours after medium change from CHO cells that were used for producing standard αCD47-G1 and αCD47-G4 were included as control. The protein components in 10 ml supernatants were extracted by a chloroform-methanol method. Anti-human IgG heavy chain (sigma, MAB1307), anti-human kappa chain (Thermo fisher, MA5-12117) and the corresponding secondary antibodies (LI-COR, 925-32210) were used to detect the heavy chain and light chain.

To evaluate the effect of αCD47-G1 and αCD47-G4 on activating transcription of typical mouse macrophage cytokine genes, mouse BMDM and GBM43 were cocultured at a ratio of 1:1 for 6 hours with or without the presence of 5 μg/ml αCD47-G1 or αCD47-G4. Then the total RNA was extracted for measuring the relative transcription of murine Arg1, Ccl2, Ccl4, Il1b, Il6, Il10, Il12b and Nos2 genes with the corresponding primers. 18s rRNA was used as internal control. To evaluate the effect of αCD47-G1 and αCD47-G4 on activating transcription of typical human macrophage cytokine genes, human macrophages and GBM43 were cocultured at a ratio of 1:1 for 6 hours with or without the presence of 5 μg/ml αCD47-G1 or αCD47-G4. Then the total RNA was extracted for measuring the relative transcription of human IL1B, IL6, IL10, IL12A and NOS2 genes with the corresponding primers. 18s rRNA was used as internal control.

For ovarian cancer studies studies: To evaluate the effect of αCD47-G1 and αCD47-G4 on activating transcription of typical mouse macrophage cytokine genes. Human macrophages and A2780 cells were cocultured at the ratio of 1:1 for 6 hours with or without the presence of 5 μg/ml αCD47-G1 or αCD47-G4. Then human macrophages were sorted by staining with anti-CD45 antibody. The total RNA was extracted for measuring the relative transcription of human IL1B, IL6, IL10, IL12A and NOS2 genes with the corresponding primers. 18s rRNA was used as internal control.

TABLE 2

Primers used in this study

| Name | Sequence | SEQ ID NO. |
|---|---|---|
| mIl6F | CTGCAAGAGACTTCCATCCAG | 14 |
| mIl6R | AGTGGTATAGACAGGTCTGTTGG | 15 |
| mArg1 F | CTCCAAGCCAAAGTCCTTAGAG | 16 |
| mArg1 R | GGAGCTGTCATTAGGGACATCA | 17 |
| mCcl2 F | ATCCACGGCATACTATCAACATC | 18 |
| mCcl2 R | TCGTAGTCATACGGTGTGGTG | 19 |
| mCcl4 F | CCAGCTCTGTGCAAACCTAACC | 20 |
| mCcl4 R | GCCACGAGCAAGAGGAGAGA | 21 |
| mNos2 f | TGACGGCAAACATGACTTCAG | 22 |
| mNos2 R | GGTGCCATCGGGCATCT | 23 |
| mIl10 F | CAGTACAGCCGGGAA GACAATAA | 24 |
| mIl10 R | CCGCAGCTCTAGGAGCATGT | 25 |
| mIl12b F | CCTGAAGTGTGAAGCACCAAATT | 26 |
| mIl12b R | CTTCAAGTCCATGTTTCTTTGCA | 27 |
| mIl1b F | GAAATGCCACCTTTTGACAGTG | 28 |
| mIl1b R | TGGATGCTCTCATCAGGACAG | 29 |
| hIL1B F | TTCGACACATGGGATAACGAGG | 30 |

TABLE 2-continued

Primers used in this study

| Name | Sequence | SEQ ID NO. |
|------|----------|------------|
| hIL1B R | TTTTTGCTGTGAGTCCCGGAG | 31 |
| hIL6 F | CCTGAACCTTCCAAAGATGGC | 32 |
| hIL6 R | TTCACCAGGCAAGTCTCCTCA | 33 |
| hIL12A F | ATGGCCCTGTGCCTTAGTAGT | 34 |
| hIL12A R | AGCTTTGCATTCATGGTCTTGA | 35 |
| hNOS2 F | AGGGACAAGCCTACCCCTC | 36 |
| hNOS2 R | CTCATCTCCCGTCAGTTGGT | 37 |
| hIL10 F | GACTTTAAGGGTTACCTGGGTTG | 38 |
| hIL10 R | TCACATGCGCCTTGATGTCTG | 39 |
| 18s rRNA F | GTAACCCGTTGAACCCCATT | 40 |
| 18s rRNA R | CCATCCAATCGGTAGTAGCG | 41 |

Animal Study

For gliablastoma studies: Six- to eight-week-old female athymic nude mice were purchased from Jackson Laboratories (Bar Harbor, Maine). For the survival studies, the mice were anesthetized and stereotactically injected with $1 \times 10^5$ GBM43-FFL cells, which express a firefly luciferase (FFL) gene, into the right frontal lobe of the brain (2 mm lateral and 1 mm anterior to bregma at a depth of 3 mm). The cells grew for 7 d, and animals were subsequently randomly divided into groups that were i.c. injected either with $2 \times 10^5$ PFU oHSV (OV-Q1, OV-αCD47-G1 or OV-αCD47-G4) in 3 pl of saline or with saline as control. Mice were subsequently monitored and weighed frequently for GBM disease progression. Luciferase-based in vivo images were taken from 15 days after tumor implantation to evaluate the tumor development. The mice were euthanized when they became moribund, with neurologic impairments and obvious weight loss.

For the in vivo anti-CD47 antibody distribution study, nude mice were stereotactically injected with $1 \times 10^5$ GBM43 into the same site of the brain mentioned above. The GBM cells were allowed to grow for 21 days, and the mice were randomly divided to four groups: Group 1, saline; Group 2, OV-Q1; Group 3, a combination of OV-Q1 plus i.p. delivery of αCD47-G1 and Group 4, OV-αCD47-G1. Group 1 received saline as control. Groups 2, 3, and 4 with OV treatment were i.c. injected with $2 \times 10^5$ PFU oHSV (OV-Q1 or OV-αCD47-G1) on day 21. Group 3 received i.p. injection of purified αCD47-G1 once at the dose of 150 μg per mouse on day 22, while other groups received i.p. saline as control. Mice were euthanized on day 23 for harvesting blood and brain. To determine the continuous release of anti-CD47 antibody from OV-αCD47-G1 infection, the above experiment was modified with the following changes: Group 3 received i.p. injection of purified αCD47-G1 twice at the dose of 150 μg per mouse on day 22 and 24, while other groups received i.p. saline as control. Mice were euthanized on day 25 for harvesting blood and brain. αCD47-G1 levels in plasma of the experimental mice were measured by ELISA. Brains isolated from the experimental mice were used for histologic study.

For establishing the immunocompetent mouse GBM model, six- to eight-week-old female C57BL/6 mice were purchased from Jackson Laboratories (Bar Harbor, Maine). The mice were anesthetized and stereotactically injected with $1 \times 10^5$ CT2A-hCD47 cells, which express a human CD47 gene, into the right frontal lobe of the brain (2 mm lateral and 1 mm anterior to bregma at a depth of 3 mm). The cells grew for 3 d, and animals were subsequently randomly divided into groups that were i.e. injected either with $2 \times 10^5$ PFU oHSV (OV-Q1, OV-αCD47-G1 or OV-αCD47-G4) in 3 pl of saline or with saline as control. Mice were subsequently monitored and weighed frequently for GBM disease progression. Luciferase-based in vivo images were taken from 15 days after tumor implantation to evaluate the tumor development. The mice were euthanized when they became moribund, with neurologic impairments and obvious weight loss.

To continuously deliver αCD47-G1 into the tumor site of the CT2A GBM mouse model, osmotic pumps (Alzet, Cat #1003D) were filled with 100 μl of desalted and concentrated αCD47-G1 at the concentration of 1.0 μg/μl. The pumps were connected with the brain infusion kit (Alzet, Cat #0008851) and implanted into the mice for continuous delivery αCD47-G1 to the tumor site.

For ovarian cancer studies: Six- to eight-week-old female athymic nude mice were purchased from Jackson Laboratories (Bar Harbor, Maine). For the survival studies, the mice were anesthetized and s.c. injected with $5 \times 10^6$ A2780 cells over the flank. 1 day after A2780 cells injection, animals were subsequently randomly divided into groups that were injected intratumorally either with $1 \times 10^5$ pfu oHSV (OV-Q1, OV-αCD47-G1 or OV-αCD47-G4) in 10 μl of saline or with saline as control. Mice were subsequently monitored for ovarian cancer progression. The mice were euthanized when the tumor diameter was over 30 mm.

For the in vivo anti-CD47 antibody distribution study, NSG were implanted with patient derived tumor fragments. The mice were randomly divided to 3 groups: Group 1: OV-Q1; Group 2: OV-αCD47-G1; and Group 3: OV-αCD47-G4. All groups with OV treatment were intratumorally injected with $2 \times 10^5$ PFU oHSV on day 5. Mice were euthanized on day 7 for harvesting the tumor fragments. Tumor fragments isolated from the experimental mice were used for histologic study.

For establishing the immunocompetent mouse ovarian tumor model, six- to eight-week-old female C57BL/6 mice were purchased from Jackson Laboratories (Bar Harbor, Maine). The mice were anesthetized and i.p injected with $1 \times 10^6$ ID8-hCD47 cells, which express a human CD47 gene, The cells grew for 3 d, and animals were subsequently randomly divided into groups that were i.p injected either with $2 \times 10^5$ PFU oHSV (OV-Q1, OV-αCD47-G1 or OV-αCD47-G4) in 10 μl of saline or with saline as control. Mice were subsequently monitored and weighed frequently for ovarian cancer disease progression. Luciferase-based in vivo images were taken from 15 days after tumor implantation to evaluate the tumor development. The mice were euthanized when they became moribund and obvious weight increased.

Immunohistochemistry Assay

For gliablastoma studies: Brains isolated from the experimental mice were placed in 10% neutral buffered formalin for a minimum of 72 h. After paraffin embedding, 4-μm-thick sections were cut from the blocks. H&E staining and immunohistochemical staining with anti-HSV (Cell marque, 361A-15-ASR), anti-human Fc (Jackson ImmunoResearch, 109-005-098), anti-CD11b (abcam, ab133357) antibodies were performed by the Pathology Core of Shared Resources at City of Hope Beckman Research Institute and National Medical Center. Stained slides were mounted and scanned for observation.

For ovarian cancer studies, tumor fragments isolated from the experimental mice were placed in 10% neutral buffered formalin for a minimum of 72 h. After paraffin embedding, 4-μm-thick sections were cut from the blocks. H&E staining and immunohistochemical staining with anti-HSV (Cell marque, 361A-15-ASR) and anti-human Fc (Jackson ImmunoResearch, 109-005-098) antibodies were performed by the Pathology Core of Shared Resources at City of Hope Beckman Research Institute and National Medical Center. Stained slides were mounted and scanned for observation.

Statistical Analysis

Descriptive statistics (means, standard deviations, median, counts, etc.) were used to summarize data. Continuous endpoints that are normally distributed with or without prior log transformation were compared between two or more independent conditions by Student's t test or one-way ANOVA, respectively. For data with repeated measures from the same subject/donor, a linear mixed model was used to compare matched groups by accounting for the underlying variance and covariance structure. For survival data, survival functions were estimated by the Kaplan-Meier method and compared by log rank test. All tests were two-sided. P values were adjusted for multiple comparisons by Holm's procedure or the Bonferroni method and a P value of 0.05 or less was defined as statistically significant. Statistical software GraphPad, R.3.6.3. and SAS 9.4 were used for the statistical analysis.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

Embodiments disclosed herein include embodiments P1 to P25 following.

Embodiment P1. A recombinant oncolytic herpes simplex virus (HSV) comprising: an expression cassette encoding a CD47 antibody.

Embodiment P2. The recombinant oncolytic virus of Embodiment P1, wherein the CD47 antibody comprises an IgG scaffold.

Embodiment P3. The recombinant oncolytic virus of Embodiment P2, wherein the IgG scaffold is selected from IgG1, IgG2, IgG3, and IgG4 scaffold.

Embodiment P4. The recombinant oncolytic virus of Embodiment P3 wherein the IgG scaffold is an IgG1 scaffold.

Embodiment P5. The recombinant oncolytic virus of Embodiment P3, wherein the IgG scaffold is an IgG4 scaffold.

Embodiment P6. The recombinant oncolytic virus of any one of Embodiment P1-P5, wherein the recombinant oncolytic virus does not comprise nucleic acid encoding a γ34.5 gene.

Embodiment P7. The recombinant oncolytic virus of any one of Embodiment P1-P6, wherein the recombinant oncolytic virus does not comprise nucleic acid encoding a functional ICP6 gene.

Embodiment P8. The recombinant oncolytic virus of any of the preceding Embodiments, wherein the nucleic acid encoding the CD47 antibody is under the control of a viral or tumor specific promoter.

Embodiment P9. The recombinant virus of any of the preceding Embodiments, wherein the viral promoter is a herpes simplex virus (HSV) immediate early (IE) promoter.

Embodiment P10. The recombinant oncolytic virus of Embodiment P9, wherein the HSV IE promoter is the IE 4/5 promoter.

Embodiment P11. The recombinant oncolytic virus of any of the preceding Embodiments, wherein the recombinant oncolytic virus comprises a nucleic acid encoding a marker within an ICP6 gene.

Embodiment P12. A pharmaceutical composition comprising: the recombinant oncolytic virus of any of the preceding Embodiments, and a pharmaceutically acceptable carrier.

Embodiment P13. A method for killing tumor cells in a subject comprising: administering to a subject an effective amount of the recombinant oncolytic virus of any of Embodiments P1-P11.

Embodiment P14. A method of treating a patient having cancer comprising administering to the patient an effective amount of the pharmaceutical composition of Embodiment P12 or the recombinant oncolytic virus of any of Embodiments P1-P11.

Embodiment P15. The method of Embodiment P14, wherein the cancer is a chronic cancer.

Embodiment P16. The method of any one of Embodiments P14-P15, wherein the cancer is an inflammatory chronic cancer.

Embodiment P17. The method of Embodiment P14, wherein the cancer is a CD47 expressing cancer.

Embodiment P18. The method of Embodiment P17, wherein the CD47 expressing cancer is selected from glioblastoma, ovarian cancer, pancreatic cancer, leukemia, and lymphoma.

Embodiment P19. The method of any of Embodiments P14-P18, wherein administering is by intratumoral, systemic, or intracavitary administration.

Embodiment P20. A method for immune modulation in a subject, comprising administering an effective amount of the recombinant oncolytic virus of any of Embodiments P1-P11.

Embodiment P21. The method of Embodiment P20, wherein immune modulation comprises activating natural killer (NK) cells.

Embodiment P22. The method of Embodiment P21, wherein activation of NK cells is measured as induction of cell-mediated antibody-dependent cellular cytotoxicity.

Embodiment P23. The method of Embodiment P21, wherein activation of NK cells is measured as expression of CD69 on NK cells.

Embodiment P24. The method of any of Embodiments P21-P22, wherein activation is measured as increased NK cell cytotoxicity.

Embodiment P25. The method of any of Embodiments P21-P24, wherein administering is by intratumoral, systemic, or intracavitary administration.

Embodiments disclosed herein include Embodiments 1 to 38 following.

Embodiment 1. A recombinant oncolytic herpes simplex virus (HSV) comprising a nucleic acid encoding an anti-CD47 antibody.

Embodiment 2. The recombinant oncolytic virus of Embodiment 1 wherein the anti-CD47 antibody is an IgG1 isotype.

Embodiment 3. The recombinant oncolytic virus of Embodiment 1 or 2, wherein the recombinant oncolytic virus does not comprise nucleic acid encoding a functional γ34.5 gene.

Embodiment 4. The recombinant oncolytic virus of any one of Embodiments 1 to 3, wherein the recombinant oncolytic virus does not comprise nucleic acid encoding a functional ICP6 gene.

Embodiment 5. The recombinant oncolytic virus of any one of Embodiments 1 to 4, wherein the nucleic acid encoding the anti-CD47 antibody is under the control of a viral or tumor specific promoter.

Embodiment 6. The recombinant virus of Embodiment 5, wherein the viral promoter is a herpes simplex virus (HSV) immediate early (IE) promoter.

Embodiment 7. The recombinant oncolytic virus of Embodiment 6, wherein the HSV IE promoter is the IE 4/5 promoter.

Embodiment 8. The recombinant oncolytic virus of any one of Embodiments 1 to 7, wherein the recombinant oncolytic virus comprises a nucleic acid encoding a marker within an ICP6 gene.

Embodiment 9. A pharmaceutical composition comprising: the recombinant oncolytic virus of any one of Embodiments 1 to 8, and a pharmaceutically acceptable carrier.

Embodiment 10. A pharmaceutical composition comprising: the recombinant oncolytic virus of any one of Embodiments 1 to 9, an anti-cancer agent, and a pharmaceutically acceptable carrier.

Embodiment 11. The pharmaceutical composition of Embodiment 10, wherein the anti-cancer agent is a checkpoint inhibitor.

Embodiment 12. The pharmaceutical composition of Embodiment 10, wherein the anti-cancer agent is a PARP inhibitor.

Embodiment 13. The pharmaceutical composition of Embodiment 12, wherein the PARP inhibitor is olaparib, rucaparib, niraparib, talazoparib, veliparib, pamiparib, CEP 9722, E7016, or 3-aminobenzamide.

Embodiment 14. A method for killing tumor cells in a subject comprising: administering to a subject an effective amount of the recombinant oncolytic virus of any one of Embodiments 1 to 8.

Embodiment 15. A method of treating a cancer in a subject in need, said method comprising administering to said subject an effective amount of the pharmaceutical composition of Embodiment 10 to 13 or the recombinant oncolytic virus of any one of Embodiments 1 to 8.

Embodiment 16. The method of Embodiment 15, wherein the cancer is a chronic cancer.

Embodiment 17. The method of Embodiment 16, wherein the cancer is an inflammatory chronic cancer.

Embodiment 18. The method of Embodiment 15, wherein the cancer is a CD47 expressing cancer.

Embodiment 19. The method of Embodiment 18, wherein the CD47 expressing cancer is selected from glioblastoma, ovarian cancer, pancreatic cancer, leukemia, and lymphoma.

Embodiment 20. The method of any of Embodiments 15-19, wherein administering is by intratumoral, systemic, or intracavitary administration.

Embodiment 21. A method for immune modulation in a subject, comprising administering an effective amount of the recombinant oncolytic virus of any of Embodiments 1-8 or the pharmaceutical composition of Embodiment 9.

Embodiment 22. The method of Embodiment 21, wherein immune modulation comprises activating natural killer (NK) cells.

Embodiment 23. The method of Embodiment 22, wherein activation of NK cells is measured as induction of cell-mediated antibody-dependent cellular cytotoxicity.

Embodiment 24. The method of Embodiment 22, wherein activation of NK cells is measured as expression of CD69 on NK cells.

Embodiment 25. The method of Embodiment 22 or 23, wherein activation is measured as increased NK cell cytotoxicity.

Embodiment 26. The method of any one of Embodiments 21 to 25, wherein administering is by intratumoral, systemic, or intracavitary administration.

Embodiment 27. A method of treating an overactive immune reaction in a subject in need, said method comprising administering to said subject an effective amount of the recombinant oncolytic virus of any of Embodiments 1-8 or the pharmaceutical composition of Embodiment 9.

Embodiment 28. The method of Embodiment 27, wherein said overactive immune reaction is asthma, eczema, or allergic rhinitis.

Embodiment 29. A method of treating an autoimmune disease in a subject in need, said method comprising administering to said subject an effective amount of the recombinant oncolytic virus of any of Embodiments 1-8 or the pharmaceutical composition of Embodiment 9.

Embodiment 30. The method of Embodiment 29, wherein said autoimmune disease is arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, or allergic asthma.

Embodiment 31. A method of treating an infectious disease in a subject in need, said method comprising administering to said subject an effective amount of the recombinant oncolytic virus of any of Embodiments 1-8 or the pharmaceutical composition of Embodiment 9.

Embodiment 32. The method of Embodiment 31, wherein the infectious disease is human immunodeficiency virus (HIV), COVID-19, influenza, pneumonia, syphilis, anthrax, gonorrhea, HPV, mononucleosis, West Nile fever, Zika, malaria, or plague Embodiment 33. A method of treating a cancer in a subject in need, said method comprising administering to said subject an effective amount of the recombinant oncolytic virus of any of Embodiments 1-8 or the pharmaceutical composition of Embodiment 9 in a first dosage form and an anti-cancer agent in a second dosage form.

Embodiment 34. The method of Embodiment 33, wherein the anti-cancer agent is a checkpoint inhibitor.

Embodiment 35. The method of Embodiment 33, wherein the anti-cancer agent is a PARP inhibitor.

Embodiment 36. The method of Embodiment 35, wherein the PARP inhibitor is olaparib, rucaparib, niraparib, talazoparib, veliparib, pamiparib, CEP 9722, E7016, or 3-aminobenzamide.

Embodiment 37. A method of treating a cancer in a subject in need, said method comprising administering to said subject an effective amount of the recombinant oncolytic virus of any of Embodiments 1-8 or the pharmaceutical composition of Embodiment 9 and an anti-cancer therapy.

Embodiment 38. The method of Embodiment 37, wherein the anti-cancer therapy is chemotherapy, radiation therapy, surgery, targeted therapy, immunotherapy, or cell therapy.

REFERENCES

1 Stupp, R. et al. Radiotherapy plus concomitant and adjuvant temozolomide for glioblastoma. *N Engl J Med* 352, 987-996, doi:10.1056/NEJMoa043330 (2005).
2 Andtbacka, R. H. et al. Talimogene Laherparepvec Improves Durable Response Rate in Patients With Advanced Melanoma. *J Clin Oncol* 33, 2780-2788, doi:10.1200/JCO.2014.58.3377 (2015).
3 Markert, J. M. et al. A phase 1 trial of oncolytic HSV-1, G207, given in combination with radiation for recurrent GBM demonstrates safety and radiographic responses. *Mol Ther* 22, 1048-1055, doi:10.1038/mt.2014.22 (2014).
4 Xu, B. et al. An oncolytic herpesvirus expressing E-cadherin improves survival in mouse models of glioblastoma. *Nature biotechnology*, doi:10.1038/nbt.4302 (2018).
5 Chen, X. et al. A combinational therapy of EGFR-CAR NK cells and oncolytic herpes simplex virus 1 for breast cancer brain metastases. *Oncotarget* 7, 27764-27777, doi:10.18632/oncotarget.8526 (2016).
6 Han, J. et al. TGFbeta Treatment Enhances Glioblastoma Virotherapy by Inhibiting the Innate Immune Response. *Cancer Res* 75, 5273-5282, doi:10.1158/0008-5472.CAN-15-0894 (2015).
7 Bolyard, C. et al. BAI1 Orchestrates Macrophage Inflammatory Response to HSV Infection-Implications for Oncolytic Viral Therapy. *Clin Cancer Res* 23, 1809-1819, doi:10.1158/1078-0432.CCR-16-1818 (2017).
8 Alvarez-Breckenridge, C. A. et al. NK cells impede glioblastoma virotherapy through NKp30 and NKp46 natural cytotoxicity receptors. *Nat Med* 18, 1827-1834, doi:10.1038/nm.3013 (2012).
9 Matlung, H. L., Szilagyi, K., Barclay, N. A. & van den Berg, T. K. The CD47-SIRPalpha signaling axis as an innate immune checkpoint in cancer. *Immunol Rev* 276, 145-164, doi:10.1111/imr.12527 (2017).
10 Bewersdorf, J. P., Shallis, R. M. & Zeidan, A. M. Immune checkpoint inhibition in myeloid malignancies: Moving beyond the PD-1/PD-L1 and CTLA-4 pathways. *Blood Rev,* 100709, doi:10.1016/j.blre.2020.100709 (2020).
11 Balkwill, F., Charles, K. A. & Mantovani, A. Smoldering and polarized inflammation in the initiation and promotion of malignant disease. *Cancer Cell* 7, 211-217, doi:10.1016/j.ccr.2005.02.013 (2005).
12 Coussens, L. M., Fingleton, B. & Matrisian, L. M. Matrix metalloproteinase inhibitors and cancer: trials and tribulations. *Science* 295, 2387-2392, doi:10.1126/science.1067100 (2002).
13 Wang, Y. et al. Polymeric nanoparticles promote macrophage reversal from M2 to M1 phenotypes in the tumor microenvironment. *Biomaterials* 112, 153-163, doi:10.1016/j.biomaterials.2016.09.034 (2017).
14 Saha, D., Martuza, R. L. & Rabkin, S. D. Macrophage Polarization Contributes to Glioblastoma Eradication by Combination Immunovirotherapy and Immune Checkpoint Blockade. *Cancer Cell* 32, 253-267 e255, doi:10.1016/j.ccell.2017.07.006 (2017).
15 Veillette, A. & Chen, J. SIRPalpha-CD47 Immune Checkpoint Blockade in Anticancer Therapy. *Trends Immunol* 39, 173-184, doi:10.1016/j.it.2017.12.005 (2018).
16 Willingham, S. B. et al. The CD47-signal regulatory protein alpha (SIRPa) interaction is a therapeutic target for human solid tumors. *Proc Natl Acad Sci USA* 109, 6662-6667, doi:10.1073/pnas.1121623109 (2012).
17 Gholamin, S. et al. Disrupting the CD47-SIRPalpha anti-phagocytic axis by a humanized anti-CD47 antibody is an efficacious treatment for malignant pediatric brain tumors. *Sci Transl Med* 9, doi:10.1126/scitranslmed.aaf2968 (2017).
18 Hutter, G. et al. Microglia are effector cells of CD47-SIRPalpha antiphagocytic axis disruption against glioblastoma. *Proc Natl Acad Sci USA* 116, 997-1006, doi:10.1073/pnas.1721434116 (2019).
19 Sikic, B. I. et al. First-in-Human, First-in-Class Phase I Trial of the Anti-CD47 Antibody Hu5F9-G4 in Patients With Advanced Cancers. *J Clin Oncol* 37, 946-953, doi:10. 1200/JCO.18.02018 (2019).
Liu, J. et al. Pre-Clinical Development of a Humanized Anti-CD47 Antibody with Anti-Cancer Therapeutic Potential. *PLoS One* 10, e0137345, doi:10.1371/journal.pone.0137345 (2015).
21 Terada, K., Wakimoto, H., Tyminski, E., Chiocca, E. A. & Saeki, Y. Development of a rapid method to generate multiple oncolytic HSV vectors and their in vivo evaluation using syngeneic mouse tumor models. *Gene Ther* 13, 705-714, doi:10.1038/sj.gt.3302717 (2006).
22 Mineta, T., Rabkin, S. D., Yazaki, T., Hunter, W. D. & Martuza, R. L. Attenuated multi-mutated herpes simplex virus-1 for the treatment of malignant gliomas. *Nat Med* 1, 938-943, doi:10.1038/nm0995-938 (1995).
23 Sharma, P. et al. 2A peptides provide distinct solutions to driving stop-carry on translational recoding. *Nucleic Acids Res* 40, 3143-3151, doi:10.1093/nar/gkr1176 (2012).
24 Iwamoto, C. et al. The BALB/c-specific polymorphic SIRPA enhances its affinity for human CD47, inhibiting phagocytosis against human cells to promote xenogeneic engraftment. *Exp Hematol* 42, 163-171 e161, doi:10.1016/j.exphem.2013.11.005 (2014).
25 Weischenfeldt, J. & Porse, B. Bone Marrow-Derived Macrophages (BMM): Isolation and Applications. *CSH Protoc* 2008, pdb prot5080, doi:10.1101/pdb.prot5080 (2008).
26 Jaiswal, S. et al. CD47 is upregulated on circulating hematopoietic stem cells and leukemia cells to avoid phagocytosis. *Cell* 138, 271-285, doi:10.1016/j.cell.2009.05.046 (2009).
27 Okazawa, H. et al. Negative regulation of phagocytosis in macrophages by the CD47-SHPS-1 system. *J Immunol* 174, 2004-2011, doi:10.4049/jimmunol.174.4.2004 (2005).
28 Kinder, M., Greenplate, A. R., Strohl, W. R., Jordan, R. E. & Brezski, R. J. An Fe engineering approach that modulates antibody-dependent cytokine release without altering cell-killing functions. *MAbs* 7, 494-504, doi:10.1080/19420862.2015.1022692 (2015).
29 Martinez, F. O. Analysis of gene expression and gene silencing in human macrophages. *Curr Protoc Immunol* Chapter 14, Unit 14 28 11-23, doi:10.1002/0471142735.im1428s96 (2012).
30 Vidarsson, G., Dekkers, G. & Rispens, T. IgG subclasses and allotypes: from structure to effector functions. *Front Immunol* 5, 520, doi:10.3389/fimmu.2014.00520 (2014).
31 Scott, A. M., Wolchok, J. D. & Old, L. J. Antibody therapy of cancer. *Nat Rev Cancer* 12, 278-287, doi:10.1038/nrc3236 (2012).

32 Kitange, G. J. et al. Induction of MGMT expression is associated with temozolomide resistance in glioblastoma xenografts. *Neuro Oncol* 11, 281-291, doi:10.1215/15228517-2008-090 (2009).

33 Derebe, M. G., Nanjunda, R. K., Gilliland, G. L., Lacy, E. R. & Chiu, M. L. Human IgG subclass cross-species reactivity to mouse and cynomolgus monkey Fcgamma receptors. *Immunol Lett* 197, 1-8, doi:10.1016/j.imlet.2018.02.006 (2018).

34 Keizer, R. J., Huitema, A. D., Schellens, J. H. & Beijnen, J. H. Clinical pharmacokinetics of therapeutic monoclonal antibodies. *Clin Pharmacokinet* 49, 493-507, doi:10.2165/11531280-000000000-00000 (2010).

35 Quail, D. F. & Joyce, J. A. The Microenvironmental Landscape of Brain Tumors. *Cancer Cell* 31, 326-341, doi:10.1016/j.ccell.2017.02.009 (2017).

36 Brown, E. J. & Frazier, W. A. Integrin-associated protein (CD47) and its ligands. *Trends Cell Biol* 11, 130-135, doi:10.1016/s0962-8924(00)01906-1 (2001).

37 Rivera, A., Fu, X., Tao, L. & Zhang, X. Expression of mouse CD47 on human cancer cells profoundly increases tumor metastasis in murine models. *BMC Cancer* 15, 964, doi:10.1186/s12885-015-1980-8 (2015).

38 Advani, R. et al. CD47 Blockade by Hu5F9-G4 and Rituximab in Non-Hodgkin's Lymphoma. *N Engl J Med* 379, 1711-1721, doi:10.1056/NEJMoa1807315 (2018).

39 Yu, X. Y. et al. A novel fully human anti-CD47 antibody as a potential therapy for human neoplasms with good safety. *Biochimie* 151, 54-66, doi:10.1016/j.biochi.2018.05.019 (2018).

40 Kwong, L. S., Brown, M. H., Barclay, A. N. & Hatherley, D. Signal-regulatory protein alpha from the NOD mouse binds human CD47 with an exceptionally high affinity—implications for engraftment of human cells. *Immunology* 143, 61-67, doi:10.1111/imm.12290 (2014).

41 Kimura, H. et al. Antibody-dependent cellular cytotoxicity of cetuximab against tumor cells with wild-type or mutant epidermal growth factor receptor. *Cancer Sci* 98, 1275-1280, doi:10.1111/j.1349-7006.2007.00510.x (2007).

42 Barok, M. et al. Trastuzumab causes antibody-dependent cellular cytotoxicity-mediated growth inhibition of submacroscopic JIMT-1 breast cancer xenografts despite intrinsic drug resistance. *Mol Cancer Ther* 6, 2065-2072, doi:10.1158/1535-7163.MCT-06-0766 (2007).

43 Chen, L. et al. Targeting FLT3 by chimeric antigen receptor T cells for the treatment of acute myeloid leukemia. *Leukemia* 31, 1830-1834, doi:10.1038/leu.2017.147 (2017).

44 Passaro, C. et al. Arming an Oncolytic Herpes Simplex Virus Type 1 with a Single-chain Fragment Variable Antibody against PD-1 for Experimental Glioblastoma Therapy. *Clin Cancer Res* 25, 290-299, doi:10.1158/1078-0432.CCR-18-2311 (2019).

45. C. Stewart, C. Ralyea, S. Lockwood, Ovarian Cancer: An Integrated Review. *Semin Oncol Nurs* 35, 151-156 (2019).

46 M. A. Roett, P. Evans, Ovarian cancer: an overview. *Am Fam Physician* 80, 609-616 (2009).

47. M. Kossai, A. Leary, J. Y. Scoazec, C. Genestie, Ovarian Cancer: A Heterogeneous Disease. *Pathobiology* 85, 41-49 (2018).

48. T. Grunewald, J. A. Ledermann, Targeted Therapies for Ovarian Cancer. *Best Pract Res Clin Obstet Gynaecol* 41, 139-152 (2017).

49. M. E. W. Logtenberg, F. A. Scheeren, T. N. Schumacher, The CD47-SIRPalpha Immune Checkpoint. *Immunity* 52, 742-752 (2020).

50. S. M. G. Hayat et al., CD47: role in the immune system and application to cancer therapy. *Cell Oncol* (Dordr) 43, 19-30 (2020).

51. S. B. Willingham et al., The CD47-signal regulatory protein alpha (SIRPα) interaction is a therapeutic target for human solid tumors. *Proc Natl Acad Sci USA* 109, 6662-6667 (2012).

52. R. M. Brightwell et al., The CD47 "don't eat me signal" is highly expressed in human ovarian cancer. *Gynecol Oncol* 143, 393-397 (2016).

53. Y. Kojima et al., CD47-blocking antibodies restore phagocytosis and prevent atherosclerosis. *Nature* 536, 86-90 (2016).

54. M. Feng et al., Phagocytosis checkpoints as new targets for cancer immunotherapy. *Nat Rev Cancer* 19, 568-586 (2019).

55. R. Liu et al., CD47 promotes ovarian cancer progression by inhibiting macrophage phagocytosis. *Oncotarget* 8, 39021-39032 (2017).

56. Y. Huang et al., A SIRPalpha-Fc fusion protein enhances the antitumor effect of oncolytic adenovirus against ovarian cancer. *Mol Oncol* 14, 657-668 (2020).

57. G. P. Adams, L. M. Weiner, Monoclonal antibody therapy of cancer. *Nat Biotechnol* 23, 1147-1157 (2005).

58. C. Touzeau, P. Moreau, C. Dumontet, Monoclonal antibody therapy in multiple myeloma. *Leukemia* 31, 1039-1047 (2017).

59. J. Liu et al., Pre-Clinical Development of a Humanized Anti-CD47 Antibody with Anti-Cancer Therapeutic Potential. *PLoS One* 10, e0137345 (2015).

60. G. J. Kitange et al., Induction of MGMT expression is associated with temozolomide resistance in glioblastoma xenografts. *Neuro Oncol* 11, 281-291 (2009).

61. A. Veillette, J. Chen, SIRPalpha-CD47 Immune Checkpoint Blockade in Anticancer Therapy. *Trends Immunol* 39, 173-184 (2018).

62. B. I. Sikic et al., First-in-Human, First-in-Class Phase I Trial of the Anti-CD47 Antibody Hu5F9-G4 in Patients With Advanced Cancers. *J Clin Oncol* 37, 946-953 (2019).

63. E. Cruz, V. Kayser, Monoclonal antibody therapy of solid tumors: clinical limitations and novel strategies to enhance treatment efficacy. *Biologics* 13, 33-51 (2019).

64. I. Melero, S. Hervas-Stubbs, M. Glennie, D. M. Pardoll, L. Chen, Immunostimulatory monoclonal antibodies for cancer therapy. *Nat Rev Cancer* 7, 95-106 (2007).

65. S. Crescioli et al., IgG4 Characteristics and Functions in Cancer Immunity. *Curr Allergy Asthma Rep* 16, 7 (2016).

66. J. D. Isaacs et al., A therapeutic human IgG4 monoclonal antibody that depletes target cells in humans. *Clin Exp Immunol* 106, 427-433 (1996).

67. K. Terada, H. Wakimoto, E. Tyminski, E. A. Chiocca, Y. Saeki, Development of a rapid method to generate multiple oncolytic HSV vectors and their in vivo evaluation using syngeneic mouse tumor models. *Gene Ther* 13, 705-714 (2006).

68. B. Xu et al., An oncolytic herpesvirus expressing E-cadherin improves survival in mouse models of glioblastoma. *Nature biotechnology*, (2018).

69. L. Chen et al., Targeting FLT3 by chimeric antigen receptor T cells for the treatment of acute myeloid leukemia. *Leukemia* 31, 1830-1834 (2017).

INFORMAL SEQUENCE LISTING
HSV pIE4/5 promoter (SEQ ID NO: 1)
TTCGCACTTCGTCCCAATATATATATATTATTAGG

GCGAAGTGCGAGCACTGGCGCCGTGCCCGACTCCG

CGCCGGCCCCGGGGGCGGGCCCGGGCGGCGGGGGG

CGGGTCTCTCCGGCGCACATAAAGGCCCGGCGCGA

CCGA

Anti-CD47 light chain signal peptide
                                    (SEQ ID NO: 2)
ATGGACATGAGGGTCTCTGCTCAGCTCCTGGGGCT

CCTGCTGCTCTGGCTCTCAGGAGCCAGATGT

Anti-CD47 light chain variable region
                                    (SEQ ID NO: 3)
GATATAGTGATGACCCAGTCTCCTTTGAGCCTTCC

GGTCACGCCCGGTGAACCTGCCAGTATCTCATGTC

GGTCCAGTCAATCCATAGTTTATTCTAATGGAAAT

ACGTATCTTGGTTGGTATCTCCAGAAGCCGGGTCA

GTCCCCACAGCTGTTGATATATAAGGTCTCCAATA

GATTCAGCGGCGTCCCGGATCGGTTCAGCGGCAGC

GGCTCAGGAACAGACTTTACTCTCAAAATTTCTCG

CGTAGAAGCTGAAGATGTAGGCGTCTATTATTGTT

TTCAAGGGAGTCACGTCCCCTATACATTCGGACAA

GGAACAAAATTGGAGATAAAA

Anti-CD47 light chain constant region
                                    (SEQ ID NO: 4)
CGAACTGTGGCTGCACCATCTGTCTTCATCTTCCC

GCCATCTGATGAGCAGTTGAAATCTGGAACTGCCT

CTGTTGTGTGCCTGCTGAATAACTTCTATCCCAGA

GAGGCCAAAGTACAGTGGAAGGTGGATAACGCCCT

CCAATCGGGTAACTCCCAGGAGAGTGTCACAGAGC

AGGACAGCAAGGACAGCACCTACAGCCTCAGCAAC

ACCCTGACGCTGAGCAAAGCAGACTACGAGAAACA

CAAAGTCTACGCCTGCGAAGTCACCCATCAGGGCC

TGAGCTCGCCCGTCACAAAGAGCTTCAACAGGGGA

GAGTGCTAG

IgG1 and IgG4 heavy chain signal peptide
                                    (SEQ ID NO: 5)
ATGGAATTTGGGCTGCGCTGGGTTTTCCTTGTTGC

TATTTTAAAAGATGTCCAGTGTGAC

Anti-CD47 heavy chain variable region
                                    (SEQ ID NO: 6)
GTCCAACTCGTGCAGTCCGGCGCGGAGGTTAAGAA

GCCTGGAGCGAGCGTCAAGGTATCATGCAAAGCCT

CCGGGTACACATTCACCAACTATAACATGCACTGG

GTTAGGCAGGCACCTGGCCAACGGCTCGAATGGAT

GGGAACCATATATCCGGGCAACGATGATACTAGCT

-continued
ACAATCAAAAATTTAAGGACCGCGTTACCATTACC

GCAGACACTTCAGCTTCTACCGCATATATGGAGCT

GAGCAGCCTCCGCTCCGAAGACACGGCCGTCTATT

ATTGCGCTCGCGGCGGATACCGAGCCATGGATTAC

TGGGGACAAGGGACACTTGTGACT

IgG1 heavy chain constant region CHi
                                    (SEQ ID NO: 7)
GTCTCCTCAGCCTCCACCAAGGGCCCATCGGTCTT

CCCCCTGGCACCCTCCTCCAAGAGCACCTCTGGGG

GCACAGCGGCCCTGGGCTGCCTGGTCAAGGACTAC

TTCCCCGAACCGGTGACGGTGTCGTGGAACTCAGG

CGCCCTGACCAGCGGCGTGCACACCTTCCCGGCTG

TCCTACAGTCCTCAGGACTCTACTCCCTCAGCAGC

GTGGTGACCGTGCCCTCCAGCAGCTTGGGCACCCA

GACCTACATCTGCAACGTGAATCACAAGCCCAGCA

ACACCAAGGTGGACAAGAAAGTT

IgG1 heavy chain hinge
                                    (SEQ ID NO: 8)
GAGCCCAAATCTTGTGACAAAACTCACACATGCCCA IgG1 heavy chain CH2 region
                                    (SEQ ID NO: 9)
CCGTGCCCAGCACCTGAACTCCTGGGGGGACCGTC

AGTCTTCCTCTTCCCCCCAAAACCCAAGGACACCC

TCATGATCTCCCGGACCCCTGAGGTCACATGCGTG

GTGGTGGACGTGAGCCACGAAGACCCTGAGGTCAA

GTTCAACTGGTACGTGGACGGCGTGGAGGTGCATA

ATGCCAAGACAAAGCCGCGGGAGGAGCAGTACAAC

AGCACGTACCGTGTGGTCAGCGTCCTCACCGTCCT

GCACCAGGACTGGCTGAATGGCAAGGAGTACAAGT

GCAAGGTCTCCAACAAAGCCCTCCCAGCCCCCATC

GAGAAAACCATCTCCAAAGCCAAA

IgG1 heavy chain CH3 region
                                    (SEQ ID NO: 10)
GGGCAGCCCCGAGAACCACAGGTGTACACCCTGCC

CCCATCCCGGGATGAGCTGACCAAGAACCAGGTCA

GCCTGACCTGCCTGGTCAAAGGCTTCTATCCCAGC

GACATCGCCGTGGAGTGGGAGAGCAATGGGCAGCC

GGAGAACAACTACAAGACCACGCCTCCCGTGCTGG

ACTCCGACGGCTCCTTCTTCCTCTACAGCAAGCTC

ACCGTGGACAAGAGCAGGTGGCAGCAGGGGAACGT

CTTCTCATGCTCCGTGATGCATGAGGCTCTGCACA

ACCACTACACGCAGAAGAGCCTCTCCCTGTCTCCG

GGTAAATGA

-continued

IgG4 heavy chain CH2 region (SEQ ID NO: 11)
GCACCTGAGTTCGAAGGGGGACCATCAGTCTTCCT

GTTCCCCCCAAAACCCAAGGACACTCTCATGATCT

CCCGGACCCCTGAGGTCACGTGCGTGGTGGTGGAC

GTGAGCCAGGAAGACCCCGAGGTCCAGTTCAACTG

GTACGTGGATGGCGTGGAGGTGCATAATGCCAAGA

CAAAGCCGCGGGAGGAGCAGTTCAACAGCACGTAC

CGTGTGGTCAGCGTCCTCACCGTCCTGCACCAGGA

CTGGCTGAACGGCAAGGAGTACAAGTGCAAGGTCT

CCAACAAAGGCCTCCCGTCCTCCATCGAGAAAACC

ATCTCCAAAGCCAAA

IgG4 heavy chain CH3 region (SEQ ID NO: 12)
GGGCAGCCCCGAGAGCCACAGGTGTACACCCTGCC

CCCATCCCAGGAGGAGATGACCAAGAACCAGGTCA

GCCTGACCTGCCTGGTCAAAGGCTTCTACCCCAGC

GACATCGCCGTGGAGTGGGAGAGCAATGGGCAGCC

GGAGAACAACTACAAGACCACGCCTCCCGTGCTGG

ACTCCGACGGCTCCTTCTTCCTCTACAGCAGGCTA

ACCGTGGACAAGAGCAGGTGGCAGGAGGGGAATGT

CTTCTCATGCTCCGTGATGCATGAGGCTCTGCACA

ACCACTACACACAGAAGAGCCTCTCCCTGTCTCTG

GGTAAAGCTAGCTGA

T2A (SEQ ID NO: 13)
GAGGGCAGAGGCAGTCTGCTGACATGCGGTGACGT

GGAAGAGAATCCCGGCCCT mIl6, forward sequence:

(SEQ ID NO: 14)
CTGCAAGAGACTTCCATCCAG mIl6, reverse sequence:

(SEQ ID NO: 15)
AGTGGTATAGACAGGTCTGTTGG mArg1, forward sequence:

(SEQ ID NO: 16)
CTCCAAGCCAAAGTCCTTAGAG mArg1, reverse sequence:

(SEQ ID NO: 17)
GGAGCTGTCATTAGGGACATCA mCcl2, forward sequence:

(SEQ ID NO: 18)
ATCCACGGCATACTATCAACATC mCcl2, reverse sequence:

(SEQ ID NO: 19)
TCGTAGTCATACGGTGTGGTG mCcl4, forward sequence:

(SEQ ID NO: 20)
CCAGCTCTGTGCAAACCTAACC mCcl4, reverse sequence:

(SEQ ID NO: 21)
GCCACGAGCAAGAGGAGAGA

-continued mNos2, forward sequence:

(SEQ ID NO: 22)
TGACGGCAAACATGACTTCAG mNos2, reverse sequence:

(SEQ ID NO: 23)
GGTGCCATCGGGCATCT mIl10, forward sequence:

(SEQ ID NO: 24)
CAGTACAGCCGGGAA GACAATAA mIl10, reverse sequence:

(SEQ ID NO: 25)
CCGCAGCTCTAGGAGCATGT mIl12b, forward s equence:

(SEQ ID NO: 26)
CCTGAAGTGTGAAGCACCAAATT mIl12b, reverse sequence:

(SEQ ID NO: 27)
CTTCAAGTCCATGTTTCTTTGCA mIl1b, forward sequence:

(SEQ ID NO: 28)
GAAATGCCACCTTTTGACAGTG mIl1b, reverse sequence:

(SEQ ID NO: 29)
TGGATGCTCTCATCAGGACAG hIL1B, forward sequence:

(SEQ ID NO: 30)
TTCGACACATGGGATAACGAGG hIL1B, reverse sequence:

(SEQ ID NO: 31)
TTTTTGCTGTGAGTCCCGGAG hIL6, forward sequence:

(SEQ ID NO: 32)
CCTGAACCTTCCAAAGATGGC hIL6, reverse sequence:

(SEQ ID NO: 33)
TTCACCAGGCAAGTCTCCTCA hIL12A, forward sequence:

(SEQ ID NO: 34)
ATGGCCCTGTGCCTTAGTAGT hIL12A, reverse sequence:

(SEQ ID NO: 35)
AGCTTTGCATTCATGGTCTTGA hNOS2, forward sequence:

(SEQ ID NO: 36)
AGGGACAAGCCTACCCCTC hNOS2, reverse sequence:

(SEQ ID NO: 37)
CTCATCTCCCGTCAGTTGGT hIL10, forward sequence:

(SEQ ID NO: 38)
GACTTTAAGGGTTACCTGGGTTG hIL10, reverse sequence:

(SEQ ID NO: 39)
TCACATGCGCCTTGATGTCTG 18s rRNA, forward sequence:

(SEQ ID NO: 40)
GTAACCCGTTGAACCCCATT 18s rRNA, reverse sequence:

(SEQ ID NO: 41)
CCATCCAATCGGTAGTAGCG

What is claimed is:

1. A recombinant oncolytic herpes simplex virus (HSV) comprising a nucleic acid encoding an anti-CD47 antibody, wherein the anti-CD47 antibody is an IgG1 isotype, and wherein the nucleic acid encoding the anti-CD47 antibody comprises:

a sequence of SEQ ID NO:3 encoding a light chain variable region, a sequence of SEQ ID NO:6 encoding a heavy chain variable region, a sequence of SEQ ID NO: 4 encoding a light chain constant region, and a sequence of SEQ ID NO:7 encoding a heavy chain constant region $CH_1$.

2. The recombinant oncolytic virus of claim 1, wherein the recombinant oncolytic virus does not comprise a nucleic acid encoding a functional ICP6 gene or does not comprise a nucleic acid encoding a functional γ34.5 gene.

3. The recombinant oncolytic virus of claim 1, wherein the nucleic acid encoding the anti-CD47 antibody is under the control of a viral or tumor specific promoter.

4. The recombinant oncolytic virus of claim 3, wherein the viral promoter is a herpes simplex virus (HSV) immediate early (IE) promoter.

5. A pharmaceutical composition comprising: the recombinant oncolytic virus of claim 1, and a pharmaceutically acceptable carrier.

6. A pharmaceutical composition comprising: the recombinant oncolytic virus of claim 1, an anti-cancer agent, and a pharmaceutically acceptable carrier.

7. The pharmaceutical composition of claim 6, wherein the anti-cancer agent is a PARP inhibitor or a checkpoint inhibitor.

8. The pharmaceutical composition of claim 7, wherein the PARP inhibitor is olaparib, rucaparib, niraparib, talazoparib, veliparib, pamiparib, CEP 9722, E7016, or 3-aminobenzamide.

9. A method of treating a CD47 expressing cancer in a subject in need, said method comprising administering to said subject an effective amount of the recombinant oncolytic virus of claim 1.

10. The method of claim 9, wherein the CD47 expressing cancer is selected from glioblastoma, ovarian cancer, pancreatic cancer, leukemia, and lymphoma.

11. The method of claim 10, wherein the CD47 expressing cancer is glioblastoma.

12. The method of claim 10, wherein the CD47 expressing cancer is ovarian cancer.

13. A method of treating a CD47 expressing cancer in a subject in need, said method comprising administering to said subject an effective amount of the recombinant oncolytic virus of claim 1 in a first dosage form and an anti-cancer agent in a second dosage form.

14. A method of treating a CD47 expressing cancer in a subject in need, said method comprising administering to said subject an effective amount of the recombinant oncolytic virus of claim 1 and a cancer therapy.

15. The recombinant oncolytic HSV of claim 1, wherein the nucleic acid encoding the anti-CD47 antibody further comprises:

a sequence of SEQ ID NO:9 encoding a IgG1 heavy chain constant region $CH_2$ and a sequence of SEQ ID NO:10 encoding a IgG1 heavy chain constant region $CH_3$.

* * * * *

SEQUENCE LISTING

<160> NUMBER OF SEQ ID NOS: 41

<210> SEQ ID NO 1
<211> LENGTH: 144
<212> TYPE: DNA
<213> ORGANISM: Artificial Sequence
<220> FEATURE:
<223> OTHER INFORMATION: Synthetic construct

<400> SEQUENCE: 1

```
ttcgcacttc gtcccaatat atatatatta ttagggcgaa gtgcgagcac tggcgccgtg      60
cccgactccg cgccggcccc ggggcgggc ccgggcggcg ggggcgggt ctctccggcg      120 cacataaagg cccggcgcga ccga                                            144
```

<210> SEQ ID NO 2
<211> LENGTH: 66
<212> TYPE: DNA
<213> ORGANISM: Artificial Sequence
<220> FEATURE:
<223> OTHER INFORMATION: Synthetic construct

<400> SEQUENCE: 2

```
atggacatga gggtctctgc tcagctcctg gggctcctgc tgctctggct ctcaggagcc      60
agatgt                                                                66
```

<210> SEQ ID NO 3
<211> LENGTH: 336
<212> TYPE: DNA
<213> ORGANISM: Artificial Sequence
<220> FEATURE:
<223> OTHER INFORMATION: Synthetic construct

<400> SEQUENCE: 3

```
gatatagtga tgacccagtc tcctttgagc cttccggtca cgcccggtga acctgccagt      60
atctcatgtc ggtccagtca atccatagtt tattctaatg gaaatacgta tcttggttgg      120
tatctccaga agccgggtca gtccccacag ctgttgatat ataaggtctc caatagattc      180
agcggcgtcc cggatcggtt cagcggcagc ggctcaggaa cagactttac tctcaaaatt      240
tctcgcgtag aagctgaaga tgtaggcgtc tattattgtt ttcaagggag tcacgtcccc      300
tatacattcg gacaaggaac aaaattggag ataaaa                               336
```

<210> SEQ ID NO 4
<211> LENGTH: 324
<212> TYPE: DNA
<213> ORGANISM: Artificial Sequence
<220> FEATURE:
<223> OTHER INFORMATION: Synthetic construct

<400> SEQUENCE: 4

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcaac accctgacgc tgagcaaagc agactacgag      240
aaacacaaag tctacgcctg cgaagtcacc catcagggcc tgagctcgcc cgtcacaaag      300
agcttcaaca ggggagagtg ctag                                            324
```

<210> SEQ ID NO 5
<211> LENGTH: 60

```
<212> TYPE: DNA
<213> ORGANISM: Artificial Sequence
<220> FEATURE:
<223> OTHER INFORMATION: Synthetic construct

<400> SEQUENCE: 5
atggaatttg ggctgcgctg ggtttttcctt gttgctattt taaaagatgt ccagtgtgac    60

<210> SEQ ID NO 6
<211> LENGTH: 339
<212> TYPE: DNA
<213> ORGANISM: Artificial Sequence
<220> FEATURE:
<223> OTHER INFORMATION: Synthetic construct

<400> SEQUENCE: 6
gtccaactcg tgcagtccgg cgcggaggtt aagaagcctg gagcgagcgt caaggtatca    60
tgcaaagcct ccgggtacac attcaccaac tataacatgc actgggttag gcaggcacct   120
ggccaacggc tcgaatggat gggaaccata tatccgggca acgatgatac tagctacaat   180
caaaaattta aggaccgcgt taccattacc gcagacactt cagcttctac cgcatatatg   240
gagctgagca gcctccgctc cgaagacacg gccgtctatt attgcgctcg cggcggatac   300
cgagccatgg attactgggg acaagggaca cttgtgact                          339

<210> SEQ ID NO 7
<211> LENGTH: 303
<212> TYPE: DNA
<213> ORGANISM: Artificial Sequence
<220> FEATURE:
<223> OTHER INFORMATION: Synthetic construct

<400> SEQUENCE: 7
gtctcctcag cctccaccaa gggcccatcg gtcttcccc tggcaccctc ctccaagagc     60
acctctgggg gcacagcggc cctgggctgc ctggtcaagg actacttccc cgaaccggtg   120
acggtgtcgt ggaactcagg cgccctgacc agcggcgtgc acaccttccc ggctgtccta   180
cagtcctcag gactctactc cctcagcagc gtggtgaccg tgccctccag cagcttgggc   240
acccagacct acatctgcaa cgtgaatcac aagcccagca acaccaaggt ggacaagaaa   300
gtt                                                                 303

<210> SEQ ID NO 8
<211> LENGTH: 36
<212> TYPE: DNA
<213> ORGANISM: Artificial Sequence
<220> FEATURE:
<223> OTHER INFORMATION: Synthetic construct

<400> SEQUENCE: 8
gagcccaaat cttgtgacaa aactcacaca tgccca                              36

<210> SEQ ID NO 9
<211> LENGTH: 339
<212> TYPE: DNA
<213> ORGANISM: Artificial Sequence
<220> FEATURE:
<223> OTHER INFORMATION: Synthetic construct

<400> SEQUENCE: 9
ccgtgcccag cacctgaact cctggggga ccgtcagtct tcctcttccc cccaaaaccc      60
aaggacaccc tcatgatctc ccggacccct gaggtcacat gcgtggtggt ggacgtgagc   120
```

```
cacgaagacc ctgaggtcaa gttcaactgg tacgtggacg gcgtggaggt gcataatgcc      180
aagacaaagc cgcgggagga gcagtacaac agcacgtacc gtgtggtcag cgtcctcacc      240
gtcctgcacc aggactggct gaatggcaag gagtacaagt gcaaggtctc caacaaagcc      300
ctcccagccc ccatcgagaa aaccatctcc aaagccaaa                             339
```

```
<210> SEQ ID NO 10
<211> LENGTH: 324
<212> TYPE: DNA
<213> ORGANISM: Artificial Sequence
<220> FEATURE:
<223> OTHER INFORMATION: Synthetic construct

<400> SEQUENCE: 10
gggcagcccc gagaaccaca ggtgtacacc ctgcccccat cccgggatga gctgaccaag       60
aaccaggtca gcctgacctg cctggtcaaa ggcttctatc ccagcgacat cgccgtggag      120
tgggagagca atgggcagcc ggagaacaac tacaagacca cgcctcccgt gctggactcc      180
gacggctcct tcttcctcta cagcaagctc accgtggaca agagcaggtg gcagcagggg      240
aacgtcttct catgctccgt gatgcatgag gctctgcaca accactacac gcagaagagc      300
ctctccctgt ctccgggtaa atga                                            324
```

```
<210> SEQ ID NO 11
<211> LENGTH: 330
<212> TYPE: DNA
<213> ORGANISM: Artificial Sequence
<220> FEATURE:
<223> OTHER INFORMATION: Synthetic construct

<400> SEQUENCE: 11
gcacctgagt tcgaaggggg accatcagtc ttcctgttcc ccccaaaacc caaggacact       60
ctcatgatct cccggacccc tgaggtcacg tgcgtggtgg tggacgtgag ccaggaagac      120
cccgaggtcc agttcaactg gtacgtggat ggcgtggagg tgcataatgc caagacaaag      180
ccgcgggagg agcagttcaa cagcacgtac cgtgtggtca gcgtcctcac cgtcctgcac      240
caggactggc tgaacggcaa ggagtacaag tgcaaggtct ccaacaaagg cctcccgtcc      300
tccatcgaga aaaccatctc caaagccaaa                                      330
```

```
<210> SEQ ID NO 12
<211> LENGTH: 330
<212> TYPE: DNA
<213> ORGANISM: Artificial Sequence
<220> FEATURE:
<223> OTHER INFORMATION: Synthetic construct

<400> SEQUENCE: 12
gggcagcccc gagagccaca ggtgtacacc ctgcccccat cccaggagga gatgaccaag       60
aaccaggtca gcctgacctg cctggtcaaa ggcttctacc ccagcgacat cgccgtggag      120
tgggagagca atgggcagcc ggagaacaac tacaagacca cgcctcccgt gctggactcc      180
gacggctcct tcttcctcta cagcaggcta accgtggaca agagcaggtg gcaggagggg      240
aatgtcttct catgctccgt gatgcatgag gctctgcaca accactacac acagaagagc      300
ctctccctgt ctctgggtaa agctagctga                                      330
```

```
<210> SEQ ID NO 13
<211> LENGTH: 54
<212> TYPE: DNA
<213> ORGANISM: Artificial Sequence
```

```
<220> FEATURE:
<223> OTHER INFORMATION: Synthetic construct

<400> SEQUENCE: 13
gagggcagag gcagtctgct gacatgcggt gacgtggaag agaatcccgg ccct          54

<210> SEQ ID NO 14
<211> LENGTH: 21
<212> TYPE: DNA
<213> ORGANISM: Artificial Sequence
<220> FEATURE:
<223> OTHER INFORMATION: Synthetic construct

<400> SEQUENCE: 14
ctgcaagaga cttccatcca g          21

<210> SEQ ID NO 15
<211> LENGTH: 23
<212> TYPE: DNA
<213> ORGANISM: Artificial Sequence
<220> FEATURE:
<223> OTHER INFORMATION: Synthetic construct

<400> SEQUENCE: 15
agtggtatag acaggtctgt tgg          23

<210> SEQ ID NO 16
<211> LENGTH: 22
<212> TYPE: DNA
<213> ORGANISM: Artificial Sequence
<220> FEATURE:
<223> OTHER INFORMATION: Synthetic construct

<400> SEQUENCE: 16
ctccaagcca aagtccttag ag          22

<210> SEQ ID NO 17
<211> LENGTH: 22
<212> TYPE: DNA
<213> ORGANISM: Artificial Sequence
<220> FEATURE:
<223> OTHER INFORMATION: Synthetic construct

<400> SEQUENCE: 17
ggagctgtca ttagggacat ca          22

<210> SEQ ID NO 18
<211> LENGTH: 23
<212> TYPE: DNA
<213> ORGANISM: Artificial Sequence
<220> FEATURE:
<223> OTHER INFORMATION: Synthetic construct

<400> SEQUENCE: 18
atccacggca tactatcaac atc          23

<210> SEQ ID NO 19
<211> LENGTH: 21
<212> TYPE: DNA
<213> ORGANISM: Artificial Sequence
<220> FEATURE:
<223> OTHER INFORMATION: Synthetic construct

<400> SEQUENCE: 19
tcgtagtcat acggtgtggt g          21
```

-continued

```
<210> SEQ ID NO 20
<211> LENGTH: 22
<212> TYPE: DNA
<213> ORGANISM: Artificial Sequence
<220> FEATURE:
<223> OTHER INFORMATION: Synthetic construct

<400> SEQUENCE: 20
ccagctctgt gcaaacctaa cc                                                       22

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
gccacgagca agaggagaga                                                          20

<210> SEQ ID NO 22
<211> LENGTH: 21
<212> TYPE: DNA
<213> ORGANISM: Artificial Sequence
<220> FEATURE:
<223> OTHER INFORMATION: Synthetic construct

<400> SEQUENCE: 22
tgacggcaaa catgacttca g                                                        21

<210> SEQ ID NO 23
<211> LENGTH: 17
<212> TYPE: DNA
<213> ORGANISM: Artificial Sequence
<220> FEATURE:
<223> OTHER INFORMATION: Synthetic construct

<400> SEQUENCE: 23
ggtgccatcg ggcatct                                                             17

<210> SEQ ID NO 24
<211> LENGTH: 23
<212> TYPE: DNA
<213> ORGANISM: Artificial Sequence
<220> FEATURE:
<223> OTHER INFORMATION: Synthetic construct

<400> SEQUENCE: 24
cagtacagcc gggaagacaa taa                                                      23

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
ccgcagctct aggagcatgt                                                          20

<210> SEQ ID NO 26
<211> LENGTH: 23
<212> TYPE: DNA
<213> ORGANISM: Artificial Sequence
<220> FEATURE:
<223> OTHER INFORMATION: Synthetic construct
```

-continued

```
<400> SEQUENCE: 26
cctgaagtgt gaagcaccaa att                                        23

<210> SEQ ID NO 27
<211> LENGTH: 23
<212> TYPE: DNA
<213> ORGANISM: Artificial Sequence
<220> FEATURE:
<223> OTHER INFORMATION: Synthetic construct

<400> SEQUENCE: 27
cttcaagtcc atgtttcttt gca                                        23

<210> SEQ ID NO 28
<211> LENGTH: 22
<212> TYPE: DNA
<213> ORGANISM: Artificial Sequence
<220> FEATURE:
<223> OTHER INFORMATION: Synthetic construct

<400> SEQUENCE: 28
gaaatgccac cttttgacag tg                                         22

<210> SEQ ID NO 29
<211> LENGTH: 21
<212> TYPE: DNA
<213> ORGANISM: Artificial Sequence
<220> FEATURE:
<223> OTHER INFORMATION: Synthetic construct

<400> SEQUENCE: 29
tggatgctct catcaggaca g                                          21

<210> SEQ ID NO 30
<211> LENGTH: 22
<212> TYPE: DNA
<213> ORGANISM: Artificial Sequence
<220> FEATURE:
<223> OTHER INFORMATION: Synthetic construct

<400> SEQUENCE: 30
ttcgacacat gggataacga gg                                         22

<210> SEQ ID NO 31
<211> LENGTH: 21
<212> TYPE: DNA
<213> ORGANISM: Artificial Sequence
<220> FEATURE:
<223> OTHER INFORMATION: Synthetic construct

<400> SEQUENCE: 31
tttttgctgt gagtcccgga g                                          21

<210> SEQ ID NO 32
<211> LENGTH: 21
<212> TYPE: DNA
<213> ORGANISM: Artificial Sequence
<220> FEATURE:
<223> OTHER INFORMATION: Synthetic construct

<400> SEQUENCE: 32
cctgaacctt ccaaagatgg c                                          21

<210> SEQ ID NO 33
```

-continued

```
<211> LENGTH: 21
<212> TYPE: DNA
<213> ORGANISM: Artificial Sequence
<220> FEATURE:
<223> OTHER INFORMATION: Synthetic construct

<400> SEQUENCE: 33
ttcaccaggc aagtctcctc a                                        21

<210> SEQ ID NO 34
<211> LENGTH: 21
<212> TYPE: DNA
<213> ORGANISM: Artificial Sequence
<220> FEATURE:
<223> OTHER INFORMATION: Synthetic construct

<400> SEQUENCE: 34
atggccctgt gccttagtag t                                        21

<210> SEQ ID NO 35
<211> LENGTH: 22
<212> TYPE: DNA
<213> ORGANISM: Artificial Sequence
<220> FEATURE:
<223> OTHER INFORMATION: Synthetic construct

<400> SEQUENCE: 35
agctttgcat tcatggtctt ga                                       22

<210> SEQ ID NO 36
<211> LENGTH: 19
<212> TYPE: DNA
<213> ORGANISM: Artificial Sequence
<220> FEATURE:
<223> OTHER INFORMATION: Synthetic construct

<400> SEQUENCE: 36
agggacaagc ctacccctc                                           19

<210> SEQ ID NO 37
<211> LENGTH: 20
<212> TYPE: DNA
<213> ORGANISM: Artificial Sequence
<220> FEATURE:
<223> OTHER INFORMATION: Synthetic construct

<400> SEQUENCE: 37
ctcatctccc gtcagttggt                                          20

<210> SEQ ID NO 38
<211> LENGTH: 23
<212> TYPE: DNA
<213> ORGANISM: Artificial Sequence
<220> FEATURE:
<223> OTHER INFORMATION: Synthetic construct

<400> SEQUENCE: 38
gactttaagg gttacctggg ttg                                      23

<210> SEQ ID NO 39
<211> LENGTH: 21
<212> TYPE: DNA
<213> ORGANISM: Artificial Sequence
<220> FEATURE:
<223> OTHER INFORMATION: Synthetic construct

<400> SEQUENCE: 39
```

-continued

```
tcacatgcgc cttgatgtct g                                        21

<210> SEQ ID NO 40
<211> LENGTH: 20
<212> TYPE: DNA
<213> ORGANISM: Artificial Sequence
<220> FEATURE:
<223> OTHER INFORMATION: Synthetic construct

<400> SEQUENCE: 40
gtaacccgtt gaaccccatt                                          20

<210> SEQ ID NO 41
<211> LENGTH: 20
<212> TYPE: DNA
<213> ORGANISM: Artificial Sequence
<220> FEATURE:
<223> OTHER INFORMATION: Synthetic construct

<400> SEQUENCE: 41
ccatccaatc ggtagtagcg                                          20
```